US012624309B2

(12) United States Patent
Womack

(10) Patent No.: US 12,624,309 B2
(45) Date of Patent: May 12, 2026

(54) ENOL ETHER PROPERFUME

(71) Applicant: Firmenich SA, Satigny (CH)

(72) Inventor: Gary Bernard Womack, Plainsboro, NJ (US)

(73) Assignee: FIRMENICH SA, Satigny (CH)

(*) Notice: Subject to any disclaimer, the term of this patent is extended or adjusted under 35 U.S.C. 154(b) by 677 days.

(21) Appl. No.: 18/001,560

(22) PCT Filed: Jun. 10, 2021

(86) PCT No.: PCT/EP2021/065606

§ 371 (c)(1),
(2) Date: Dec. 12, 2022

(87) PCT Pub. No.: WO2021/250164

PCT Pub. Date: Dec. 16, 2021

(65) Prior Publication Data

US 2023/0220298 A1 Jul. 13, 2023

Related U.S. Application Data

(60) Provisional application No. 63/038,160, filed on Jun. 12, 2020.

(30) Foreign Application Priority Data

Jun. 25, 2020 (EP) .................................... 20182200

(51) Int. Cl.
*C11B 9/00* (2006.01)
*C07C 69/734* (2006.01)

(52) U.S. Cl.
CPC .......... *C11B 9/0015* (2013.01); *C07C 69/734* (2013.01); *C11B 9/0019* (2013.01)

(58) Field of Classification Search
CPC ..... C11D 3/507; C11B 9/0015; C11B 9/0019; A61K 8/37; C07C 59/734; C07C 59/732
USPC ........................................... 512/27, 26, 25, 1
See application file for complete search history.

(56) References Cited

U.S. PATENT DOCUMENTS

2021/0115354 A1 4/2021 Womack et al.

FOREIGN PATENT DOCUMENTS

| | | | |
|---|---|---|---|
| IN | 142206 A | 6/1977 | |
| JP | S50137981 A | 11/1975 | |
| WO | WO-2019243501 A1 * | 12/2018 | ............ A61Q 13/00 |

OTHER PUBLICATIONS

Scheiner, Peter et al., C-1'-Branched Acyclovir Derivatives. Synthesis and Antiviral Evaluation, Nucleosides & Nucleotides, vol. 8, No. 8, 1989, pp. 1441-1451.

Registry (STN) [online], Nov. 16, 1984, Date of search: Apr. 11, 2025, CAS Registry Nos. 52398-50-2, 52398-52-4, 52478-91-8.

* cited by examiner

*Primary Examiner* — Jessica Whiteley

(57) ABSTRACT

The present invention relates to compounds of formula (I) as properfume compounds. In particular, the present invention relates to a method to release a compound being a carbonyl of formula (II), a formate ester of formula (III) and/or an alcohol of formula (IV), by exposing the compound of formula (I) to an environment wherein it is oxidized. Moreover, the present invention relates to a perfuming composition and a perfumed consumer product comprising at least one compound of formula (I).

20 Claims, No Drawings

ENOL ETHER PROPERFUME

This present application is a U.S. national phase entry under 35 U.S.C. § 371 of PCT Application No. PCT/EP2021/065606, filed Jun. 10, 2021, which claims priority to U.S. Provisional Application No. 63/038, 160, filed Jun. 12, 2020, and European Patent Application No. 20182200.4, filed Jun. 25, 2020. The entire contents of these applications are explicitly incorporated herein by this reference.

TECHNICAL FIELD

The present invention relates to compounds of formula (I) as properfume compounds. In particular, the present invention relates to a method to release a compound being a carbonyl of formula (II), a formate ester of formula (III) and/or an alcohol of formula (IV), by exposing the compound of formula (I) to an environment wherein it is oxidized. Moreover, the present invention relates to a perfuming composition and a perfumed consumer product comprising at least one compound of formula (I).

BACKGROUND

The perfume industry has a particular interest for compositions or additives which are capable of prolonging or enhancing the perfuming effect of at least one perfuming ingredient for a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients are unstable and need to be protected against slow degradation prior to their use. Long-lasting perfumes are desirable for various applications, as for example fine or functional perfumery or cosmetic preparations. The washing and softening of textiles are particular fields in which there is a constant need to enable the effect of active substances, in particular perfumes, or perfuming compositions, to be effective for a certain period of time after washing, softening and drying. Indeed, many active substances which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

WO 2019243501 discloses enol ether capable of efficiently releasing a carbonyl compound, a formate ester compound and an alcohol compound. However, said compounds, under acidic conditions, may be partly hydrolyzed after several days.

It has now been surprisingly found that enol ether compounds according to the present invention solve the above-mentioned problem by reducing the rate of hydrolysis while still being able of efficiently releasing a compound being a carbonyl of formula (II), a formate ester of formula (III) and/or an alcohol of formula (IV).

DETAILED DESCRIPTION

Olfaction is a complex and dynamic process and controlling the release profile of volatile fragrance compounds may maximize the impact of fragrance formulations and enrich the sensorial experience. Profragrances, such as the compounds of the present invention add a dimension of control and long-lastingness to the release profile of highly volatile perfumery raw materials (PRMs) while having better stability in acidic media.

Without intending to be limited to any particular theory, the compounds of the present invention may achieve their effect on the olfactive properties of a perfuming composition by tethering the PRM to a molecular anchor and requiring a specific reaction mechanism under certain environmental conditions to release the volatile PRM from this anchor. In the present invention, the release of one, two or up to three PRMs is prompted by oxidation when the profragrance is exposed to the oxygen in ambient air.

The first object of the present invention is a method to release from a precursor compound, compounds selected from the group consisting of a) a carbonyl compound of formula (II)

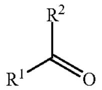

wherein $R^1$ is a $C_{1-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a hydroxy, $C_{1-15}$ alkyl, $C_{2-15}$ alkenyl, $C_{1-15}$ alkoxy, $C_{2-15}$ alkenyloxy, $C_{3-15}$ cycloalkyl, $C_{5-15}$ cycloalkenyl, $C_{3-15}$ heterocycloalkyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^2$ represents a hydrogen atom, a $C_{1-6}$ alkyl or phenyl group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

b) a formate ester of formula (III)

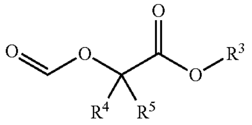

$R^3$ represents a hydrogen atom, a $C_{1-10}$ alkyl group, a $C_{3-10}$ alkenyl group, a benzyl group, a 2-phenylethyl group or a $C_{5-8}$ cycloalkyl group optionally substituted by one, two or three $C_{1-4}$ alkyl groups;

$R^4$ represents a hydrogen atom, a $C_{1-6}$ alkyl, a phenyl or a $CH_2C(O)OR^3$ group; wherein $R^3$ has the same meaning as defined above;

$R^5$ represents a hydrogen atom or a methyl group;

c) an alcohol of formula (IV)

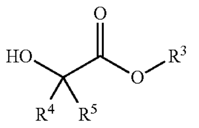

wherein $R^3$, $R^4$ and $R^5$ have the same meaning as defined above;

wherein the precursor compound comprises a compound of formula (I)

(I)

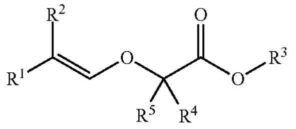

in the form of any one of its stereoisomers or a mixture thereof, and wherein $R^1$, $R^2$ and $R^3$, $R^4$ and $R^5$ have the same meaning as defined above;

by exposing the precursor compound of formula (I) to an environment wherein the compound is oxidized; i.e. ambient conditions.

According to any one of the embodiments of the invention, at least one of the compounds of formula (II), (III) or (IV) is an active compound.

The terms "active compound", "active volatile compound", "active volatile carbonyl, formate ester and/or alcohol" or the similar, are understood as carbonyl, formate ester and/or alcohol compounds being capable of bringing a benefit or effect into its surrounding environment. In particular, the "active compound" is selected from the group consisting of a perfuming ingredient, flavoring ingredient, malodor counteracting ingredient, antimicrobial ingredient and insect repellent or attractant ingredient. Therefore, to be considered as an "active compound" the compound has to possess at least one property which renders it useful as a perfuming ingredient, as a malodor counteracting ingredient, as a flavoring ingredient, as an antimicrobial ingredient and/or as an insect repellent or attractant.

The term "perfuming ingredient" is understood as a compound which is used as an active ingredient in perfuming preparations or compositions in order to impart a hedonic effect. In other words, a compound to be considered as being a perfuming ingredient, must be recognized by a skilled person in the art of perfumery as being able to impart or modify in a positive or pleasant way the odor of a composition, and not just as having an odor. The perfuming ingredient may impart an additional benefit beyond that of modifying or imparting an odor, such as long-lasting, blooming, malodour counteraction, antimicrobial effect, antiviral effect, microbial stability, or pest control. The term "flavoring ingredient" is understood to as being capable of imparting a taste sensation to the taster's pallet. The term "malodor counteracting ingredient" is understood as being capable of reducing the perception of malodor, i.e. of an odor that is unpleasant or offensive to the human nose. The term "antimicrobial ingredient" is understood as being capable of killing microorganism or reducing or preventing their growth and/or accumulation and include antibacterial, antibiotic, antifungal, antiviral and antiparasitic ingredients.

The term "insect attractant or repellent" is understood as a compound having a positive or negative effect on insects. Examples of insect attractant or repellent ingredients can be found in reference texts or in other works of a similar nature as for example: A. M. El-Sayed, The Pherobase 2005, http://www.pherobase.net.

According to the above and below mentioned embodiments of the invention, the method according to the present invention is particularly useful when the active compound is a perfuming ingredient, i.e. a perfuming carbonyl compound, formate ester and/or alcohol. A "perfuming carbonyl compound, formate ester and/or alcohol" is a compound, which is of use in the perfumery industry, i.e. a compound which is used as active ingredient in perfuming preparations or compositions in order to impart a hedonic effect. In other words, such a carbonyl compound, formate ester and/or alcohol, to be considered as being a perfuming one, must be recognized by a person skilled in the art of perfumery as being able to impart or modify in a positive or pleasant way the odor of a composition, and not just as having an odor. The perfuming carbonyl compound, formate ester and/or alcohol can be of natural or synthetic origin. Many of these perfuming carbonyl compounds, formate estesr and/or alcohols are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery.

Herein described, the terms "perfuming carbonyl compound, formate ester and/or alcohol" are also referred to as "perfuming compounds".

Practically, the invention is carried out exactly in the same manner, independently of the exact properties of the active carbonyl compound, formate ester or alcohol. Therefore, it is understood that, even if the invention will be further illustrated herein below with a specific reference to "perfuming compounds", the below embodiments are also applicable to other active carbonyl compound, formate ester and/or alcohol (i.e. it is possible to replace the expression "perfuming" with "flavoring", "malodor counteracting", "antibacterial", "antimicrobial", "insect attractant" or with "insect repellent" for instance).

The term "optionally" is understood that a certain group to be optionally substituted can or cannot be substituted with a certain functional group. The term "one or more" is understood as being substituted with 1 to 7, preferably 1 to 5 and more preferably 1 to 3 of a certain functional group.

The terms "alkyl" and "alkenyl" are understood as comprising branched and linear alkyl and alkenyl groups. The terms "alkenyl", "cycloalkenyl" and "heterocycloalkenyl" is understood as comprising 1, 2 or 3 olefinic double bonds, preferably 1 or 2 olefinic double bonds. The terms "cycloalkyl", "cycloalkenyl", "heterocycloalkyl", "heterocycloalkenyl" and "heterocyclic" are understood as comprising a monocyclic or fused, spiro and/or bridged bicyclic or tricyclic cycloalkyl, cycloalkenyl, heterocycloalkyl, heterocycloalkenyl and heterocyclic groups, preferably monocyclic cycloalkyl, cycloalkenyl, heterocycloalkyl and heterocycloalkenyl groups.

The term "carbonyl" designates an aldehyde or a ketone depending on the meaning of the $R^2$ group; i.e. the carbonyl compound of formula (II) is an aldehyde when $R^2$ represents a hydrogen atom or a ketone when $R^2$ represents a $C_{1-6}$ alkyl or phenyl group.

The term "aryl" is understood as comprising any group comprising at least one aromatic group such as phenyl, indenyl, indanyl, benzodioxolyl, dihydrobenzodioxinyl, tetrahydronaphthalenyl or naphthalenyl group.

For the sake of clarity, by the expression "any one of its stereoisomers or a mixture thereof", or the similar, it is meant the normal meaning understood by a person skilled in the art, i.e. that the compound of formula (I) can be a pure enantiomer or diastereomer. In other words, the compound of formula (I) may possess several stereocenters and each of said stereocenter can have two different stereochemistries (e.g. R or S). The compound of formula (I) may even be in the form of a pure enantiomer or in the form of a mixture of enantiomers or diastereoisomers. The compound of formula (I) can be in a racemic form or scalemic form. Therefore, the compound of formula (I) can be one stereoisomer or in the form of a composition of matter comprising, or consisting of, various stereoisomers.

According to any one of the above embodiments of the invention, said compound of formula (I) can be in the form of its E or Z isomer or of a mixture thereof, e.g. the invention comprises compositions of matter consisting of one or more compounds of formula (I), having the same chemical structure but differing by the configuration of the double bond. In particular, compound (I) can be in the form of a mixture consisting of isomers E and Z and wherein said isomers E represent at least 50% of the total mixture, or even at least 60%, or even at least 70%, or even at least 75% (i.e a mixture E/Z comprised between 75/25 and 100/0). Or, compound (I) can be in the form of a mixture consisting of isomers E and Z and wherein said isomers Z represent at least 50% of the total mixture, or even at least 60%, or even at least 70%, or even at least 75% (i.e a mixture E/Z comprised between 25/75 and 0/100), particularly when $R^2$ is an hydrogen atom.

According to any one of the embodiments of the invention, when $R^1$ may be a $C_{3-15}$ alkenyl, it is understood that the double bond is not adjacent to the carbon connecting $R^1$. In other words, compounds of formula (II) are not an enone and compounds of formula (I) are not a dienol ether.

According to a particular embodiment of the invention, $R^2$ may represent a hydrogen atom, a $C_{1-3}$ alkyl. Particularly, $R^2$ may represent a hydrogen atom, a methyl or an ethyl group. Even more particularly, $R^2$ may represent a hydrogen atom or a methyl group.

According to a particular embodiment of the invention, $R^1$ may represent a $C_{1-12}$ alkyl, $C_{3-12}$ alkenyl, $C_{6-10}$ aryl, $C_{3-12}$ cycloalkyl, $C_{5-12}$ cycloalkenyl or $C_{3-12}$ heterocycloalkyl group, each optionally substituted with one or more of a hydroxy, $C_{1-10}$ alkyl, $C_{2-10}$ alkenyl, $C_{1-10}$ alkoxy, $C_{2-10}$ alkenyloxy, $C_{3-10}$ cycloalkyl, $C_{5-10}$ cycloalkenyl, $C_{3-10}$ heterocycloalkyl $C_{6-10}$ aryl and/or $C_{6-10}$ aryloxy group, each optionally substituted with one or more of a $C_{1-6}$ alkyl, $C_{1-6}$ alkoxy and/or hydroxy group. Particularly, $R^1$ may represent a $C_{1-10}$ alkyl, $C_{3-10}$ alkenyl, $C_{3-11}$ cycloalkyl or $C_{5-11}$ cycloalkenyl group, each optionally substituted with one or more of a $C_{1-4}$ alkyl, $C_{1-4}$ alkoxy, $C_{3-8}$ cycloalkyl, $C_{5-8}$ cycloalkenyl, $C_6$ aryl and/or $C_6$ aryloxy group, each optionally substituted with one or more of a hydroxy, $C_{1-4}$ alkyl and/or $C_{1-4}$ alkoxy group. Particularly, $R^1$ may represent a $C_{1-10}$ alkyl or $C_{3-10}$ alkenyl group, each optionally substituted with one or more $C_{1-4}$ alkoxy, 4-methoxyphenyl and/or phenyl group. Even more particularly, $R^1$ may represent a nonyl, decyl, dec-9-en-1-yl, 4-phenylbutan-2-yl or phenylethyl group.

According to another particular embodiment of the invention, $R^1$ may represent a naphthyl group or a phenyl group optionally substituted by one or two $R^{1'}$ group wherein $R^{1'}$, simultaneously or independently, represents a hydroxy group, a $C_{1-3}$ alkyl group, a $C_{1-3}$ alkoxy group, a $R^aCOO$ group, a $R^aOCO$ group wherein $R^a$ is a hydrogen atom, a $C_{1-3}$ alkyl group, a $C_{2-3}$ alkenyl group, or two adjacent $R^{1'}$, when taken together, represent a —O—$(CH_2)_m$—O— wherein m is 1 or 2 or form a $C_{5-6}$ saturated or unsaturated ring. Particularly, $R^1$ may represent a naphtyl group or a phenyl group optionally substituted by one or two $R^1$, group wherein $R^{1'}$, simultaneously or independently, represents a hydroxy group, a $C_{1-3}$ alkyl group, a $C_{1-3}$ alkoxy group, or two adjacent $R^{1'}$, when taken together, represent a —O—$(CH_2)_m$—O— wherein m is 1 or 2 or form a $C_{5-6}$ saturated or unsaturated ring. Even more particularly, $R^1$ may represent a phenyl group, a naphthyl group, a 4-methoxyphenyl group or a 3,4-dimethoxyphenyl group.

According to a particular embodiment of the invention, $R^1$ and $R^2$, when taken together, may form a $C_{5-16}$ cycloalkyl or $C_{5-16}$ cycloalkenyl group, each optionally substituted with one or more of a $C_{1-8}$ alkyl, $C_{1-8}$ alkoxy, $C_{3-8}$ cycloalkyl, $C_{5-8}$ cycloalkenyl and/or phenyl group. Particularly, $R^1$ and $R^2$, when taken together, may form a $C_{5-8}$ cycloalkyl or $C_{5-8}$ cycloalkenyl group, each optionally substituted with one or more of a $C_{1-6}$ alkyl and/or $C_{1-3}$ alkoxy group. Even more particularly, $R^1$ and $R^2$, when taken together, may form a $C_{5-6}$ cycloalkyl, optionally substituted with one to three of a $C_{1-6}$ alkyl group.

According to any one of the embodiments of the invention, $R^3$ may represent a $C_{1-8}$ alkyl group, a $C_{3-8}$ alkenyl group, a benzyl group, a 2-phenylethyl group or a $C_{5-6}$ cycloalkyl group optionally substituted by one, two or three $C_{1-3}$ alkyl groups. Particularly, $R^3$ may represent a $C_{1-8}$ alkyl group, a $C_{3-8}$ alkenyl group or 2-isopropyl-5-methylcyclohexyl group. Particularly, $R^3$ may represent a $C_{1-8}$ alkyl or $C_{3-8}$ alkenyl group. Particularly, $R^3$ may represent a $C_{1-8}$ alkyl or $C_{3-6}$ alkenyl group. Even more particularly, $R^3$ may represent a methyl, a hexyl, an octyl, 2-phenylethyl, 2-butyl (i.e. sec-butyl), a 3-octyl or a hex-3-en-1-yl group.

According to any one of the embodiments of the invention, $R^4$ may represent a hydrogen atom, a $C_{1-3}$ alkyl or a phenyl group. Particularly, $R^4$ may represent a hydrogen atom or a $C_{1-3}$ alkyl group. Even more particularly, $R^4$ may represent a hydrogen atom or a methyl group.

According to any one of the embodiments of the invention, $R^5$ is a hydrogen atom or when $R^4$ is a methyl group, $R^5$ is a hydrogen atom or methyl group.

According to a particular embodiment, at least one of the compounds of formula (II), and (IV) are active compounds. Even more, the compound of formula (II) is active compound.

According to a particular embodiment, the carbonyl compound of formula (II) and/or the active alcohol of formula (IV) are perfuming ingredients. For a person skilled in the art it is also evident that compounds of formula (II), (III) and (IV) according to the present invention are inherently volatile compounds.

The carbonyl compound, formate ester and/or alcohol may be advantageously characterized by a vapor pressure above 1.0 Pa, as obtained by calculation using the software EPIwin v. 3.10 (2000, available at the US Environmental Protection Agency). According to another embodiment, the vapor pressure of the ketone, formate ester and/or alcohol may be above 5.0, or even above 7.0 Pa.

According to a particular embodiment, the compound of formula (I) is non-volatile. The compound of formula (I) may be advantageously characterized by a vapor pressure below 0.01 Pa, as obtained by calculation using the software EPIwin v. 3.10 (2000, available at the US Environmental Protection Agency). According to a preferred embodiment, the vapor pressure is below 0.001 Pa.

According to a particular embodiment, the carbonyl compound of formula (II) is a ketone selected from the group consisting of acetophenone, p-methylacetophenone, p-methoxyacetophenone, benzophenone, 1-(5,6,7,8-tetrahydronaphthalen-2-yl)ethan-1-one, 1-(naphthalen-2-yl)ethan-1-one, 1-(naphthalen-1-yl)ethan-1-one, 1-(p-tolyl)propan-1-one, 1-(1,1,2,3,3,6-hexamethyl-2,3-dihydro-1H-inden-5-yl)ethan-1-one, 1-(3,5,5,6,8,8-hexamethyl-5,6,7,8-tetrahydronaphthalen-2-yl)ethan-1-one, 2,3,3-trimethyl-2,3-dihydro-1H-inden-1-one, 1-(3-isopropyl-1,1,2,6-tetramethyl-2,3-dihydro-1H-inden-5-yl)ethan-1-one, 1-(6-(tert-butyl)-1,1-dimethyl-2,3-dihydro-1H-inden-4-yl)ethan-1-one, acetone, 3-hexanone, 4-nonanone, 5-undecanone, cyclohexanone, cyclopentanone, cyclooctanone, cycloheptanone, cyclooctanone, cyclodecanone, 2-butanone, 2-pentanone, 2-hexanone, 2-heptanone, 2-octanone, 2-nonanone, 2-decanone, 2-undecanone, 2-tridecanone, 2-pentadecanone, 3-heptanone, 3-octanone, 5-methyl-3-heptanone, 6-methyl-5-hepten-2-one, 2,6-dimethyl-7-octen-4-one, 2-(sec-butyl)cyclohexan-1-one, 2-(tert-butyl)cyclohexan-1-one, 4-(tert-butyl)cyclohexan-1-one, 4-(tert-pentyl)cyclohexan-1-one, 5-isopropyl-2-methylcyclohexan-1-one, 2-isopropyl-5-methylcyclohexan-1-one, 2,2,6-trimethylcyclohexan-1-one, 2,2,4-trimethylbicyclo[3.1.1]heptan-3-one, thujnone, 2-ethyl-4,4-dimethylcyclohexan-1-one, 1,7,7-trimethylbicyclo[2.2.1]heptan-2-one, plicatone, thujopsan-4-one, 1,3,3-trimethylbicyclo[2.2.1]heptan-2-one, 4-phenyl-2-butanone, 4-(4-methoxyphenyl)-2-butanone, zingerone, 4-(1,3-benzodioxol-5-yl)-2-butanone, 2-cyclohexyl-4-methyl-2-pentanone, 1-(4-methyl-1-phenoxy)-2-propanone, 4-(2,6,6-trimethylcyclohex-2-en-1-yl)butan-2-one, 4-(2,6,6-trimethylcyclohex-1-en-1-yl)butan-2-one, (5-E/Z)-6,10-dimethylundeca-5,9-dien-2-one, cyclopentadecanone, (Z)-cycloheptadec-9-en-1-one, 3-methylcyclopentadecan-1-one, 3-methyl-5-cyclopentadec en-1-one, (Z)-cyclopentadec-4-en-1-one, 4,8-cyclododecadien-1-one, 7-methyl-2H-benzo[b][1,4]dioxepin-3(4H)-one, 7-propyl-2H-benzo[b][1,4]dioxepin-3(4H)-one, 1-(5-propylbenzo[d][1,3]dioxol-2-yl)ethan-1-one, 4,4a,6,7,8,8a-hexahydro-1,4-methanonaphthalen-5(1H)-one, 2-pentylcyclopentan-1-one, 2-hexylcyclopentan-1-one, 2-heptylcyclopentan-1-one, 2-(hex-5-en-1-yl)cyclopentan-1-one, 2,2,5-trimethyl-5-pentylcyclopentan-1-one, Iso-E-Super, 1-(5-isopropyl-2-methylcyclohex-2-en-1-yl)propan-1-one, 2,2,7,9-tetramethylspiro[5.5]undec-7-en-1-one, 1-(naphthalen-2-yl)ethan-1-one, 4-ethyl-8-methyloctahydronaphthalen-1 (2H)-one, 1-(3,3-dimethylcyclohexyl)ethan-1-one, 2,6,6-trimethylcycloheptan-1-one, 3,6,8,8-tetramethylhexahydro-1H-3a,7-methanoazulen-5 (4H)-one, methyl 2-(3-oxo-2-pentylcyclopentyl)acetate, 4-(4-hydroxyphenyl)butan-2-one and 1-(4-methoxyphenyl)propan-2-one.

Particularly, the carbonyl compound of formula (II) is a ketone selected from the group consisting of acetophenone, p-methylacetophenone, p-methoxyacetophenone, 1-(naphthalen-2-yl)ethan-1-one, 2,3,3-trimethyl-2,3-dihydro-1H-inden-1-one, 2-nonanone, 2-decanone, 2-undecanone, 4-phenyl-2-butanone, 4-(4-methoxyphenyl)-2-butanone, 4-(tert-pentyl)cyclohexan-1-one, 4-(1,3-benzodioxol-5-yl)-2-butanone, 4-(2,6,6-trimethylcyclohex-2-en-1-yl)butan-2-one (dihydro-alpha-ionone), 4-(2,6,6-trimethylcyclohex-1-en-1-yl)butan-2-one, 2-pentylcyclopentan-1-one, 2-hexylcyclopentan-1-one, 2-heptylcyclopentan-1-one, 3-methylcyclopentadecan-1-one, cyclopentadecanone, 2,2,6-trimethylcyclohexanone, (4E/Z, 8E/Z)-cyclododeca-4,8-dien-1-one, 2-(2-(4-methylcyclohex-3-en-1-yl)propyl)cyclopentan-1-one, 2-isopropyl-5-methylcyclohexan-1-one, 7-methyloctahydro-1,4-methanonaphthalen-6(2H)-one, 2-ethyl-4,4-dimethylcyclohexan-1-one, 2-(hex-5-en-1-yl)cyclopentan-1-one, 1-(4-methoxyphenyl)propan-2-one and 2-(sec-butyl)cyclohexan-1-one.

According to a particular embodiment, the carbonyl compound of formula (II) is an aldehyde selected from the group consisting of benzaldehyde, 4-methylbenzaldehyde, 4-ethylbenzaldehyde, 4-isopropylbenzaldehyde, 4-(tert-butyl)benzaldehyde, 4-methoxybenzaldehyde, 3,4-dimethoxybenzaldehyde, benzo[d][1,3]dioxole-5-carbaldehyde (heliotropin), vanillin, 3-ethoxy-4-hydroxybenzaldehyde, 2-hydroxy-4-methoxybenzaldehyde 4-formyl-2-methoxylphenyl acetate, 4-formyl-2-methoxyphenyl isobutyrate, 3,5,5,6,7,8,8-heptamethyl-5,6,7,8-tetrahydronaphthalene-2-carbaldehyde, hexanal, heptanal, octanal, nonanal, decanal, undecanal, dodecanal, 2-ethylhexanal, 3,7-dimethyloctanal, 2-methyldecanal, 2-methylundecanal, 6-nonenal, 4-decenal, 5-octenal, 8-nonenal, 8-decenal, 9-decenal, 3-(3,3-dimethyl-2,3-dihydro-1H-inden-5-yl)propanal, 9-undecenal, 10-undecenal, 3-(6,6-dimethylbicyclo[3.1.1]hept-2-en-2-yl)propanal, 4-dodecenal, 8-isopropyl-6-methylbicyclo[2.2.2]oct-5-ene-2-carbaldehyde, 3-(4-(tert-butyl)phenyl)propanal, 3-(4-(tert-butyl)phenyl)-2-methylpropanal, 2-methyl-4-phenylbutanal, 3-methyl-5-phenylpentanal, 4-(4-hydroxy-4-methylpentyl)cyclohex-3-ene-1-carbaldehyde, 2,4-dimethylcyclohex-3-ene-1-carbaldehyde, 3-phenylbutanal, 2,6-dimethylhept-5-enal, 3-(4-methylcyclohex-3-en-1-yl)butanal, 3-(4,4-dimethylcyclohex-1-en-1-yl)propanal, 4-methyl-5-(p-tolyl)pent-4-enal, 3,7-dimethyloct-6-enal, 2-phenylpropanal, phenylacetaldehyde, 3-(benzo[d][1,3]dioxol-5-yl)-2-methylpropanal, 5-methoxyoctahydro-1H-4,7-methanoindene-1-carbaldehyde, 6-methoxyoctahydro-1H-4,7-methanoindene-1-carbaldehyde, 3-(3-isopropylphenyl)butanal, 3-(4-isobutyl-2-methylphenyl)propanal, 3,6-dimethylcyclohex-3-ene-1-carbaldehyde, 2-((3,7-dimethyloct-6-en-1-yl)oxy)acetaldehyde, 3-(4-ethylphenyl)-2,2-dimethylpropanal, 3,5,6-trimethylcyclohex-3-ene-1-carbaldehyde, 4-(4-methylpent-3-en-1-yl)cyclohex-3-ene-1-carbaldehyde, 3-phenylpropanal, 3-(4-isopropylphenyl)-2-methylpropanal, 8,8-dimethyl-1,2,3,4,6,7,8,8a-octahydronaphthalene-2-carbaldehyde, 2-methyl-4-(2,2,3-trimethylcyclopent-3-en-1-yl)pent-4-enal), 3,5,5-trimethylhexanal, 2,6,10-trimethyl-9-undecenal, 3-(4-methoxyphenyl)-2-methylpropanal, 7-hydroxy-3,7-dimethyloctanal, 3-(4-isopropylphenyl)propanal, 2-(4-isopropylphenyl)acetaldehyde, 6-methoxy-2,6-dimethylheptanal, 3-(4-isopropylcyclohex-1-en-1-yl)propanal, 3-(4-isopropylcyclohexylidene)propanal, 3-(3-isopropylcyclohex-1-en-1-yl)propanal and 3-(5-isopropylcyclohex-1-en-1-yl)propanal Particularly, the carbonyl compound of formula (II) is an aldehyde selected from the group consisting of octanal, nonanal, decanal, undecanal, dodecanal, benzaldehyde, 4-methoxybenaldehyde, 3,4-dimethoxybenzaldehyde, benzo[d][1,3]dioxole-5-carbaldehyde, vanillin, 4-formyl-2-methoxylphenyl acetate, 2-methyldecanal, 2-methylundecanal, 2-phenylpropanal, 2-methyl-4-phenylbutanal, 2-(4-isopropylphenyl)acetaldehyde, phenylacetaldehyde, 4-dodecenal, 9-undecenal, 10-undecenal, 9-decenal, 8-decenal, 3-phenylbutanal, 3-(4,4-dimethylcyclohex-1-en-1-yl)propanal, 4-(4-methylpent-3-en-1-yl)cyclohex-3-ene-1-carbaldehyde and 3,7-dimethyloct-6-enal.

According to a particular embodiment, the formate ester of formula (III) are selected from the group consisting of methyl 2-(formyloxy)acetate, ethyl 2-(formyloxy)acetate, propyl 2-(formyloxy)acetate, isopropyl 2-(formyloxy)acetate, butyl 2-(formyloxy)acetate, pentyl 2-(formyloxy)acetate, hexyl 2-(formyloxy)acetate, hex-3-en-1-yl 2-(formyloxy)acetate, octyl 2-(formyloxy)acetate, octan-3-yl 2-(formyloxy)acetate, phenethyl 2-(formyloxy)acetate, benzyl 2-(formyloxy)acetate, methyl 2-(formyloxy)propanoate, ethyl 2-(formyloxy)propanoate, propyl 2-(formyloxy)propanoate, isopropyl 2-(formyloxy)propanoate, butyl 2-(formyloxy)propanoate, sec-butyl 2-(formyloxy)propanoate, pentyl 2-(formyloxy)propanoate hexyl 2-(formyloxy) propanoate, hex-3-en-1-yl 2-(formyloxy)propanoate, octyl 2-(formyloxy)propanoate, octan-3-yl 2-(formyloxy)propanoate, phenethyl 2-(formyloxy)propanoate, 3,7-dimethyloct-6-en-1-yl 2-(formyloxy)propanoate, 2-isopropyl-5-methylcyclohexyl 2-(formyloxy)propanoate, benzyl 2-(formyloxy)propanoate, methyl 2-(formyloxy)-2-methylpropanoate, ethyl 2-(formyloxy)-2-methylpropanoate, propyl 2-(formyloxy)-2-methylpropanoate, butyl 2-(formyloxy)-2-methylpropanoate, hexyl 2-(formyloxy)-2-methylpropanoate, hex-3-en-1-yl 2-(formyloxy)-2-methylpropanoate, methyl 2-(formyloxy)-2-phenylacetate, ethyl 2-(formyloxy)-2-phenylacetate, dimethyl 2-(formyloxy)succinate and diethyl 2-(formyloxy)succinate.

According to a particular embodiment, the alcohol of formula (IV) is selected from the group consisting of methyl 2-hydroxypropanoate, ethyl 2-hydroxypropanoate, propyl 2-hydroxypropanoate, butyl 2-hydroxypropanoate, sec-butyl 2-hydroxypropanoate, isopropyl 2-hydroxypropanoate, octyl 2-hydroxypropanoate, octan-3-yl 2-hydroxypropanoate, hexyl 2-hydroxypropanoate, hex-3-en-1-yl 2-hydroxypropanoate, 3,7-dimethyloct-6-en-1-yl 2-hydroxypropanoate, phenethyl 2-hydroxypropanoate, benzyl 2-hydroxypropanoate, 2-isopropyl-5-methylcyclohexyl 2-hydroxypropanoate, methyl 2-hydroxy-2-methylpropanoate, ethyl 2-hydroxy-2-methylpropanoate, propyl 2-hydroxy-2-methylpropanoate, butyl 2-hydroxy-2-methylpropanoate, hexyl 2-hydroxy-2-methylpropanoate, methyl glycolate, ethyl glycolate, butyl glycolate, hexyl glycolate, methyl 2-hydroxy-2-phenylacetate, ethyl 2-hydroxy-2-phenylacetate dimethyl 2-hydroxysuccinate and diethyl 2-hydroxysuccinate.

According to a particular embodiment, the compound of formula (I) is selected from the group consisting of methyl 2-((2-methylundec-1-en-1-yl)oxy)acetate, methyl 2-((2 methylundec-1-en-1-yl)oxy)propanoate, methyl 2-methyl-2-((2-methylundec-1-en-1-yl)oxy)propanoate, methyl 2-((2-methyl-4-phenylbut-1-en-1-yl)oxy)propanoate, octyl 2-((2-methylundec-1-en-1-yl)oxy)propanoate, hex-3-en-1-yl 2-((2-methylundec-1-en-1-yl)oxy)propanoate, methyl 2-(dodec-1-en-1-yloxy)propanoate, methyl 2-((3-methyl-5-phenylpent-1-en-1-yl)oxy)propanoate, methyl 2-(styryloxy) propanoate, methyl 2-methyl-2-(styryloxy)propanoate, methyl 2-((2-phenylprop-1-en-1-yl)oxy)propanoate, hexyl-2-((2-phenylprop-1-en-1-yl)oxy)propanoate, hex-3-en-1-yl 2-((2-phenylprop-1-en-1-yl)oxy)propanoate, methyl 2-((2-methyldec-1-en-1-yl)oxy), methyl 2-((3-(4-methoxyphenyl)-2-methylprop-1-en-1-yl)oxy)propanoate, methyl 2-((2-ethylhex-1-en-1-yl)oxy)propanoate, methyl 2-((4-(4-methoxyphenyl)-2-methylbut-1-en-1-yl)oxy)propanoate, methyl 2-((2-pentylcyclopentylidene)methoxy)propanoate, methyl 2-((2-ethyl-4,4-dimethylcyclohexylidene)methoxy) propanoate, methyl 2-((2-(4-methoxyphenyl)prop-1-en-1-yl)oxy)propanoate, methyl 2-((2-(naphthalen-2-yl)prop-1-en-1-yl)oxy)propanoate, methyl 2-((2-(p-tolyl)prop-1-en-1-yl)oxy)propanoate, methyl 2-methyl-2-((2-methyldec-1-en-1-yl)oxy)propanoate, methyl 2-((3-(4-methoxyphenyl)-2-methylprop-1-en-1-yl)oxy)-2-methylpropanoate, methyl 2-methyl-2-((2-phenylprop-1-en-1-yl)oxy)propanoate, methyl 2-methyl-2-((2-methyl-4-phenylbut-1-en-1-yl)oxy) propanoate, methyl 2-((2-(4-methoxyphenyl)prop-1-en-1-yl)oxy)-2-methylpropanoate, methyl 2-methyl-2-((2-(p-tolyl)prop-1-en-1-yl)oxy)propanoate, methyl 2-methyl-2-((2-pentylcyclopentylidene)methoxy)propanoate, methyl 2-(undeca-1,10-dien-1-yloxy)propanoate, methyl 2-(tridec-1-en-1-yloxy)propanoate, methyl 2-(dodeca-1,11-dien-1-yloxy)propanoate, methyl 2-((3-methyldodec-1-en-1-yl) oxy)propanoate, methyl 2-((4-phenylpent-1-en-1-yl)oxy) propanoate, methyl 2-((4-methoxystyryl)oxy)propanoate, methyl 2 ((3,4-dimethoxy styryl)oxy)propanoate, methyl 2-methyl-2-(tridec-1-en-1-yloxy)propanoate, methyl 2-methyl-2-((3-methyldodec-1-en-1-yl)oxy)propanoate, methyl 2-methyl-2-(tridec-1-en-1-yloxy)propanoate, phenethyl 2-(styryloxy)propanoate, (Z)-hex-3-en-1-yl 2-(styryloxy)propanoate, octan-3-yl 2-(styryloxy)propanoate, (Z)-hex-3-en-1-yl 2-((4-methoxystyryl)oxy)propanoate, phenethyl 2-((2-phenylprop-1-en-1-yl)oxy)propanoate, octan-3-yl 2-((2-phenylprop-1-en-1-yl)oxy)propanoate, phenethyl 2-((2-(p-tolyl)prop-1-en-1-yl)oxy)propanoate, sec-butyl 2-((2-(p-tolyl)prop-1-en-1-yl)oxy)propanoate, (Z)-hex-3-en-1-yl 2-((2-(4-methoxyphenyl)prop-1-en-1-yl) oxy)propanoate, phenethyl 2-((2-(4-methoxyphenyl)prop-1-en-1-yl)oxy)propanoate, sec-butyl 2-((2-(4-methoxyphenyl) prop-1-en-1-yl)oxy)propanoate, phenethyl 2-((2-(naphthalen-2-yl)vinyl)oxy)propanoate, 2-isopropyl-5-methylcyclohexyl 2-((2-methylundec-1-en-1-yl)oxy) propanoate, 3,7-dimethyloct-6-en-1-yl 2-((2-methylundec-1-en-1-yl)oxy)propanoate, ethyl 2-((2-pentylcyclopentylidene)methoxy)propanoate, (Z)-hex-3-en-1-yl 2-((2-pentylcyclopentylidene)methoxy)propanoate, methyl 2-((2-heptylcyclopentylidene)methoxy)propanoate, methyl 2-(non-1-en-1-yloxy)propanoate, methyl 2-(undec-1-en-1-yloxy)propanoate, (Z)-hex-3-en-1-yl 2-(dodec-1-en-1-yloxy)propanoate, methyl 2-(dodec-1-en-1-yloxy)-2-methylpropanoate, methyl 2-methyl-2-(undec-1-en-1-yloxy) propanoate, methyl 2-methyl-2-((3-phenylprop-1-en-1-yl) oxy)propanoate, methyl 2-methyl-2-((2-(naphthalen-2-yl) prop-1-en-1-yl)oxy)propanoate, methyl 2-((4-hydroxy-3-methoxystyryl)oxy)-2-methylpropanoate, hexyl 2-((4-hydroxy-3-methoxystyryl)oxy)-2-methylpropanoate, octyl 2-((4-hydroxy-3-methoxystyryl)oxy)-2-methylpropanoate, methyl 2-((3,4-dimethoxystyryl)oxy)-2-methylpropanoate, methyl 2-((4-acetoxy-3-methoxystyryl)oxy)-2-methylpropanoate, methyl 2-methyl-2-((3-methylundec-1-en-1-yl) oxy)propanoate, (Z)-hex-3-en-1-yl 2-((3-methyldodec-1-en-1-yl)oxy)propanoate, methyl 2-(dodeca-1,10-dien-1-yloxy) propanoate, methyl 2-(dodeca-1,10-dien-1-yloxy)-2-methylpropanoate methyl 2-methyl-2-((3-methyl-5-phenylpent-1-en-1-yl)oxy)propanoate, methyl 2-((2-(benzo [d][1,3]dioxol-5-yl)vinyl)oxy)-2-methylpropanoate and methyl 2-((4-methoxystyryl)oxy)-2-methylpropanoate.

According to any one of the above embodiments, the carbonyl compound of formula (II), the formate ester of formula (III) and the alcohol of formula (IV) are released from the precursor compound of formula (I) via oxidation of the precursor compound of formula (I) under ambient conditions. Even more, the precursor compound of formula (I) is oxidized under ambient conditions and in absence of any catalyst. For the sake of clarity, by the expression "ambient conditions", or the similar, it is meant the normal meaning understood by a person skilled in the art, i.e. the oxidation occurs at room temperature, under air and atmospheric pressure. In other words, the environment wherein the compound is oxidized is air. Herewith it is understood, that the compound of formula (I) is oxidized in ambient air. In particular, it is understood that the compound of formula (I) does not require a pure oxygen environment, heat or catalyst to be oxidized.

Without intending to be limited to any particular theory, the rate at which the precursor compound of formula (I) is oxidized may be greater than, equal to, or slower than the evaporation rates of the individual carbonyl compound of formula (II), the formate esters of formula (III) or the alcohols of formula (IV).

In some embodiments, the rate at which the precursor compound of formula (I) is oxidized, and thereby, the rate at which the individual carbonyl compound of formula (II), the formate esters of formula (III) or the alcohols of formula (IV) are released intensifies or prolongs the diffusion effect, and/or perception of the characteristic fragrance of at least one carbonyl compound formula (II), of at least one formate ester of formula (III) and/or of at least one alcohol of formula (IV) as defined above.

In one embodiment, 100% of the compound of formula (I) is oxidized in ambient air in a period of time ranging from 24 to 48 hours. Alternatively, 90% of the compound of formula (I) is oxidized in ambient air in a period of time ranging from 24 to 48 hours. Alternatively, 80% of the compound of formula (I) is oxidized in ambient air in a period of time ranging from 24 to 48 hours. Alternatively, 70% of the compound of formula (I) is oxidized in ambient air in a period of time ranging from 24 to 48 hours. Alternatively, 60% of the compound of formula (I) is oxidized in ambient air in a period of time ranging from 24 to 48 hours. Alternatively, 50% of the compound of formula (I) is oxidized in ambient air in a period of time ranging from 24 to 48 hours. Alternatively, 40% of the compound of formula (I) is oxidized in ambient air in a period of time ranging from 24 to 48 hours. Alternatively, 30% of the compound of formula (I) is oxidized in ambient air in a period of time ranging from 24 to 48 hours. Alternatively, 20% of the compound of formula (I) is oxidized in ambient air in a period of time ranging from 24 to 48 hours. Alternatively, 10% of the compound of formula (I) is oxidized in ambient air in a period of time ranging from 24 to 48 hours. Alternatively, 9% of the compound of formula (I) is oxidized in ambient air in a period of time ranging from 24 to 48 hours. Alternatively, 8% of the compound of formula (I) is oxidized in ambient air in a period of time ranging from 24 to 48 hours. Alternatively, 7% of the compound of formula (I) is oxidized in ambient air in a period of time ranging from 24 to 48 hours. Alternatively, 6% of the compound of formula (I) is oxidized in ambient air in a period of time ranging from 24 to 48 hours. Alternatively, 5% of the compound of formula (I) is oxidized in ambient air in a period of time ranging from 24 to 48 hours. Alternatively, 4% of the compound of formula (I) is oxidized in ambient air in a period of time ranging from 24 to 48 hours. Alternatively, 3% of the compound of formula (I) is oxidized in ambient air in a period of time ranging from 24 to 48 hours. Alternatively, 2% of the compound of formula (I) is oxidized in ambient air in a period of time ranging from 24 to 48 hours. Alternatively, 1% of the compound of formula (I) is oxidized in ambient air in a period of time ranging from 24 to 48 hours.

The present invention also relates to a microcapsule comprising at least one compound of formula (I). In one embodiment, the at least one compound of formula (I) is encapsulated in a core-shell microcapsule wherein the at least one compound of formula (I) is contained in the core surrounded by the shell. In one embodiment, the shell of the microcapsule protects the compound of formula (I) from the environment. The shell is made of material which is able to release the at least one compound of formula (I) and/or the compound of formulas (II), (III) and/or (IV). In one embodiment, the shell is made of material which is able to release the compound of formula (I) and/or the compound of formulas (II), (III) and/or (IV) upon breakage of the shell and/or by diffusion through the shell. A person skilled in the art is well aware of processes to prepare said microcapsules. So, microcapsule comprising at least one compound of formula (I) is one object of the present invention.

In a preferred embodiment, encapsulation of a compound of formula (I) may provide an environment within the capsule wherein all, or a portion of the compound of formula (I) may oxidize, thereby releasing the individual ketone of formula (II), the formate esters of formula (III) or the alcohols of formula (IV) into the capsule. In a preferred embodiment, the shell of the microcapsule may act as a permeability barrier, preventing the leakage of the individual carbonyl compound of formula (II), the formate esters of formula (III) or the alcohols of formula (IV) from the capsule.

According to a particular embodiment, the shell of the microcapsule comprises a material selected from the group consisting of polyurea, polyurethane, polyamide, polyester, poly(meth)acrylate (i.e. polyacrylate and/or polymethacrylate), polysiloxane, polycarbonate, polysulfonamide, polymers of urea and formaldehyde, melamine and formaldehyde, melamine and urea, or melamine and glyoxal and mixtures thereof. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to a particular embodiment, the core-shell microcapsule(s) can be also derived by using different or more than one encapsulation method.

In a preferred embodiment, the shell of the microcapsules may be, each independently, selected from the group of aminoplast, polyamide, polyester, polyurea and polyurethane shells and mixtures thereof.

In a particular embodiment, the shell of the microcapsules comprises an aminoplast copolymer, such as melamine-formaldehyde or urea-formaldehyde or cross-linked melamine formaldehyde or melamine glyoxal.

In a particular embodiment, the shell of the microcapsules is polyurea-based made from, for example but not limited to isocyanate-based monomers and amine-containing cross-linkers such as guanidine carbonate and/or guanazole. Certain polyurea microcapsules comprise a polyurea wall which is the reaction product of the polymerisation between at least one polyisocyanate comprising at least two isocyanate functional groups and at least one reactant selected from the group consisting of an amine (for example a water-soluble guanidine salt and guanidine); a colloidal stabilizer or emulsifier; and an encapsulated perfume. However, the use of an amine can be omitted.

In a particular embodiment, the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). In a particular embodiment, the emulsifier is an anionic or amphiphilic biopolymer, which may be for example chosen from the group consisting of gum Arabic, soy protein, gelatin, sodium caseinate and mixtures thereof.

In a particular embodiment, the shell of the microcapsules is polyurethane-based made from, for example but not limited to polyisocyanate and polyols, polyamide, polyester, etc.

In a particular embodiment, the microcapsules have a polymeric shell resulting from complex coacervation wherein the shell is possibly cross-linked.

In a particular embodiment of the core-shell microcapsules, the core-shell microcapsules comprise an oil-based core comprising a hydrophobic active, preferably at least one compound of formula(I), and a composite shell comprising a first material and a second material, wherein the first material and the second material are different, the first material is a coacervate, the second material is a polymeric material.

In a particular embodiment, the weight ratio between the first material and the second material is comprised between 50:50 and 99.9:0.1.

In a particular embodiment, the coacervate comprises a first polyelectrolyte, preferably selected among proteins (such as gelatin), polypeptides or polysaccharides (such as chitosan), most preferably Gelatin and a second polyelectrolyte, preferably alginate salts, cellulose derivatives guar gum, pectinate salts, carrageenan, polyacrylic and methacrylic acid or xanthan gum, or yet plant gums such as acacia gum (Gum Arabic), most preferably Gum Arabic.

The coacervate first material can be hardened chemically using a suitable cross-linker such as glutaraldehyde, glyoxal, formaldehyde, tannic acid or genipin or can be hardened enzymatically using an enzyme such as transglutaminase.

The second polymeric material can be selected from the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof, preferably polyurea and/or polyurethane. The second material is preferably present in an amount less than 3 wt. %, preferably less than 1 wt. % based on the total weight of the microcapsule slurry.

The preparation of an aqueous dispersion/slurry of core-shell microcapsules is well known by a skilled person in the art. In a particular embodiment, the microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

In a particular embodiment of the core-shell microcapsules, the core-shell microcapsules comprises

- an oil-based core comprising a hydrophobic active, preferably comprising at least one compound of formula (I),
- optionally an inner shell made of a polymerized polyfunctional monomer;
- a biopolymer shell comprising a protein, wherein at least one protein is cross-linked.

According to a particular embodiment, the protein is chosen in the group consisting of milk proteins, caseinate salts such as sodium caseinate or calcium caseinate, casein, whey protein, hydrolyzed proteins, gelatins, gluten, pea protein, soy protein, silk protein and mixtures thereof, preferably sodium caseinate, most preferably sodium caseinate According to a particular embodiment, the protein comprises sodium caseinate and a globular protein, preferably chosen in the group consisting of whey protein, beta-lactoglobulin, ovalbumine, bovine serum albumin, vegetable proteins, and mixtures thereof.

The protein is preferably a mixture of sodium caseinate and whey protein.

According to a particular embodiment, the biopolymer shell comprises a crosslinked protein chosen in the group consisting of sodium caseinate and/or whey protein.

According to a particular embodiment, the microcapsules slurry comprises at least one microcapsule made of:

- an oil-based core comprising the hydrophobic active, preferably comprising at least one compound of formula (I);
- an inner shell made of a polymerized polyfunctional monomer; preferably a polyisocyanate having at least two isocyanate functional groups
- a biopolymer shell comprising a protein, wherein at least one protein is cross-linked; wherein the protein contains preferably a mixture comprising sodium caseinate and a globular protein, preferably whey protein.
- optionally at least an outer mineral layer.

According to an embodiment, sodium caseinate and/or whey protein is (are) cross-linked protein(s).

The weight ratio between sodium caseinate and whey protein is preferably comprised between 0.01 and 100, preferably between 0.1 and 10, more preferably between 0.2 and 5.

In a particular embodiment, the microcapsules is a one-shell aminoplast core-shell microcapsule obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) preparing an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain the dried core-shell microcapsule.

In a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together:
    a. a polyamine component in the form of melamine or of a mixture of melamine and at least one $C_1$-$C_4$ compound comprising two $NH_2$ functional groups;
    b. an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
    c. a protic acid catalyst;

2) preparing an oil-in-water dispersion, wherein the droplet size is comprised between 1 and 600 microns, and comprising:

a. an oil;

b. a water medium:

c. at least an oligomeric composition as obtained in step 1;

d. at least a cross-linker selected amongst:

i. $C_4$-$C_{12}$ aromatic or aliphatic di- or tri-isocyanates and their biurets, triurets, trimmers, trimethylol propane-adduct and mixtures thereof; and/or ii. a di- or tri-oxiran compounds of formula:

Q-(oxiran-2-ylmethyl)$_n$ wherein n stands for 2 or 3 and Q represents a $C_2$-$C_6$ group optionally comprising from 2 to 6 nitrogen and/or oxygen atoms;

e. optionally a $C_1$-$C_4$ compounds comprising two $NH_2$ functional groups;

3) Heating the dispersion; and

4) Cooling the dispersion.

The above process is described in more details in WO 2013/068255.

In a particular embodiment of the core-shell microcapsules, the core-shell microcapsule is a polyamide core-shell polyamide microcapsule comprising:

an oil based core comprising an hydrophobic active, preferably comprising at least one compound of formula (I), and a polyamide shell comprising or being obtainable from:

an acyl chloride, a first amino compound, and a second amino compound.

According to a particular embodiment, the polyamide core-shell microcapsule comprises:

an oil based core comprising an hydrophobic active, preferably comprising at least one compound of formula (I), and a polyamide shell comprising or being obtainable from:

an acyl chloride, preferably in an amount comprised between 5 and 98%, preferably between 20 and 98%, more preferably between 30 and 85% w/w a first amino compound, preferably in an amount comprised between 1% and 50% w/w, preferably between 7 and 40% w/w;

a second amino compound, preferably in an amount comprised between 1% and 50% w/w, preferably between 2 and 25% w/w a stabilizer, preferably a biopolymer, preferably in an amount comprised between 0 and 90%, preferably between 0.1 and 75%, more preferably between 1 and 70%.

According to a particular embodiment, the polyamide core-shell microcapsule comprises:

an oil based core comprising a hydrophobic active, preferably comprising at least one compound of formula (I), and a polyamide shell comprising or being obtainable from:

an acyl chloride, a first amino-compound being an amino-acid, preferably chosen in the group consisting of L-Lysine, L-Arginine, L-Histidine, L-Tryptophane and/or mixture thereof.

a second amino compound chosen in the group consisting of ethylene diamine, diethylene triamine, cystamine and/or mixture thereof, and a biopolymer chosen in the group consisting of casein, sodium caseinate, bovin serum albumin, whey protein, and/or mixture thereof.

The first amino-compound can be different from the second amino-compound.

Typically, a process for preparing a polyamide-based microcapsule includes the following steps:

a) Dissolving at least one acyl chloride in a hydrophobic material, preferably a perfume to form an oil phase;

b) Dispersing the oil phase obtained in step a) into a water phase comprising a first amino compound to form an oil-in water emulsion;

c) Performing a curing step to form polyamide microcapsules in the form of a slurry;

wherein a stabilizer is added in the oil phase and/or in the water phase, and wherein at least a second amino-compound is added in the water phase before the formation of the oil-in-water emulsion and/or in the oil-in water emulsion obtained after step b).

In a particular embodiment, the shell of the microcapsule is polyurea- or polyurethane-based. Examples of processes for the preparation of polyurea and polyureathane-based microcapsule slurry are for instance described in WO 2007/004166, EP 2300146, and EP 2579976. Typically a process for the preparation of polyurea or polyurethane-based microcapsule slurry include the following steps:

a) Dissolving at least one polyisocyanate having at least two isocyanate groups in an oil to form an oil phase;

b) Preparing an aqueous solution of an emulsifier or colloidal stabilizer to form a water phase;

c) Adding the oil phase to the water phase to form an oil-in-water dispersion, wherein the mean droplet size is comprised between 1 and 500 μm, preferably between 5 and 50 μm; and d) Applying conditions sufficient to induce interfacial polymerisation and form microcapsules in form of a slurry.

In a particular embodiment, the microcapsule can be in form of a powder, which in particular may be obtained by submitting the microcapsule slurry to a drying, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, gum Arabic, vegetable gums, pectins, xanthans, alginates, carrageenans or cellulose derivatives to provide microcapsules in a powder form.

However, one may cite also other drying method such as the extrusion, plating, spray granulation, the fluidized bed, or even a drying at room temperature using materials (carrier, desiccant) that meet specific criteria as disclosed in WO 2017/134179.

In another aspect, the present invention relates to a method to confer, enhance, improve or modify the odor properties of a perfuming composition, the air surrounding the perfuming composition, a surface or a perfumed article, comprising adding to the composition, the air, or article, or contacting or treating the surface with an effective amount of at least one compound of formula (I) as defined above. The term “surface”, as used herein may refer to a user’s skin, hair, a textile, or hard surface, on to which, a perfume composition comprising or containing the at least one compound of formula (I) is applied.

In another aspect, the present invention relates to a method for intensifying or prolonging the diffusion effect of the characteristic fragrance of at least one carbonyl compound of formula (II), of at least one formate ester of formula (III) and/or of at least one alcohol of formula (IV) as defined above, on a surface or the air surrounding the perfuming composition, wherein the surface, or the air is treated with at least one compound (I) as defined above, or with a composition or article containing at least one compound (I), under conditions susceptible of allowing the release of at least one carbonyl compound formula (II), of at least one formate ester of formula (III) and/or of at least one alcohol of formula (IV) over time.

Moreover, the present invention relates to a perfuming composition comprising i) at least one compound of formula (I), as defined above;

ii) at least one ingredient selected from the group consisting of a perfumery carrier and a perfumery base; and iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylene diisocyanate or a Biuret of hexamethylene diisocyanate or a trimer of xylene diisocyanate with trimethylolpropane (known with the tradename of Takenate®, origin: Mitsui Chemicals), among which a trimer of xylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

The term "perfumery base" is understood as a composition comprising at least one perfuming co-ingredient.

The perfuming co-ingredient is not a compound according to the invention. Moreover, the term "perfuming co-ingredient" is understood as a compound, which is used in a perfuming preparation or composition to impart a hedonic effect. In other words, such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpene hydrocarbons, nitrogenous or *sulphurous* heterocyclic compounds and essential oils, and the perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal, nonanal and/or nonenal;

Aromatic-herbal ingredients: *eucalyptus* oil, camphor, eucalyptol, 5-methyltricyclo[6.2.1.0~2,7-]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;

Ba alsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino) benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclohexyl)ethoxycarbonyl]methyl propanoate;

Woody ingredients: 1-[1(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds also known as properfume or profragrance. Non-limiting examples of suitable properfumes or profragrances may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, 3-(dodecylthio)-1-(2,6,6-trimethyl-3-cyclohexen-1-yl)-1-butanone, 2-(dodecylthio)octan-4-one, 2-phenylethyl oxo(phenyl)acetate, 3,7-dimethylocta-2,6-dien-1-yl oxo(phenyl)acetate, (Z)-hex-3-en-1-yl oxo(phenyl)acetate, 3,7-dimethyl-2,6-octadien-1-yl hexadecanoate, bis(3,7-dimethylocta-2,6-dien-1-yl) succinate, (2-((2-methylundec-1-en-1-yl)oxy)ethyl)benzene, 1-methoxy-4-

(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl)naphthalene, (2-phenethoxyvinyl)benzene, 2-(1-((3,7-dimethyloct-6-en-1-yl)oxy)prop-1-en-2-yl)naphthalene, (2-((2-pentylcyclopentylidene)methoxy)ethyl)benzene or a mixture thereof.

The term "perfumery adjuvant" is understood as an ingredient capable of imparting additional added benefit such as a color, a particular light resistance, chemical stability and etc. A detailed description of the nature and type of adjuvant commonly used in perfuming bases cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants, heat/light and or buffers or chelating agents, such as BHT), coloring agents (e.g. dyes and/or pigments), preservatives (e.g. antibacterial or antimicrobial or antifungal or anti-irritant agents), abrasives, skin cooling agents, fixatives, insect repellants, ointments, vitamins and mixture thereof.

It is understood that a person skilled in the art is perfectly able to design optimal formulations for the desired effect by admixing the above-mentioned components of a perfuming composition, simply by applying the standard knowledge of the art as well as by trial and error methodologies.

An invention's composition consisting of at least one of the invention's compounds of formula (I) and at least one perfumery carrier represents a particular embodiment of the invention as well as a perfuming composition comprising at least one of the invention's compounds of formula (I), at least one perfumery carrier, at least one perfumery base, and optionally at least one perfumery adjuvant.

It is useful to mention here that the possibility to have, in the compositions mentioned above, more than one of the invention's compounds of formula (I) or other precursors of similar type is important as it enables the perfumer to prepare accords, perfumes, possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as the mixture does not provide the inventive compound in a suitable form for perfumery. Thus, unpurified reaction mixtures are generally excluded from the present invention unless otherwise specified.

Furthermore, the invention's compounds of formula (I) can also be advantageously used in all the fields of modern perfumery, i.e. fine or functional perfumery, to positively impart or modify the odor of a consumer product into which the compound (I) is added. Therefore, the present invention also relates to a perfumed consumer product comprising at least one compound of formula (I), as defined above or a perfuming composition as defined above.

For the sake of clarity, it has to be mentioned that, the term "perfumed consumer product" is understood as a consumer product which is expected to deliver at least a pleasant perfuming effect to the surface to which it is applied (e.g. skin, hair, textile, or hard surface). In other words, a perfumed consumer product according to the invention is a perfumed consumer product which comprises the functional formulation, as well as optionally additional benefit agents, corresponding to the desired consumer product, e.g. a conditioner, a detergent or an air freshener, and an olfactively effective amount of at least one invention's compound. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

In one embodiment, the perfumed consumer product is a perfume, a fabric care product, a body-care product, a cosmetic preparation, a skin-care product, an air care product or a home care product.

Non-limiting examples of suitable perfumed consumer products include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup; or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furniture care product, a wipe, a dish detergent or a hard-surface (e.g. a floor, bath, sanitary or a window-cleaning) detergent; a leather care product; a car care product, such as a polish, a wax or a plastic cleaner.

Typical examples of fabric detergents or softener compositions into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullmann's Encyclopedia of Industrial Chemistry, Vol. 20, Wiley-VCH, Weinheim, p. 355-540 (2012); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10% by weight, or even more, of the compounds of the invention based on the weight of the composition into which they are incorporated. In the case of perfumed consumer product, typical concentrations are in the order of 0.0001% to 5% by weight, or even more, of the compounds of the invention based on the weight of the consumer product into which they are incorporated.

Moreover, the present invention relates to a compound of formula (I). So another object of the invention is a compound of formula (I)

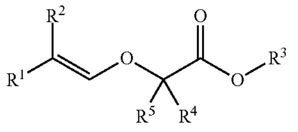

in the form of any one of its stereoisomers or a mixture thereof and wherein $R^1$ is a $C_{2-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a hydroxy, $C_{1-15}$ alkyl, $C_{2-15}$ alkenyl, $C_{1-15}$ alkoxy, $C_{2-15}$ alkenyloxy, $C_{3-15}$ cycloalkyl, $C_{5-15}$ cycloalkenyl, $C_{3-15}$ heterocycloalkyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^2$ represents a hydrogen atom, a $C_{1-3}$ alkyl or a phenyl group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

$R^3$ represents a hydrogen atom, a $C_{1-10}$ alkyl group, a $C_{3-10}$ alkenyl group, a benzyl group, a 2-phenylethyl group or a $C_{5-8}$ cycloalkyl group optionally substituted by one, two or three $C_{1-4}$ alkyl groups;

$R^4$ represents a hydrogen atom or a methyl, phenyl or $CH_2C(O)OR^3$ group; wherein $R^3$ has the same meaning as defined above;

$R^5$ represents a hydrogen atom or a methyl group; and provided that when $R^2$, $R^4$ and $R^5$ are a hydrogen atom, $R^1$ is not an unsubstituted phenyl group; and provided that methyl 2-((2,2-diphenylvinyl)oxy)acetate and ethyl 2-((3-phenylprop-1-en-1-yl)oxy)acetate are excluded.

In a further aspect, the present invention also relates to the use of precursor compounds for releasing compounds selected from the group consisting of a) a carbonyl compound of formula (II)

wherein $R^1$ is a $C_{1-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a hydroxy, $C_{1-15}$ alkyl, $C_{2-15}$ alkenyl, $C_{1-15}$ alkoxy, $C_{2-15}$ alkenyloxy, $C_{3-15}$ cycloalkyl, $C_{5-15}$ cycloalkenyl, $C_{3-15}$ heterocycloalkyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^2$ represents a hydrogen atom, a $C_{1-6}$ alkyl or phenyl group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

b) a formate ester of formula (III)

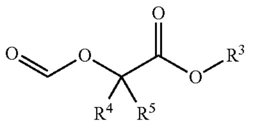

$R^3$ represents a hydrogen atom, a $C_{1-10}$ alkyl group, a $C_{3-10}$ alkenyl group, a benzyl group, a 2-phenylethyl group or a $C_{5-8}$ cycloalkyl group optionally substituted by one, two or three $C_{1-4}$ alkyl groups;

$R^4$ represents a hydrogen atom, a $C_{1-6}$ alkyl, a phenyl or a $CH_2C(O)OR^3$ group; wherein $R^3$ has the same meaning as defined above;

$R^5$ represents a hydrogen atom or a methyl group;

c) an alcohol of formula (IV)

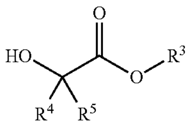

wherein $R^3$, $R^4$ and $R^5$ have the same meaning as defined above;

wherein at least one of the compounds of formula (II), (III) or (IV) is an active compound;

wherein the precursor compound comprises a compound of formula (I)

(I)

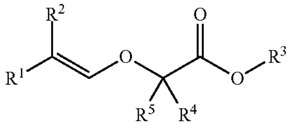

in the form of any one of its stereoisomers or a mixture thereof, and wherein $R^1$, $R^2$ and $R^3$, $R^4$ and $R^5$ have the same meaning as defined above;

by exposing the precursor compound of formula (I) to an environment wherein the compound is oxidized; i.e. ambient conditions.

In a further aspect, the present invention relates to the use of at least one compound of formula (I) as defined above to confer, enhance, improve or modify the odor properties of a perfuming composition, the air surrounding the perfuming composition, a surface, or of a perfumed article, comprising adding to the composition or article or contacting or treating the surface with an effective amount of at least one compound of formula (I) as defined above. The term "surface", as used herein may refer to a user's skin, hair, a textile, or hard surface, on to which, a perfume composition comprising or containing the at least one compound of formula (I) is applied.

In a further aspect, the present invention relates to the use of at least one compound of formula (I) as defined above for intensifying or prolonging the diffusion effect, and/or perception of the characteristic fragrance of at least one carbonyl compound formula (II), of at least one formate ester of formula (III) and/or of at least one alcohol of formula (IV) as defined above, on a surface, wherein the surface is treated with at least one compound of formula (I) as defined above, or with a composition or article containing the at least one compound of formula (I), under conditions susceptible of allowing the release of the at least one carbonyl compound formula (II), of at least one formate ester of formula (III) and/or of at least one active alcohol of formula (IV) over time.

The compounds of formula (I) can be prepared according to standard methods known in the art as described herein-below.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in 8 ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift δ ppm and hybridization from DEPT 90 and DEPT 135 experiments, C, quaternary; CH, methine; $CH_2$, methylene; $CH_3$, methyl.

Example 1

Preparation of Compounds According to Formula (I) Releasing a Carbonyl Compound of Formula (I)

Compound 1. methyl 2-((2-methylundec-1-en-1-yl)oxy)acetate

The dimethyl acetal of 2-methylundecanal (10.0 g. 43.4 mmol), methyl glycolate (7.82 g, 87 mmol), and $KHSO_4$ (0.06 g, 0.43 mmol) were added to a 25 ml, round-bottomed flask equipped with a distillation head and nitrogen bubbler. The mixture was heated at 150° C. (oil bath) for 40 min while allowing liberated methanol to distill from the reaction vessel. Additional methyl glycolate (3.87 g, 43 mmol) was added and the mixture was heated at 190° C. (oil bath) for 1 h. The mixture was placed under vacuum (5 Torr) and heating was continued at 190° C. (oil bath) for 2.5 h while allowing excess methyl glycolate to distill from the reaction flask. The title compound (5.4 g, 48% yield) was isolated by short-path, vacuum distillation from the reaction flask (bp 110° C., 4 Pa) as a colorless oil (E/Z=58:42).

$^1$H NMR ($CDCl_3$, 600 MHz): δ 0.88 (t, J=7.0 Hz, 3H), 1.20-1.41 (m, 14H), $1.53_Z$ and $1.64_E$ (both d, J=1.1 Hz, 3H), $1.86_E$ and $2.11_Z$ (both t, J=7.5 Hz, 2H), $3.76_Z$ and $3.77_E$ (both s, 3H), $4.24_Z$ and $4.26_E$ (both s, 3H), $5.77_Z$ and $5.79_E$ (both s, 1H).

$^{13}$C NMR ($CDCl_3$, 150 MHz): δ 12.94 ($CH_3$), 14.13 ($CH_3$), 17.15 ($CH_3$), 22.70 ($CH_2$), 27.32 ($CH_2$), 27.85 ($CH_2$), 28.90 ($CH_2$), 29.19 ($CH_2$), 29.36 ($CH_2$), 29.39 ($CH_2$), 29.52 ($CH_2$), 29.53 ($CH_2$), 29.61 ($CH_2$), 29.62 ($CH_2$), 29.65 ($CH_2$), 31.93 ($CH_2$), 31.94 ($CH_2$), 33.78 ($CH_2$), 51.92 ($CH_3$), 51.96 ($CH_3$), 68.39 ($CH_2$), 117.16 (C), 117.34 (C), 139.50 (CH), 139.62 (CH), 170.28 (C), 170.33 (C).

Compound 2. methyl (S)-2-((2-methylundec-1-en-1-yl)oxy)propanoate

The dimethyl acetal of 2-methylundecanal (8 g. 34.7 mmol), methyl (S)-lactate (7.29 g, 70 mmol), and $KHSO_4$ (0.048 g, 0.35 mmol) were added to a 25 ml, round-bottomed flask equipped with a Vigreux column (10 cm), distillation head and nitrogen bubbler. The mixture was heated for 1 h at 150° C. (oil bath) while allowing liberated methanol to distill from the reaction vessel. After removing the Vigreux column, the mixture was heated at 190° C. for 2 h while allowing the excess methyl lactate to distill from the reaction flask. The title compound (6.4 g, 68% yield) was isolated by short-path, vacuum distillation from the reaction flask (bp 105° C., 3 Pa) as a colorless oil (E/Z=57:43).

$^1$H NMR ($CDCl_3$, 500 MHz): δ 0.88 (t, J=6.9 Hz, 3H), 1.18-1.41 (m, 14H), $1.44_Z$ and $1.46_E$ (both d, J=7.0 Hz, 3H), $1.51_Z$ and $1.63_E$ (both d, J=1.3 Hz, 3H), $1.85_E$ (t, J=7.4 Hz, 1.2H), $2.02\text{-}2.10_Z$ (m, 0.4H), $2.12\text{-}2.19_Z$ (m, 0.4H), $3.74_Z$ and $3.75_E$ (both s, 3H), $4.16_Z$ and $4.19_E$ (both q, J=6.9 Hz, 1H), $5.78_Z$ and $5.80_E$ (both s, 1H).

$^{13}$C NMR ($CDCl_3$, 125.8 MHz): δ 13.03 ($CH_3$), 14.13 ($CH_3$), 17.20 ($CH_3$), 18.18 ($CH_3$), 18.20 ($CH_3$), 22.71 ($CH_2$), 22.72 ($CH_2$), 27.30 ($CH_2$), 27.89 ($CH_2$), 28.88 ($CH_2$), 29.18 ($CH_2$), 29.38 ($CH_2$), 29.42 ($CH_2$), 29.48 ($CH_2$), 29.55 ($CH_2$), 29.61 ($CH_2$), 29.65 ($CH_2$), 29.67 ($CH_2$), 31.94 ($CH_2$), 31.97 ($CH_2$), 33.86 ($CH_2$), 51.99 ($CH_3$), 52.03 ($CH_3$), 75.44 (CH), 75.47 (CH), 117.47 (C), 117.54 (C), 138.33 (CH), 138.43 (CH), 172.87 (C).

Compound 3. methyl 2-methyl-2-((2-methylundec-1-en-1-yl)oxy)propanoate

The dimethyl acetal of 2-methylundecanal (9.2 g. 39.9 mmol), methyl 2-hydroxy-isobutyrate (19.5 g, 165 mmol), and $KHSO_4$ (0.058 g, 0.42 mmol) were added to a 25 ml, round-bottomed flask equipped with a distillation head and nitrogen bubbler. The mixture was heated at 190° C. (oil bath) for 2 h while allowing methanol and excess methyl 2-hydroxyisobutyrate to distill from the reaction flask. After adding $Na_2CO_3$ (0.5 g), the title compound (6.4 g, 56% yield) was isolated by short-path, vacuum distillation from the reaction flask (bp 113° C., 3.3 Pa) as a colorless oil (E/Z=67:33).

$^1H$ NMR ($CDCl_3$, 600 MHz): (δ 0.88 (t, J=7.0 Hz, 3H), 1.19-1.40 (m, 14H), $1.45_Z$ and $1.47_E$ (both s, 6H), $1.52_Z$ and $1.60_E$ (both d, J=1.2 Hz, 3H), $1.86_E$ and $2.08_Z$ (both t, J=7.5 Hz, 2H), $3.74_Z$ and $3.75_E$ (both s, 3H), $5.80_Z$ and $5.83_E$ (both s, 1H).

$^{13}C$ NMR ($CDCl_3$, 150.9 MHz): (δ 12.95 ($CH_3$), 14.13 ($CH_3$), 17.40 ($CH_3$), 18.18 ($CH_3$), 18.20 ($CH_3$), 22.71 ($CH_2$), 22.72 ($CH_2$), 24.98 ($CH_3$), 25.03 ($CH_3$), 27.24 ($CH_2$), 27.89 ($CH_2$), 28.74 ($CH_2$), 29.15 ($CH_2$), 29.37 ($CH_2$), 29.41 ($CH_2$), 29.46 ($CH_2$), 29.54 ($CH_2$), 29.58 ($CH_2$), 29.65 ($CH_2$), 31.93 ($CH_2$), 31.96 ($CH_2$), 34.03 ($CH_2$), 52.21 ($CH_3$), 52.23 ($CH_3$), 78.35 (C), 78.49 (C), 118.44 (C), 118.75 (C), 134.51 (CH), 134.69 (CH), 174.56 (C), 174.59 (C).

Compound 4. methyl (S)-2-((2-methyl-4 phenylbut-1-en-1-yl)oxy)propanoate

The dimethyl acetal of 2-methyl-4-phenylbutanal (10.4 g. 49.9 mmol), methyl (S)-lactate (10.4 g, 99.9 mmol), and $KHSO_4$ (0.068 g, 0.5 mmol) were added to a 25 ml, round-bottomed flask equipped with a Vigreux column (10 cm), distillation head and nitrogen bubbler. The mixture was heated for 2 h at 150° C. (oil bath) while allowing liberated methanol to distill from the reaction vessel. After removing the Vigreux column, the mixture was heated at 190° C. for 1 h while allowing the excess methyl lactate to distill from the reaction flask. The title compound (8.5 g, 68% yield) was isolated by short-path, vacuum distillation from the reaction flask (bp 120° C., 4 Pa) as a colorless oil (E/Z=60:40).

$^1H$ NMR ($CDCl_3$, 600 MHz): δ $1.40_Z$ and $1.43_E$ (both d, J=6.9 Hz, 3H), $1.55_Z$ and $1.71_E$ (both s, 3H), $2.17_E$ (t, J=7.9 Hz, 1.2H), $2.38_Z$ (ddd, J=15.6, 13.4, 9.6 Hz, 0.4H), $2.48_Z$ (ddd, J=16.7, 13.3, 9.6 Hz, 0.4H), 2.63-2.77 (m, 2H), $3.73_E$ and $3.74_Z$ (both s, 3H), $4.08_Z$ and $4.15_E$ (both q, J=6.9 Hz, 1H), $5.77_E$ and $5.80_Z$ (both s, 1H), 7.12-7.19 (m, 2H), 7.20-7.28 (m, 3H).

$^{13}C$ NMR ($CDCl_3$, 150.9 MHz): δ 13.20 ($CH_3$), 17.34 ($CH_3$), 18.16 ($CH_3$), 30.92 ($CH_2$), 33.68 ($CH_2$), 34.69 ($CH_2$), 36.01 ($CH_2$), 52.03 ($CH_3$), 52.07 ($CH_3$), 75.37 (CH), 75.41 (CH), 116.36 (C), 116.39 (C), 125.61 (CH), 125.71 (CH), 128.13 (CH), 128.23 (CH), 128.40 (CH), 128.45 (CH), 138.84 (CH), 139.12 (CH), 142.13 (C), 142.53 (C), 172.74 (C), 172.81 (C).

Compound 5. octyl (S)-2-((2-methylundec-1-en-1-yl)oxy)propanoate

Methyl (S)-2-((2-methylundec-1-en-1-yl)oxy)propanoate (Compound 2, 8.2 g, 30.2 mmol), octanol (15.7 g, 121 mmol), DMAP (3.69 g, 30.2 mmol) and cyclohexane (100 mL) were added to a round-bottomed flask (250 mL) equipped with a Dean-Stark trap. The mixture was heated at reflux for 1 day. The mixture was concentrated in vacuo and the remaining residue subjected to silica gel flash chromatography (hexane/EtOAc 100:0→90:10) to afford 9.36 g (25.4 mmol, 84% yield) of the title compound as a colorless oil (E/Z=61:39).

$^1H$ NMR ($CDCl_3$, 600 MHz): δ 0.880 (t, J=7.0 Hz, 3H), 0.882 (t, J=7.0 Hz, 3H), 1.18-1.41 (m, 24H), $1.44_Z$ and $1.46_E$ (both d, J=6.9 Hz, 3H), $1.51_Z$ and $1.63_E$ (both d, J=1.2 Hz, 3H), 1.61-1.67 (m, 2H), $1.85_E$ (t, J=7.5 Hz, 1.2H), 2.02-$2.07_Z$ (m, 0.4H), 2.13-$2.19_Z$ (m, 0.4H), 4.09-4.20 (m, 3H), $5.79_Z$ and $5.81_E$ (both s, 1H).

$^{13}C$ NMR ($CDCl_3$, 125.8 MHz): δ 13.06 ($CH_3$), 14.08 ($CH_3$), 14.12 ($CH_3$), 17.21 ($CH_3$), 18.20 ($CH_3$), 18.23 ($CH_3$), 22.65 ($CH_2$), 22.70 ($CH_2$), 22.71 ($CH_2$), 25.85 ($CH_2$), 27.32 ($CH_2$), 27.93 ($CH_2$), 28.60 ($CH_2$), 28.92 ($CH_2$), 29.20 ($CH_2$), 29.21 ($CH_2$), 29.38 ($CH_2$), 29.41 ($CH_2$), 29.51 ($CH_2$), 29.56 ($CH_2$), 29.61 ($CH_2$), 29.64 ($CH_2$), 29.66 ($CH_2$), 31.80 ($CH_2$), 31.93 ($CH_2$), 31.96 ($CH_2$), 33.88 ($CH_2$), 65.09 ($CH_2$), 65.12 ($CH_2$), 75.55 (CH), 117.16 (C), 117.24 (C), 138.38 (CH), 138.51 (CH), 172.54 (C), 172.55 (C).

Compound 6. (Z)-hex-3-en-1-yl (S)-2-((2-methylundec-1-en-1-yl)oxy)propanoate

A mixture of methyl (S)-2-((2-methylundec-1-en-1-yl) oxy)propanoate (Compound 2, 5.26 g, 19.4 mmol), (Z)-hex-3-en-1-ol (33 g, 329 mmol), DBU (2.1 g, 13.8 mmol) was heated for 9 h at 120° C. (oil bath). The mixture was diluted with ethyl ether and water washed. The organic phase was dried over $Na_2SO_4$, filtered and concentrated under vacuum. Excess (Z)-hex-3-en-1-ol was removed by short-path, vacuum distillation and the remaining residue subjected to silica gel flash chromatography (hexane/EtOAc 100:0→90:10) to afford 3.2 g (9.4 mmol, 48% yield) of the title compound as a pale-yellow oil (E/Z=58:42).

$^1H$ NMR ($CDCl_3$, 600 MHz): δ 0.88 (t, J=7.0 Hz, 3H), 0.97 (t, J=7.5 Hz, 3H), 1.18-1.41 (m, 14H), $1.43_Z$ and $1.45_E$ (both d, J=6.9 Hz, 3H), $1.51_Z$ and $1.63_E$ (both d, J=1.2 Hz, 3H), $1.85_E$ (t, J=7.5 Hz, 1.2H), 2.01-$2.08_Z$ and 2.13-$2.19_Z$ (both m, 0.8H), 2.06 (pentet, J=7.6 Hz, 2H), 2.40 (q, J=7.1 Hz, 2H), 4.10-4.19 (m, 3H), 5.30 (dt, J=10.8, 7.3 Hz, 1H), 5.50 (dt, J=10.8, 7.3 Hz, 1H), $5.79_Z$ and $5.80_E$ (both s, 1H).

$^{13}C$ NMR ($CDCl_3$, 150.9 MHz): δ 13.06 ($CH_3$), 14.13 ($CH_3$), 14.22 ($CH_3$), 17.20 ($CH_3$), 18.20 ($CH_3$), 18.22 ($CH_3$), 20.63 ($CH_2$), 22.70 ($CH_2$), 22.71 ($CH_2$), 26.72 ($CH_2$), 27.31 ($CH_2$), 27.91 ($CH_2$), 28.91 ($CH_2$), 29.21 ($CH_2$), 29.37 ($CH_2$), 29.41 ($CH_2$), 29.50 ($CH_2$), 29.55 ($CH_2$), 29.61 ($CH_2$), 29.63 ($CH_2$), 29.67 ($CH_2$), 31.93 ($CH_2$), 31.96 ($CH_2$), 33.87 ($CH_2$), 64.41 ($CH_2$), 64.44 ($CH_2$), 75.47 (CH), 117.28 (C), 117.35 (C), 123.45 (CH), 123.48 (CH), 134.68 (CH), 134.70 (CH), 138.35 (CH), 138.47 (CH), 172.44 (C), 172.46 (C).

Compound 7. methyl (S)-2-(dodec-1-en-1-yloxy)propanoate

The dimethyl acetal of 2-dodecanal (11.5 g, 49.9 mmol), methyl (S)-lactate (13.3 g, 128 mmol), and $KHSO_4$ (0.031 g, 0.46 mmol) were added to a 35 ml, round-bottomed flask equipped with a Vigreux column (10 cm), distillation head and nitrogen bubbler. The mixture was heated for 1.5 h at 150° C. (oil bath) while allowing liberated methanol to distill from the reaction vessel. The reaction mixture was subjected to short-path, vacuum distillation affording a fraction (128-138° C., 3.3 Pa) containing the enol ether. The fraction was subjected to silica gel flash chromatography (hexane/EtOAc 100:0→90:10) followed by Kugelrohr distillation to afford 2.0 g (7.4 mmol, 15% yield) of the title compound as a pale-yellow oil (E/Z=37:63).

$^1H$ NMR ($CDCl_3$, 500 MHz): δ 0.88 (t, J=6.9 Hz, 3H), 1.21-1.40 (m, 16H), $1.46_E$ and $1.47_Z$ (both d, J=6.9 Hz, 3H), $1.89_E$ and $2.12_Z$ (both q, J=7.2 Hz, 2H), $3.75_Z$ and $3.76_E$ (both s, 3H), $4.24_Z$ and $4.31_E$ (both q, J=6.9 Hz, 1H), $4.46_Z$ (td, J=7.3, 6.2 Hz, 0.6H), $4.86_E$ (dt, J=12.6, 7.4 Hz, 0.4H), $5.90_Z$ (dt, J=6.2, 1.5 Hz, 0.6H), $6.14_E$ (dt, J=12.6, 1.2 Hz, 0.4H).

$^{13}C$ NMR ($CDCl_3$, 125.8 MHz): δ 14.13 ($CH_3$), 18.14 ($CH_3$), 18.17 ($CH_3$), 22.72 ($CH_2$), 23.96 ($CH_2$), 27.57 ($CH_2$), 29.00 ($CH_2$), 29.30 ($CH_2$), 29.38 ($CH_2$), 29.40 ($CH_2$), 29.50 ($CH_2$), 29.55 ($CH_2$), 29.66 ($CH_2$), 29.69

($CH_2$), 29.70 ($CH_2$), 30.40 ($CH_2$), 31.95 ($CH_2$), 31.96 ($CH_2$), 52.07 ($CH_3$), 52.12 ($CH_3$), 73.69 (CH), 75.63 (CH), 107.19 (CH), 109.63 (CH), 142.86 (CH), 144.19 (CH), 172.58 (C), 172.72 (C).

Compound 8. (±)-methyl 2-((3-methyl-5 phenyl-pent-1-en-1-yl)oxy)propanoate

The dimethyl acetal of 5-phenyl-3-methylpentanal (9 g, 40.8 mmol), (±)-methyl lactate (16.9 g, 162 mmol), and $KHSO_4$ (0.17 g, 1.24 mmol) were added to a 35 ml, round-bottomed flask equipped with a distillation head and nitrogen bubbler. The mixture was heated at 140° C. (oil bath) while allowing liberated methanol to distill from the reaction vessel. After 1 h, the reaction vessel was placed under vacuum (60 kPa) and the pressure reduced to 40 kPa while allowing methyl lactate to distill from the flask. After 1 h, the pressure was progressively reduced to 40 Pa, over a 1.5-h period. Following this 0.5 g of $Na_2CO_3$ was added to the flask and the title compound (4.73 g, 45% yield) was isolated by short-path, vacuum distillation from the reaction flask (bp 115-117° C., 1 Pa) as a colorless oil (mixture of diastereomers, E/Z=50:50).

$^1$H NMR ($CDCl_3$, 600 MHz): δ 0.993, 0.999, 1.005, 1.015 (all d, J=6.7 Hz, 3H), 1.472, 1.475, 1.480, 1.483 (all d, J=6.9 Hz, 3H), 1.50-1.58 (m, 1H), 1.58-1.67 (m, 1H), 2.00-2.09 (m, 0.5 H), 2.47-2.68 (m, 2H), 2.71-2.82 (m, 0.5H), 3.73, 3.74, 3.76, (all s, 3H), 4.24-4.25 (overlapping q, J=6.9 Hz, 0.5H), 4.29-4.37 (m, 1H), 4.73, 4.78 (both dd, J=12.6, 8.9 Hz, 0.5 H), 5.926, 5.932 (d, J=6.2 Hz, 0.5 H), 6.131, 6.155 (both d, J=12.6 Hz, 0.5H), 7.130-7.290 (m, 5H).

$^{13}$C NMR ($CDCl_3$, 150.9 MHz): (δ 18.13 ($CH_3$), 18.17 ($CH_3$), 21.32 ($CH_3$), 21.87 ($CH_3$), 21.97 ($CH_3$), 28.88 (CH), 28.90 (CH), 32.36 (CH), 32.44 (CH), 33.62 ($CH_2$), 33.84 ($CH_2$), 33.92 ($CH_2$), 39.83 ($CH_2$), 39.45 ($CH_2$), 39.52 ($CH_2$), 39.58 ($CH_2$), 52.05 ($CH_3$), 52.06 ($CH_3$), 52.13 ($CH_3$), 52.15 ($CH_3$), 73.53 (CH), 73.85 (CH), 75.69 (CH), 75.76 (CH), 112.55 (CH), (CH), 114.95 (CH), 115.20 (CH), 125.41 (CH), 125.47 (CH), 125.59 (CH), 128.15 (CH), 128.17 (CH), 128.26 (CH), 128.27 (CH), 128.38 (CH), 128.39 (CH), 128.43 (CH), 128.48 (CH), 142.49 (CH), 142.53 (CH), 142.65 (C), 142.67 (C), 143.12 (C), 143.28 (C), (CH), 143.75 (CH), 172.49 (C), 172.55 (C), 172.65 (C), 172.67 (C).

Compound 9. methyl (S)-2-(styryloxy)propanoate

The dimethyl acetal of phenylacetaldehyde (18.3 g, 110 mmol), methyl (S)-lactate (28.6 g, 275 mmol), and $KHSO_4$ (0.075 g, 0.50 mmol) were added to a 50 ml, round-bottomed flask equipped with a Vigreux column (10 cm), distillation head and nitrogen bubbler. The mixture was heated for 1 h at 150° C. (oil bath) while allowing liberated methanol to distill from the reaction vessel. After removal of the Vigreux column, the mixture was heated at 190° C. for 1 h while allowing the excess methyl lactate to distill from the reaction flask. The title compound (10.7 g, 47% yield) was isolated by short-path, vacuum distillation from the remaining reaction mixture (bp 114° C., 15 Pa) as a colorless oil (E/Z=50:50).

$^1$H NMR ($CDCl_3$, 600 MHz): δ 1.53 and 1.57 (both d, J=6.9 Hz, 3H), 3.75 and 3.76 (both s, 3H), 4.40 and 4.48 (both q, J=6.9 Hz, 1H), $5.29_Z$ (d, J=7.0 Hz, 0.5H), $5.94_E$ (d, J=12.9 Hz, 0.5H), $6.15_Z$ (d, J=7.0 Hz, 0.5H), $6.87_E$ (d, J=12.9 Hz 0.5H), 7.10-7.20 (m, 1H), 7.18-7.31 (m, 3H), 7.62 (d, J=8.1 Hz, 1H). $^{13}$C NMR ($CDCl_3$, 125.8 MHz): δ 18.17 ($CH_3$), 18.23 ($CH_3$), 52.27 ($CH_3$), 52.32 ($CH_3$), 74.59 (CH), 76.88 (CH), 107.24 (CH), 108.53 (CH), 125.34 (CH), 126.02 (CH), 126.07 (CH), 128.16 (CH), 128.51 (CH), 128.57 (CH), 135.45 (C), 135.69 (C), 144.52 (CH), 146.06 (CH), 171.93 (C), 172.12 (C).

Compound 10. methyl 2-methyl-2-(styryloxy)propanoate

The dimethyl acetal of phenylacetaldehyde (9.9 g, 59.6 mmol), methyl 2-hydroxy-2-isobutyrate (14.3 g, 121 mmol), and $KHSO_4$ (0.087 g, 0.64 mmol) were added to a 25 ml, round-bottomed flask equipped with a Vigreux column (10 cm), distillation head and nitrogen bubbler. The mixture was heated for 1 h at 170° C. and 1 h at 190° C. (oil bath) while allowing liberated methanol to distill from the reaction vessel. The mixture then was heated at 150° C. under vacuum (0.7 kPa) for 1 h. After adding $Na_2CO_3$ (0.5 g), the title compound (3.7 g, 28% yield) was isolated by fractional distillation from the reaction flask (bp 92° C., 4 Pa) as a colorless oil (E/Z=41:59).

$^1$H NMR ($CDCl_3$, 500 MHz): δ $1.56_E$ and $1.57_Z$ (both s, 6H), $3.76_Z$ and $3.77_E$ (both s, 3H), $5.32_Z$ (d, J=7.0 Hz, 0.6H), $6.10_E$ (d, J=12.4 Hz, 0.4H), $6.26_Z$ (d, J=7.0 Hz, 0.6H), $6.85_E$ (d, J=12.4 Hz, 0.4H), 7.11-7.16 (m, 1H), 7.19-7.30 (m, 2.8H), 7.61 (d, J=7.8 Hz, 1.2H).

$^{13}$C NMR ($CDCl_3$, 125.8 MHz): δ 25.08 ($CH_3$), 25.15 ($CH_3$), 52.48 ($CH_3$), 52.53 ($CH_3$), 79.53 (C), 79.89 (C), 107.24 (CH), 107.51 (CH), 111.14 (CH), 125.37 (CH), 125.86 (CH), (CH), 128.12 (CH), 128.46 (CH), 128.52 (CH), 135.70 (C), 135.97 (C), 141.07 (CH), 142.54 (CH), 173.76 (C), 173.86 (C).

Compound 11. methyl (S)-2-((2-phenylprop-1-en-1-yl)oxy)propanoate

The dimethyl acetal of 2-phenylpropanal (7.23 g, 40.1 mmol), methyl (S)-lactate (8.46 g, 81.2 mmol), and $KHSO_4$ (0.052 g, 0.38 mmol) were added to a 25 ml, round-bottomed flask equipped with a distillation head and nitrogen bubbler. The mixture was heated for 1 h at 120° C. (oil bath) while allowing liberated methanol to distill from the reaction vessel. The mixture was heated at 190° C. for 1 h while allowing the excess methyl lactate to distill from the reaction flask. The title compound (6.4 g, 72% yield) was isolated by short-path, vacuum distillation from the reaction flask (bp 112° C., 3 Pa) as a colorless oil (E/Z=83:17).

$^1$H NMR ($CDCl_3$, 500 MHz): δ $1.50_Z$ and $1.53_E$ (both d, J=6.9 Hz, 3H), $1.91_Z$ and $2.05_E$ (both d, J=1.4 Hz, 3H), 3.75 (s, 3H), $4.32_Z$ and $4.37_E$ (both q, J=6.9 Hz, 1H), $6.13_Z$ and $6.42_E$ (both q, J=1.4 Hz, 1H), 7.15-7.19 (m, 1H), 7.24-7.33 (m, 3.7H), 7.65-7.69 (m, 0.3H).

$^{13}$C NMR ($CDCl_3$, 125.8 MHz): δ 12.88 ($CH_3$), 18.20 ($CH_3$), 18.26 ($CH_3$), 18.38 ($CH_3$), 52.17 ($CH_3$), 52.19 ($CH_3$), 76.03 (CH), 76.41 (CH), 112.63 (C), 116.91 (C), 125.25 (CH), 126.19 (CH), 127.70 (CH), 127.84 (CH), 128.31 (CH), 137.98 (C), 140.30 (C), 141.16 (CH), 141.93 (CH), 172.36 (C).

Compound 12. hexyl (S)-2-((2-phenylprop-1-en-1-yl)oxy)propanoate

Methyl (S)-2-((2-phenylprop-1-en-1-yl)oxy)propanoate (Compound 11, 5.0 g, 22.7 mmol), hexanol (9.3 g, 90.8 mmol), DMAP (0.84 g, 6.9 mmol) and cyclohexane (75 mL) were added to a round-bottomed flask (150 mL) equipped with a Dean-Stark trap. The mixture was heated at reflux for 1 day. The mixture was diluted with ethyl ether and washed with water. The organic phase was dried over $Na_2SO_4$, filtered and concentrated under vacuum. The crude product was subjected to silica gel flash chromatography (hexane/EtOAc 100:0→85:15) to afford 4.9 g (16.8 mmol, 74% yield) of the title compound as a colorless oil (E/Z=83:17).

$^1$H NMR ($CDCl_3$, 500 MHz): δ $0.87_Z$ and $0.88_E$ (both d, J=7.0 Hz, 3H), 1.24-1.31 (m, 4H), 1.31-1.38 (m, 2H), $1.52_Z$ and $1.54_E$ (both d, J=6.9 Hz, 3H), 1.60-1.68 (m, 2H), $1.92_Z$ and $2.05_E$ (both d, J=1.3 Hz, 3H), 4.10-4.22 (m, 2H), $4.33_Z$ and $4.37_E$ (both q, J=6.9 Hz, 1H), $6.15_Z$ and $6.43_E$ (both q, J=1.3 Hz, 1H), 7.15-7.21 (m, 1H), 7.24-7.34 (m, 3.7H), 7.67-7.70 (m, 0.3H).

$^{13}$C NMR ($CDCl_3$, 125.8 MHz): (δ 12.89 ($CH_3$), 13.97 ($CH_3$), 18.24 ($CH_3$), 18.27 ($CH_3$), 18.37 ($CH_3$), 22.50 ($CH_2$), 25.51 ($CH_2$), 28.52 ($CH_2$), 28.55 ($CH_2$), 31.38 ($CH_2$), 65.35 ($CH_2$), 76.17 (CH), 76.59 (CH), 112.43 (C), 116.75 (C), 125.24 (CH), 126.14 (CH), 126.16 (CH), 127.71 (CH), 127.82 (CH), 128.30 (CH), 138.01 (C), 140.37 (C), 141.24 (CH), 142.03 (CH), 172.07 (C).

Compound 13. (Z)-hex-3-en-1-yl (S)-2-((2-phenylprop-1-en-1-yl)oxy)propanoate Methyl (S)-2-((2-phenylprop-1-en-1-yl)oxy)propanoate (Compound 11, 5.0 g, 22.7 mmol), (Z)-hex-3-en-1-ol (9.1 g, 90.9 mmol), DMAP (0.84 g, 6.9 mmol) and cyclohexane (75 mL) were added to a round-bottomed flask (150 mL) equipped with a Dean-Stark trap. The mixture was heated at reflux for 28 h. The reaction mixture was concentrated under vacuum and filtered through a pad of silica gel. After removal of the solvent, the crude product was subjected to silica gel flash chromatography (hexane/EtOAc 100:0→80:20) to afford 2.7 g (9.3 mmol, 41% yield) of the title compound as a pale-yellow oil (E/Z=82:18).

$^1$H NMR ($CDCl_3$, 500 MHz): δ $0.956_E$ and $0.964_Z$ (both t, J=7.5 Hz, 3H), $1.51_Z$ and $1.54_E$ (both d, J=6.9 Hz, 3H), $1.92_Z$ and $2.05_E$ (both d, J=1.3 Hz, 3H), 2.00-2.09 (m, 2H), 2.41 (q, J=7.0 Hz, 2H), 4.11-4.22 (m, 2H), $4.32_Z$ and $4.36_E$ (both q, J=6.9 Hz, 1H), 5.26-5.34 (m, 1H), 5.45-5.55 (m, 1H), $6.15_Z$ and $6.42_E$ (both q, J=1.3 Hz, 1H), 7.16-7.21 (m, 1H), 7.24-7.35 (m, 3.7H), 7.66-7.70 (m, 0.3H).

$^{13}$C NMR ($CDCl_3$, 125.8 MHz): (δ 12.91 ($CH_3$), 14.19 ($CH_3$), 18.23 ($CH_3$), 18.28 ($CH_3$), 18.38 ($CH_3$), 20.62 ($CH_2$), 26.68 ($CH_2$), 64.67 ($CH_2$), 76.09 (CH), 76.49 (CH), 112.53 (C), 116.85 (C), 123.36 (CH), 123.40 (CH), 125.26 (CH), 126.16 (CH), 126.17 (CH), 127.72 (CH), 127.83 (CH), 128.30 (CH), 134.76 (CH), 134.80 (CH), 138.00 (C), 140.36 (C), 141.18 (CH), 141.97 (CH), 171.97 (C), 171.99 (C).

Compound 14. (±)-methyl 2-((2-methyldec-1-en-1-yl)oxy)propanoate

The dimethyl acetal of 2-methyldecanal (8.0 g. 37 mmol), (±)-methyl lactate (7.7 g, 74 mmol), and $KHSO_4$ (0.15 g, 1.10 mmol) were added to a 25 ml, round-bottomed flask equipped with a Vigreux column (10 cm), distillation head and nitrogen bubbler. The mixture was heated for 1 h at 150-160° C. (oil bath) while allowing liberated methanol to distill from the reaction vessel. After removing the Vigreux column, the mixture was heated at 180-190° C. for 1 h while allowing excess methyl lactate to distill from the reaction flask. The reaction mixture then was heated at 150° C. under vacuum (1.3 kPa) for an hour to remove any remaining methyl lactate. The title compound (8.57 g, 90% yield) was isolated by short-path, vacuum distillation from the reaction flask (bp 86-90° C., 1 Pa) as a colorless oil (E/Z=60:40).

$^1$H NMR ($CDCl_3$, 600 MHz): δ 0.88 (t, J=6.8 Hz, 3H), 1.18-1.41 (m, 10H), 1.32-1.41 (m, 2H), $1.45_Z$ and $1.46_E$ (both d, J=609 Hz, 3H), $1.52_Z$ and $1.63_E$ (both s, 3H), $1.85_E$ (t, J=7.4 Hz) and $2.03\text{-}2.09_Z$ (m) and $2.12\text{-}2.18_Z$ (m) (2H), $3.74_Z$ and $3.75_E$ (both s, 3H), $4.17_Z$ and $4.19_E$ (both q, J=6.9 Hz, 1H), $5.78_Z$ and $5.80_E$ (both s, 1H).

$^{13}$C NMR ($CDCl_3$, 150.9 MHz, E-isomer): δ 13.0 ($CH_3$), 14.1 ($CH_3$), 18.2 ($CH_3$), 22.7 ($CH_2$), 27.9 ($CH_2$), 29.2 ($CH_2$), 29.3 ($CH_2$), 29.5 ($CH_2$), 31.9 ($CH_2$), 33.8 ($CH_2$), 52.0 ($CH_3$), 75.4 (CH), 117.6 (C), 138.4 (CH), 172.9 (C).

Compound 15. (±)-methyl 2-((3-(4-methoxyphenyl)-2-methylprop-1-en-1-yl)oxy)propanoate Following the procedure described for compound 14 and starting from the dimethyl acetal of 3-(4-methoxyphenyl)-2-methylpropanal (8 g, 35.7 mmol), (±)-methyl lactate (7.4 g, 71.3 mmol), and $KHSO_4$ (0.15 g, 1.1 mmol), the title compound (7.59 g, 80% yield) was isolated by short-path, vacuum distillation (bp 117-120° C., 1 Pa) as a colorless oil (E/Z=57:43).

$^1$H NMR ($CDCl_3$, 600 MHz): δ $1.44_Z$ and $1.56_E$ (both s, 3H), $1.48_E$ and $1.50_Z$ (both d, J=6.9 Hz, 3H), $3.11_E$ (s, 1.2H), $3.37_Z$ and $3.41_Z$ (both d, J=14.2 Hz, 0.8H), $3.75_E$ and $3.76_Z$ (both s, 3H), 3.78 (s, 3H), $4.25_E$ and $4.26_Z$ (both q, J=6.9 Hz, 1H), $5.89_Z$ and $5.92_E$ (both s, 1H), 6.81 (d, J=8.4 Hz, 2H), $7.08_E$ and $7.14_Z$ (both d, J=8.4 Hz, 2H).

$^{13}$C NMR ($CDCl_3$, 150.9 MHz, E-isomer): δ 13.0 ($CH_3$), 18.2 ($CH_3$), 39.3 ($CH_2$), 52.1 ($CH_3$), 55.2 ($CH_3$), 75.5 (CH), 113.6 (CH), 116.8 (C), 129.6 (CH), 132.0 (C), 139.7 (CH), 158.0 (C), 172.7 (C).

Compound 16. (±)-methyl 2-((2-ethylhex-1-en-1-yl)oxy)propanoate

The title compound was prepared following the procedure described for compound 14 except that after heating the reaction mixture at 180° C. (oil bath) for 1 h, the reaction mixture then was heated at 140° C. under vacuum (12-1.3 kPa) for 1 h. Starting from the dimethyl acetal of 2-ethylhexanal (10 g, 57.4 mmol), (±)-methyl lactate (14.9 g, 143 mmol), and $KHSO_4$ (0.23 g, 1.72 mmol), the title compound (7.43 g, 60% yield) was isolated by short-path, vacuum distillation (bp 90-93° C., 53 Pa) as a colorless oil (isomer ratio=53:47).

$^1$H NMR ($CDCl_3$, 500 MHz): (δ 0.88 and 0.91 (both t, J=7.1 Hz, 3H), 0.96 and 0.97 (both t, J=7.3 Hz, 3H), 1.23-1.41 (m, 4H), 1.452 and 1.455 (both d, J=6.9 Hz, 3H), 1.85-1.94 (m, 2H), 2.05-2.20 (m, 2H), 3.75 (s, 3H), 4.182 and 4.177 (both q, J=6.9 Hz, 1H), 5.75 and 5.80 (both s, 1H).

$^{13}$C NMR ($CDCl_3$, 125.8 MHz): (δ 12.5 ($CH_3$), 13.1 ($CH_3$), 13.9 ($CH_3$), 14.0 ($CH_3$), 18.2 ($CH_3$), 20.1 ($CH_2$), 22.4 ($CH_2$), 22.6 ($CH_2$), 24.5 ($CH_2$), 26.5 ($CH_2$), 29.8 ($CH_2$), 30.3 ($CH_2$), 30.7 ($CH_2$), 51.99 ($CH_3$), 52.0 ($CH_3$), 75.5 (CH), 123.17 (C), 123.18 (C), 138.2 (CH), 172.9 (C).

Compound 17. (±)-methyl 2-((4-(4-methoxyphenyl)-2-methylbut-1-en-1-yl)oxy)propanoate General procedure: Methoxymethyltriphenylphosphonium chloride (15.1 g, 44.1 mmol) and the ketone (29.4 mmol) were added to 120 ml of toluene. Potassium t-butoxide (5.27 g, 47 mmol) was added to the stirring slurry in 4 portions every 15 min. The mixture was stirred for 4 h becoming a deep red color. It then was poured into 500 ml of water and extracted with EtOAc (3×250 mL). The organic phases were combined, dried over $Na_2SO_4$, filtered and concentrated to a grainy solid. The resulting methyl enol ether product was isolated by flash chromatography (silica gel, hexane) followed by bulb-to-bulb distillation. Alternatively, the solid was washed with hexane and filtered. Concentrating the filtrate afforded the crude methyl enol ether that was purified by fractional distillation. The methyl enol ether (30-40 mmol) then was combined with (±)-methyl lactate (2-2.5 equiv) and $KHSO_4$ (3 mol %) in a round-bottomed flask (25-35 mL) equipped with a distillation head and nitrogen bubbler. The mixture was heated for 1 h at 150-160° C. (oil bath) while allowing liberated methanol to distill from the reaction vessel. The mixture then was heated at 180° C. for 1 h while continuing to allow the methyl lactate to distill from the reaction flask. The reaction mixture then was heated at 150-160° C. under vacuum (1.3 kPa) for an hour to remove any remaining methyl lactate. The resulting enol ethers were isolated by short-path, vacuum distillation from the reaction flask.

Following this general procedure and using the methyl enol ether prepared from 4-(4-methoxyphenyl)butan-2-one, the title compound was isolated by short-path distillation of the crude reaction mixture (bp 128-132° C., 1 Pa) in 61% yield as a colorless liquid (E/Z=57:43).

$^1$H NMR ($CDCl_3$, 500 MHz): δ 1.41$_Z$ and 1.43$_E$ (both d, J=6.9 Hz, 3H), 1.54$_Z$ and 1.70$_E$ (both s, 3H), 2.13$_E$ (t, J=7.9 Hz) and 2.31-2.38$_Z$ (m) and 2.41-2.48$_Z$ (m) (2H), 2.57-2.71 (m, 2H), 3.73$_E$ and 3.74$_Z$ (both s, 3H), 3.77$_E$ and 3.78$_Z$ (s, 3H), 4.10$_Z$ and 4.15$_E$ (both q, J=6.9 Hz, 1H), 5.77$_E$ and 5.80$_Z$ (both s, 1H), 6.79-6.83 (m, 2H), 7.06$_E$ and 7.14$_Z$ (both d, J=8.6 Hz, 2H).

$^{13}$C NMR ($CDCl_3$, 125.8 MHz, E-isomer): δ 13.2 ($CH_3$), 18.2 ($CH_3$), 33.8 ($CH_2$), 36.3 ($CH_2$), 52.1 ($CH_3$), 55.2 ($CH_3$), 75.4 (CH), 113.7 (CH), 116.4 (C), 129.3 (CH), 134.2 (C), 139.1 (CH), 157.7 (C), 172.8 (C).

Compound 18. (±)-methyl 2-((2-pentylcyclopentylidene)methoxy)propanoate

Following the procedure described for compound 17 and starting from the methyl enol ether prepared from 2-pentylcyclopentanone, the title compound was isolated by short-path distillation of the crude reaction mixture (bp 85-88° C., 1 Pa) in 74% yield as a colorless liquid (mixture of diastereomer, E/Z=57:43).

$^1$H NMR ($CDCl_3$, 600 MHz): δ 0.88 (t, J=7.0 Hz, 3H), 1.15-1.40 (m, 8H), 1.40-1.56 (m, 1.5 H), 1.45, 1.466 and 1.467 (overlapping d, J=7.0 Hz, 3H), 1.61-1.75 (m, 1.5 H), 1.75-1.87 (m, 1H), 2.06-2.16 (m, 1H), 2.16-2.41 and 2.41-2.50 (both m, 1.6H), 2.62-2.72 and 2.72-2.81 (both m, 0.4H), 3.74, 3.75 and 3.753 (overlapping s, 3H), 4.16, 4.18 and 4.22 (overlapping q, J=7.0 Hz, 1H) 5.85$_E$, 5.92$_Z$ and 5.94$_Z$ (both s, 1H).

$^{13}$C NMR ($CDCl_3$, 150.9 MHz): δ 14.11 ($CH_3$), 14.14 ($CH_3$), 14.16 ($CH_3$), 18.23 ($CH_3$), 18.28 ($CH_3$), 18.31 ($CH_3$), 22.69 ($CH_2$), 22.71 ($CH_2$), 24.12 ($CH_2$), 24.15 ($CH_2$), 25.13 ($CH_2$), 25.21 ($CH_2$), 27.32 ($CH_2$), 27.37 ($CH_2$), 27.40 ($CH_2$), 27.44 ($CH_2$), 27.54 ($CH_2$), 29.36 ($CH_2$), 29.44 ($CH_2$), 32.02 ($CH_2$), 32.06 ($CH_2$), 32.10 ($CH_2$), 32.11 ($CH_2$), 32.37 ($CH_2$), 33.14 ($CH_2$), 33.19 ($CH_2$), 33.7 ($CH_2$), 33.9 ($CH_2$), 34.8 ($CH_2$), 34.9 ($CH_2$), 39.5 (CH), 39.6 (CH), 41.41 (CH), 41.44 (CH), 51.9 ($CH_3$), 52.03 ($CH_3$), 52.04 ($CH_3$), 52.07 ($CH_3$), 75.4 (CH), 75.54 (CH), 75.56 (CH), 127.3 (C), 127.9 (C), 128.1 (C), 128.2 (C), 135.76 (CH), 135.78 (CH), 136.1 (CH), 136.2 (CH), 172.8 (C), 172.9 (C), 172.99 (C), 173.01 (C).

Compound 19. (±)-methyl 2-((2-ethyl-4,4-dimethylcyclohexylidene)methoxy)propanoate Following the procedure described for compound 17 and starting from the methyl enol ether prepared from 2-ethyl-4,4-dimethylcyclohexanone, the title compound was isolated by short-path distillation of the crude reaction mixture (bp 86-88° C., 1 Pa) in 71% yield as a colorless liquid (mixture of diastereomer, E/Z=80:20).

$^1$H NMR ($CDCl_3$, 500 MHz): δ 0.79-094 (m, 7H), 0.96$_E$ and 0.97$_Z$ (s, 3H), 1.07-1.28 (m, 2H), 1.29-1.43 (m, 1H), 1.43$_Z$, 1.44$_Z$ and 1.46$_E$ (all d, J=6.9 Hz, 3H), 1.49-1.62 (m, 2H), 1.66-185 (m, 1H), 1.86-1.96 (m, 0.8H), 1.99-2.11 (m, 0.2H), 2.51-2.58$_Z$ and 2.60-2.67$_Z$ (both m, 0.2H), 2.74$_E$ and 2.77$_E$ (both q, J=4.0 Hz, 0.8H), 3.74, 3.748 and 3.75 (overlapping s, 3H), 4.12-4.22 (overlapping q, J=6.9 Hz, 1H), 5.69$_E$ and 5.83$_Z$ (both s, 1H).

$^{13}$C NMR ($CDCl_3$, 125.8 MHz, E-isomers): δ 11.95 ($CH_3$), 11.97 ($CH_3$), 18.17 ($CH_3$), 18.2 ($CH_3$), 22.2 ($CH_2$), 24.7 ($CH_2$), 25.3 ($CH_3$), 25.4 ($CH_3$), 30.89 (C), 30.91 (C), 32.46 ($CH_3$), 32.50 ($CH_3$), 37.5 (CH), 37.6 (CH), 40.1 ($CH_2$), 47.0 ($CH_2$), 47.1 ($CH_2$), 51.98 ($CH_3$), 52.05 ($CH_3$), 75.56 (CH), 75.65 (CH), 125.2 (C), 125.4 (C), 135.13 (CH), 135.14 (CH), 172.85 (C), 172.93 (C).

Compound 20. (±)-methyl 2-((2-(4-methoxyphenyl)prop-1-en-1-yl)oxy)propanoate

Following the procedure described for compound 17 and starting from the methyl enol ether prepared from acetanisole, the title compound was isolated by short-path distillation of the crude reaction mixture (bp 126-129° C., 1 Pa) in 65% yield as a colorless liquid (E/Z=78:22).

$^1$H NMR ($CDCl_3$, 600 MHz): δ 1.52$_Z$ and 1.53$_E$ (both d, J=7.0 Hz, 3H), 1.89$_Z$ and 2.02$_E$ (both s, 3H), 3.76 (s, 3H), 3.78$_E$ and 3.80$_Z$ (both s, 3H), 4.32$_Z$ and 4.36$_E$ (both q, J=7.0 Hz, 1H), 6.08$_Z$ and 6.34$_E$ (both s, 1H), 6.83$_E$ and 6.87$_Z$ (both d, J=8.8 Hz, 2H), 7.22$_E$ and 7.64$_Z$ (both d, J=8.8 Hz, 2H).

$^{13}$C NMR ($CDCl_3$, 150.9 MHz, E-isomer): δ 13.1 ($CH_3$), 18.3 ($CH_3$), 52.2 ($CH_3$), 55.3 ($CH_3$), 76.0 (CH), 113.8 (CH), 116.7 (C), 126.3 (CH), 132.8 (C), 140.8 (CH), 158.3 (C), 172.5 (C).

Compound 21. (±)-methyl 2-((2-(naphthalen-2-yl)prop-1-en-1-yl)oxy)propanoate

Following the procedure described for compound 17 and starting from the methyl enol ether prepared from 1-(naphthalen-2-yl)ethan-1-one, the title compound was isolated by silica gel flash chromatography in 71% yield as a white solid (E/Z=94:6).

$^1$H NMR ($CDCl_3$, 500 MHz): δ 1.54$_Z$ and 1.57$_E$ (both d, J=6.9 Hz, 3H), 2.03$_Z$ and 2.15$_E$ (both s, 3H), 3.78 (s, 3H), 4.37$_Z$ and 4.43$_E$ (both q, J=6.9 Hz, 1H), 6.22$_Z$ and 6.59$_E$ (both s, 1H), 7.37-7.50 (m, 3H), 7.67-7.80 (m, 4H).

$^{13}$C NMR ($CDCl_3$, 125.8 MHz, E-isomer): (δ 12.8 ($CH_3$), 18.3 ($CH_3$), 52.3 ($CH_3$), 76.1 (C), 116.8 (C), 123.4 (CH), 123.8 (CH), 125.2 (CH), 126.1 (CH), 127.5 (CH), 127.7 (CH), 127.75 (CH), 132.2 (C), 133.6 (C), 137.5 (C), 142.5 (CH), 172.4 (C).

Compound 22. (±)-methyl 2-((2-(p-tolyl)prop-1-en-1-yl)oxy)propanoate

Following the procedure described for compound 17 and starting from the methyl enol ether prepared from para-methylacetophenone, the title compound was isolated by short-path distillation of the crude reaction mixture (bp 98-104° C., 1 Pa) in 79% yield as a colorless liquid (E/Z=82:18).

$^1$H NMR ($CDCl_3$, 500 MHz): δ $1.51_Z$ and $1.54_E$ (both d, J=6.9 Hz, 3H) $1.90_Z$ and $2.03_E$ (both s, 3H), $2.32_E$ and $2.33_Z$ (both s, 3H), 3.76 (s, 3H), $4.32_Z$ and $4.37_E$ (both q, J=6.9 Hz, 1H), $6.10_Z$ and $6.39_E$ (both s, 1H), $7.09_E$ and $7.13_Z$ (both d, J=8.1 Hz, 2H), $7.19_E$ and $7.57_Z$ (both d, J=8.1 Hz, 2H).

$^{13}$C NMR ($CDCl_3$, 125.8 MHz, E-isomer): (δ 13.0 ($CH_3$), 18.3 ($CH_3$), 21.0 ($CH_3$), 52.2 ($CH_3$), 76.0 (C), 116.9 (C), 125.2 (CH), 129.0 (CH), 135.8 (C), 137.4 (C), 141.3 (C), 172.5 (C).

Compound 23. methyl 2-methyl-2-((2-methyldec-1-en-1-yl)oxy)propanoate

General Procedure: A dimethyl acetal (40 mmol), methyl 2-hydroxyisobutyrate (120 mmol), and $KHSO_4$ (1.2 mmol) were added to a 25-35 ml, round-bottomed flask equipped with a Vigreux column (10 cm), distillation head and nitrogen bubbler. The reaction flask was placed in a 150° C. oil bath that was immediately heated to 180° C. Methanol and excess 2-hydroxyisobutyrate were allowed to distill from the reaction vessel. After 1 h, the Vigreux column was removed and heating continued for another 0.5-1 h. The resulting enol ethers were isolated by short-path, vacuum distillation from the reaction flask.

Following the general procedure described above and starting from the dimethyl acetal of 2-methyldecanal (8 g, 37 mmol), methyl 2-hydroxyisobutyrate (17.4 g, 148 mmol), and $KHSO_4$ (0.15 g, 1.10 mmol), the title compound (5.0 g, 50% yield) was isolated by short-path, vacuum distillation (bp 96-100° C., 2 Pa) as a colorless oil (E/Z=62:38).

$^1$H NMR ($CDCl_3$, 500 MHz): δδ $0.878_E$ and $0.882_Z$ (both t, J=7.0 Hz, 3H), 1.17-1.40 (m, 12H), $1.45_Z$ and $1.47_E$ (both s, 6H), $1.52_Z$ and $1.60_E$ (both d, J=1.2 Hz, 3H), $1.86_E$ and $2.08_Z$ (both t, J=7.4 Hz, 2H), $3.74_Z$ and $3.75_E$ (both s, 3H), $5.81_Z$ and $5.83_E$ (both s, 1H).

$^{13}$C NMR ($CDCl_3$, 125 MHz): δ 13.0 ($CH_3$), 14.1 ($CH_3$), 22.7 ($CH_2$), 25.0 ($CH_3$), 27.9 ($CH_2$), 29.1 ($CH_2$), 29.3 ($CH_2$), 29.5 ($CH_2$), 31.9 ($CH_2$), 34.0 ($CH_2$), 52.2 ($CH_3$), 78.5 (C), 118.8 (C), 134.7 (C), 174.6 (C).

Compound 24. methyl 2-((3-(4-methoxyphenyl)-2-methylprop-1-en-1-yl)oxy)-2-methylpropanoate Following the procedure described for compound 23 and starting from the dimethyl acetal of 3-(4-methoxyphenyl)-2-methylpropanal (6 g, 26.8 mmol), methyl 2-hydroxyisobutyrate (9.48 g, 80.3 mmol), and $KHSO_4$ (0.11 g, 0.8 mmol), the title compound (6.47 g, 87% yield) was isolated by short-path, vacuum distillation (bp 122-125° C., 1 Pa) as a colorless oil (E/Z=60:40).

$^1$H NMR ($CDCl_3$, 500 MHz): δ $1.45_Z$ and $1.52_E$ (both s, 3H), $1.50_E$ and $1.51_Z$ (both s, 6H), $3.12_Z$ and $3.37_E$ (both s, 2H), $3.75_E$ and $3.76_Z$ (both s, 3H), 3.78 (s, 3H), $5.95_Z$ and $6.00_E$ (both s, 1H), 6.81 (d, J=8.4 Hz, 2H), $7.07_E$ and $7.12_Z$ (both d, J=8.4 Hz, 2H).

$^{13}$C NMR ($CDCl_3$, 125.8 MHz, E-isomer): δ 12.9 ($CH_3$), 25.0 ($CH_3$), 39.6 ($CH_2$), 52.3 ($CH_3$), 55.2 ($CH_3$), 78.7 (C), 113.6 (CH), 118.0 (C), 129.5 (CH), 132.1 (C), 136.0 (CH), 157.9 (C), 174.4 (C).

Compound 25. methyl 2-methyl-2-((2 phenylprop-1-en-1-yl)oxy)propanoate

Following the procedure described for compound 23 and starting from the dimethyl acetal of 2-phenylpropanal (10 g, 55.5 mmol), methyl 2-hydroxyisobutyrate (19.7 g, 166 mmol), and $KHSO_4$ (0.23 g, 1.7 mmol), the title compound (11.0 g, 85% yield) was isolated by short-path, vacuum distillation (bp 88-92° C., 1.3 Pa) as a colorless oil (E/Z=85:15).

$^1$H NMR ($CDCl_3$, 500 MHz): δ $1.54_Z$ and $1.56_E$ (both s, 6H), $1.93_Z$ and $2.03_E$ (both s, 3H), $3.74_Z$ and $3.77_E$ (both s, 3H), $6.21_Z$ and $6.50_E$ (both s, 1H), 7.15-7.21 (m, 1H), 7.24-7.34 and 7.64-7.67 (both m, 4H).

$^{13}$C NMR ($CDCl_3$, 125.8 MHz, E-isomer): (δ 12.8 ($CH_3$), 25.2 ($CH_3$), 52.4 ($CH_3$), 79.3 (C), 117.7 (C), 125.3 (CH), 126.1 (CH), 128.3 (CH), 138.4 (CH), 140.7 (C), 174.1 (C).

Compound 26. methyl 2-methyl-2-((2-methyl-4 phenylbut-1-en-1-yl)oxy)propanoate Following the procedure described for compound 23 and starting from the dimethyl acetal of 2-methyl-4-phenylbutanal (9 g, 43.2 mmol), methyl 2-hydroxyisobutyrate (15.3 g, 130 mmol), and $KHSO_4$ (0.18 g, 1.3 mmol), the title compound (9.28 g, 82% yield) was isolated by short-path, vacuum distillation (bp 88-91° C., 1 Pa) as a colorless oil (E/Z=58:42).

$^1$H NMR ($CDCl_3$, 500 MHz): δ $1.39_Z$ and $1.40_E$ (both s, 6H), $1.56_Z$ and $1.67_E$ (both s, 3H), $2.16\text{-}2.22_E$ and $2.38\text{-}2.44_Z$ (both m, 2H), 2.65-2.72 (m, 2H), $3.71_E$ and $3.73_Z$ (both s, 3H), $5.79_E$ and $5.84_Z$ (both s, 1H), 7.12-7.19 (m, 2H), 7.19-7.28 (m, 3H).

$^{13}$C NMR ($CDCl_3$, 125.8 MHz, E-isomer): δ 13.1 ($CH_3$), 24.9 ($CH_3$), 34.6 ($CH_2$), 36.1 ($CH_2$), 52.2 ($CH_3$), 78.5 (C), 117.2 (C), 125.7 (CH), 128.2 (CH), 128.4 (CH), 135.5 (CH), 142.1 (C), 174.4 (C).

Compound 27. methyl 2-((2-(4-methoxyphenyl) prop-1-en-1-yl)oxy)-2-methylpropanoate General procedure: Methoxymethyltriphenylphosphonium chloride (15.1 g, 44.1 mmol) and the ketone (29.4 mmol) were added to 120 ml of toluene. Potassium t-butoxide (5.27 g, 47 mmol) was added to the stirring slurry in 4 portions every 15 min. The mixture was stirred for 4 h becoming a deep red color. It then was poured into 500 ml of water and extracted with EtOAc (3×250 mL). The organic phases were combined, dried over $Na_2SO_4$, filtered and concentrated to a grainy solid. The resulting methyl enol ether product was isolated by flash chromatography (silica gel, hexane) followed by bulb-to-bulb distillation. Alternatively, the solid was washed with hexane and filtered. Concentrating the filtrate afforded the crude methyl enol ether that was purified by fractional distillation. The methyl enol ether (30-40 mmol) then was combined with methyl 2-hydroxyisobutyrate (3 equiv) and $KHSO_4$ (3 mole %) in a round-bottomed flask (25-35 mL) equipped with a Vigreux column (10 cm), distillation head and nitrogen bubbler. The reaction flask was placed in a 150° C. oil bath that was then heated to 180° C. Methanol and excess 2-hydroxyisobutyrate were allowed to distill from the reaction vessel. After 1 h, the Vigreux column was removed and heating continued for another 0.5-1 h. The resulting enol ethers were isolated by short-path, vacuum distillation from the reaction flask.

Following this general procedure and using the methyl enol ether prepared from acetanisole, the title compound was isolated by short-path distillation of the crude reaction mixture (bp 118-121° C., 1.2 Pa) in 78% yield as a colorless liquid (E/Z=78:22).

$^1$H NMR ($CDCl_3$, 600 MHz): δ $1.54_Z$ and $1.55_E$ (both s, 6H), $1.90_Z$ and $2.00_E$ (both s, 3H), 3.77 (s, 3H), $3.78_E$ and $3.80_Z$ (both s, 3H), $6.14_Z$ and $6.40_E$ (both s, 1H), $6.83_E$ and $6.86_Z$ (both d, J=8.6 Hz, 2H), $7.22_E$ and $7.62_Z$ (both d, J=8.6 Hz, 2H).

$^{13}$C NMR ($CDCl_3$, 150.9 MHz, E-isomer): δ 13.1 ($CH_3$), 25.2 ($CH_3$), 52.4 ($CH_3$), 55.3 ($CH_3$), 79.2 (C), 113.7 (CH), 117.6 (C), 126.4 (CH), 133.2 (C), 137.2 (CH), 158.2 (C), 174.2 (C).

Compound 28. (±)-methyl 2-methyl-2-((2-(p-tolyl) prop-1-en-1-yl)oxy)propanoatemethyl Following the procedure described for compound 27 and starting from the methyl enol ether prepared from para-methylacetophenone, the title compound was isolated by short-path distillation of the crude reaction mixture (bp 94-98° C., 1 Pa) in 81% yield as a colorless liquid (E/Z=83:17).

$^1$H NMR ($CDCl_3$, 500 MHz): δ $1.53_Z$ and $1.55_E$ (both s, 6H), $1.91_Z$ and $2.00_E$ (both s, 3H), $2.32_E$ and $2.33_Z$ (both s, 3H), 3.76 (s, 3H), $6.17_Z$ and $6.45_E$ (both s, 1H), $7.09_E$ and $7.12_Z$ (both d, J=8.2 Hz, 2H), $7.19_E$ and $7.55_Z$ (both d, J=8.2 Hz, 2H).

$^{13}$C NMR ($CDCl_3$, 125.8 MHz, E-isomer): δ 12.9 ($CH_3$), 21.0 ($CH_3$), 25.2 ($CH_3$), 52.4 ($CH_3$), 79.3 (C), 117.7 (C), 125.2 (CH), 129.0 (CH), 135.8 (C), 137.8 (C), 137.8 (CH), 174.2 (C).

Compound 29. (±)-methyl 2-methyl-2-((2-pentylcyclopentylidene)methoxy)propanoate Following the procedure described for compound 27 and starting from the methyl enol ether prepared from 2-pentylcyclopentanone, the title compound was isolated by short-path distillation of the crude reaction mixture (bp 90-92° C., 1 Pa) in 84% yield as a colorless liquid (E/Z=68:32).

$^1$H NMR ($CDCl_3$, 500 MHz): δ $0.88_E$ and $0.89_Z$ (both t, J=7.0 Hz, 3H), 1.14-1.38 (m, 8H), 1.38-1.56 (m, 1.5 H), 1.61-1.76 (m, 1.5 H), 1.76-1.85 (m, 1H), $1.46_Z$ and $1.47_E$ (both s, 6H), 2.10-2.20 (m, 0.7H), 2.20-2.42 (m, 2H), 2.64-2.73 (m, 0.3H), $3.74_Z$ and $3.75_E$ (both s, 3H), $5.87_E$ and $5.95_Z$ (both s, 1H).

$^{13}$C NMR ($CDCl_3$, 125.8 MHz, E-isomer): (δ 14.1 ($CH_3$), 22.7 ($CH_2$), 24.1 ($CH_2$), 25.0 ($CH_3$), 25.2 ($CH_3$), 27.4 ($CH_2$), 27.5 ($CH_2$), 32.1 ($CH_2$), 33.1 ($CH_2$), 34.9 ($CH_2$), 41.5 (CH), 52.2 ($CH_3$), 78.5 (C), 129.4 (C), 132.4 (CH), 174.6 (C).

Compound 30. (±)-methyl 2-(undeca-1,10-dien-1-yloxy)propanoate

Following the procedure described for compound 8 and starting from the dimethyl acetal of 10-undecenal (12 g, 56 mmol), (±)-methyl lactate (23.3 g, 224 mmol), and $KHSO_4$ (0.23 g, 1.7 mmol), the title compound (4.53 g, 32% yield) was isolated by short-path distillation (bp 92-96° C., 1.3 Pa) as a colorless oil (E/Z=43:57).

$^1$H NMR ($CDCl_3$, 500 MHz): δ 1.23-1.42 (m, 10), $1.46_E$ and $1.47_Z$ (both d, J=6.9 Hz, 3H), $1.89_E$ (q, J=7.0 Hz, 0.9H), 2.04 (q, J=7.2 Hz, 2H), $2.12_Z$ (q, J=7.1 Hz, 1.1H), $3.75_Z$ and $3.76_E$ (s, 3H), $4.24_Z$ and $4.32_E$ (q, J=6.9 Hz, 1H), $4.46_Z$ (q, J=6.5 Hz, 0.6H), $4.85_E$ (dt, J=12.5, 7.3 Hz, 0.4H), 4.92 (d, J=10.3 Hz, 1H), 4.99 (d, J=17.2 Hz, 1H), 5.76-5.85 (m, 1H), $5.90_Z$ (d, J=6.3 Hz, 0.6 H), 6.14 (d, J=12.5 Hz, 0.4H).

$^{13}$C NMR ($CDCl_3$, 125.8 MHz, Z-isomer): δ 18.1 ($CH_3$), 23.9 ($CH_2$), 28.96 ($CH_2$), 29.14 ($CH_2$), 29.2 ($CH_2$), 29.3 ($CH_2$), 29.6 ($CH_2$), 33.8 ($CH_2$), 52.1 ($CH_3$), 75.6 (CH), 109.5 (CH), 114.1 ($CH_2$), 139.2 (CH), 142.9 (CH), 172.6 (C).

Compound 31. (±)-methyl 2-(tridec-1-en-1-yloxy)propanoate

The title compound was prepared following the procedure described for compound 8 and starting from the dimethyl acetal of tridecanal (7.0 g, 28.6 mmol), (±)-methyl lactate (11.9 g, 115 mmol), and $KHSO_4$ (0.12 g, 0.86 mmol). The crude reaction mixture was poured into sat. aqueous $NaHCO_3$ and extracted with ethyl acetate. The organic phase was dried over $MgSO_4$, filtered and concentrated. The crude product was subjected to silica gel flash chromatography (hexane/EtOAc 100:0 to 95:5) followed by bulb-to-bulb distillation to afford the title compound (1.4 g, 17% yield) as a colorless liquid (E/Z=50:50).

$^1$H NMR ($CDCl_3$, 500 MHz): (δ 0.88 (t, J=6.9 Hz, 3H), 1.19-1.40 (m, 18H), 1.465 and 1.475 (both d, J=6.9 Hz, 3H), 1.89 and 2.12 (both q, J=7.0 Hz, 2H), 3.75 and 3.76 (both s, 3H), 4.24 and 4.31 (both q, J=6.9 Hz, 1H), $4.46_Z$ (q, J=7.0 Hz, 0.5H), $4.86_E$ (dt, J=12.5, 7.3 Hz, 0.5H), $5.90_Z$ (d, J=6.3 Hz, 0.5H), $6.13_E$ (d, J=12.5 Hz, 0.5H).

$^{13}$C NMR ($CDCl_3$, 125.8 MHz): δ 14.1 ($CH_3$), 18.14 ($CH_3$), 18.17 ($CH_3$), 22.7 ($CH_2$), 23.9 ($CH_2$), 27.6 ($CH_2$), 29.0 ($CH_2$), 29.3 ($CH_2$), 29.37 ($CH_2$), 29.38 ($CH_2$), 29.48 ($CH_2$), 29.54 ($CH_2$), 29.66 ($CH_2$), 29.67 ($CH_2$), 29.68 ($CH_2$), 29.69 ($CH_2$), 29.72 ($CH_2$), 30.4 ($CH_2$), 31.9 ($CH_2$), 52.08 ($CH_3$), 52.14 ($CH_3$), 73.7 (CH), 75.6 (CH), 107.2 (CH), 109.6 (CH), 142.8 (CH), 144.2 (CH), 172.6 (C), 172.7 (C).

Compound 32. (±)-methyl 2-(dodeca-1,11-dien-1-yloxy)propanoate

General procedure: Methoxymethyltriphenylphosphonium chloride (15.1 g, 44.1 mmol) and the aldehyde (29.4 mmol) were added to 120 ml of toluene. Potassium t-butoxide (5.27 g, 47 mmol) was added to the stirring slurry in 4 portions every 15 min. The mixture was stirred for 4 h becoming a deep red color. It then was poured into 500 ml of water and extracted with EtOAc (3×250 mL). The organic phases were combined, dried over $Na_2SO_4$, filtered and concentrated to a grainy solid. The resulting methyl enol ether product was isolated by flash chromatography (silica gel, hexane) followed by bulb-to-bulb distillation. Alternatively, the solid was washed with hexane and filtered. Concentrating the filtrate afforded the crude methyl enol ether that was purified by fractional distillation. The methyl enol ether (30-40 mmol) then was combined with (±)-methyl lactate (3-4 equiv) and $KHSO_4$ (0.03 equiv) in a round-bottomed flask (25-35 mL) equipped with a distillation head and nitrogen bubbler. The mixture was heated at 140° C. (oil bath) while allowing liberated methanol to distill from the reaction vessel. After 1 h, the reaction vessel was placed under vacuum (60 kPa) and the pressure reduced to 40 kPa while allowing methyl lactate to distill from the flask. After 1 h, the pressure was progressively reduced to 40 Pa, over 1-1.5 hours. Following this 0.5 g of $Na_2CO_3$ was added and the resulting enol ether was isolated by short-path, vacuum distillation from the reaction flask.

Following this general procedure and using the methyl enol ether prepared from 10-undecanal (8.0 g, 40.7 mmol), (±)-methyl lactate (17 g, 163 mmol) and $KHSO_4$ (0.17 g, 1.22 mmol), the title compound (4.21 g, 38% yield) was isolated after consecutive, short-path distillations (bp 94-96° C., 1 Pa) as a colorless oil (E/Z=43:57).

$^{1}$H NMR ($CDCl_3$, 500 MHz): δ 1.21-1.42 (m, 12), $1.46_E$ and $1.47_Z$ (both d, J=6.9 Hz, 3H), $1.88_E$ (q, J=7.0 Hz, 0.9H), 2.04 (q, J=7.3 Hz, 2H), $2.11_Z$ (q, J=7.1 Hz, 1.1H), $3.75_Z$ and $3.76_E$ (s, 3H), $4.24_Z$ and $4.31_E$ (q, J=6.9 Hz, 1H), $4.46_Z$ (q, J=6.9 Hz, 0.6H), $4.86_E$ (dt, J=12.5, 7.4 Hz, 0.4H), 4.93 (d, J=10.4 Hz, 1H), 4.99 (d, J=17.0 Hz, 1H), 5.76-5.86 (m, 1H), $5.90_Z$ (d, J=6.2 Hz, 0.6 H), 6.13 (d, J=12.5 Hz, 0.4H).

$^{13}$C NMR ($CDCl_3$, 125.8 MHz): δ 18.1 ($CH_3$), 18.2 ($CH_3$), 23.9 ($CH_2$), 27.5 ($CH_2$), 28.94 ($CH_2$), 28.96 ($CH_2$), 29.13 ($CH_2$), 29.16 ($CH_2$), 29.24 ($CH_2$), 29.4 ($CH_2$), 29.45 ($CH_2$), 29.46 ($CH_2$), 29.5 ($CH_2$), 29.6 ($CH_2$), 30.3 ($CH_2$), 33.82 ($CH_2$), 33.83 ($CH_2$), 52.1 ($CH_3$), 52.14 ($CH_3$), 73.7 (CH), 75.6 (CH), 107.2 (CH), 109.6 (CH), 114.08 ($CH_2$), 114.11 ($CH_2$), 139.2 (CH), 139.3 (CH), 142.9 (CH), 144.2 (CH), 172.6 (C), 172.7 (C).

Compound 33. (±)-methyl 2-((3-methyldodec-1-en-1-yl)oxy)propanoate

Following the procedure described for compound 32 and using the methyl enol ether prepared from 2-methylundecanal (9.0 g, 42.4 mmol), (±)-methyl lactate (17.6 g, 170 mmol) and $KHSO_4$ (0.17 g, 1.27 mmol), the title compound (5.52 g, 45% yield) was isolated after consecutive, short-path distillations (bp 93-98° C., 1 Pa) as a colorless oil (mixture of diastereomers, E/Z=40:60).

$^{1}$H NMR ($CDCl_3$, 500 MHz): δ 0.88 (bt, J=6.9 Hz, 3H), 0.93-0.97 (overlapping d, 3H), 1.14-1.34 (m, 16H), $1.46_Z$ and $1.47_E$ (both d, J=6.9 Hz, 3H), $1.94\text{-}2.04_E$ (m, 0.4H), $2.61\text{-}2.74_Z$ (m, 0.6H), 3.74, 3.75 and 3.76 (all s, 3H), $4.22_Z$ and $4.23_Z$ (both q, J=6.9 Hz, 0.6H), $4.26_Z$ (dd, J=9.5, 6.3, 0.6H), $4.31_E$ and $4.32_E$ (both q, J=6.9 Hz, 0.4H), $4.71_E$ and $4.73_E$ (both dd, J=12.6, 8.5 Hz, 0.4H), 5.86 (d, 6.3 Hz, 0.6H), $6.10_E$ and $6.12_E$ (both d, J=12.6 Hz, 0.4H).

$^{13}$C NMR ($CDCl_3$, 125.8 MHz): δ 14.1 ($CH_3$), 18.09 ($CH_3$), 18.13 ($CH_3$), 18.16 ($CH_3$), 21.2 ($CH_3$), 21.3 ($CH_3$), 21.7 ($CH_3$), 21.8 ($CH_3$), 22.7 ($CH_2$), 27.31 ($CH_2$), 27.32 ($CH_2$), 27.35 ($CH_2$), 27.42 ($CH_2$), 28.88 (CH), 28.91 (CH), 9.37 ($CH_2$), 29.39 ($CH_2$), 29.41 ($CH_2$), 29.67 ($CH_2$), 29.69 ($CH_2$), 29.71 ($CH_2$), 29.74 ($CH_2$), 29.77 ($CH_2$), 29.87 ($CH_2$), 31.93 ($CH_2$), 31.95 ($CH_2$), 31.96 ($CH_2$), 32.7 (CH), 32.8 (CH), 37.56 ($CH_2$), 37.58 ($CH_2$), 37.76 ($CH_2$), 37.78 ($CH_2$), 52.01 ($CH_3$), 52.05 ($CH_3$), 52.09 ($CH_3$), 52.1 ($CH_3$), 73.6 (CH), 73.8 (CH), 75.67 (CH), 75.7 (CH), 113.4 (CH), 113.6 (CH), 115.9 (CH), 116.1 (CH), 1419. (CH), 142.0 (CH), 143.12 (CH), 143.14 (CH), 172.5 (C), 172.6 (C), 172.7 (C), 172.8 (C).

Compound 34. (±)-methyl 2-((4 phenylpent-1-en-1-yl)oxy)propanoate

Following the procedure described for compound 32 and using the methyl enol ether prepared from 3-phenylbutanal (8.0 g, 45.4 mmol), (±)-methyl lactate (16.5 g, 159 mmol) and $KHSO_4$ (0.19 g, 1.36 mmol), the title compound (3.58 g, 31% yield) was isolated by short-path distillation (bp 108-110° C., 1.3 Pa) as a colorless oil (mixture of diastereomers, E/Z=43:57).

$^{1}$H NMR ($CDCl_3$, 500 MHz): δ 1.20-2.16 (overlapping d, 3H), 1.41-1.47 (overlapping d, 3H), $2.07\text{-}2.16_E$ (m, 0.4H), $2.16\text{-}2.25_E$ (m, 0.4H), $2.34\text{-}2.51_Z$ (m, 1.2H), $264\text{-}2.72_E$ (m, 0.4H), $2.72\text{-}2.82_Z$ (m, 0.6H), $3.707_E$, $3.714_E$, $3.73_Z$ and $3.74_Z$ (all s, 3H), $4.17_Z$, $4.21_Z$, $4.257_E$ and $4.259_E$ (all q, J=6.9 Hz, 1H), $4.34\text{-}4.41_Z$ (m, 0.6H), $4.71\text{-}4.80_E$ (m, 0.4H), $5.89_Z$ and $5.91_Z$ (both d, J=6.3 Hz, 0.6H), $6.09_E$ and $6.11_E$ (both d, J=12.6 Hz, 0.4H), 7.13-7.30 (m, 5H).

$^{13}$C NMR ($CDCl_3$, 125.8 MHz): δ 18.1 ($CH_3$), 21.7 ($CH_3$), 21.9 ($CH_3$), 32.3 ($CH_2$), 32.4 ($CH_2$), 39.9 (CH), 40 (CH), 52.1 ($CH_3$), 75.6 (CH), 107.3 (CH), 107.4 (CH), 125.8 (CH), 127.0 (CH), 128.3 (CH), 143.6 (CH), 147.3 (C), 172.5 (C).

Compound 35. (±)-methyl 2-((4-methoxystyryl)oxy)propanoate

Following the procedure described for compound 32 and using the methyl enol ether prepared from para-anisaldehyde (8.5 g, 51.8 mmol), (±)-methyl lactate (16.2 g, 155 mmol) and $KHSO_4$ (0.21 g, 1.55 mmol), the title compound (3.96 g, 32% yield) was isolated by short-path distillation (bp 128-131° C., 1 Pa) as a colorless oil (E/Z=47:53).

$^{1}$H NMR ($CDCl_3$, 500 MHz): δ $1.53_E$ and $1.58_Z$ (both d, J=6.9 Hz, 3H), $3.768_Z$ and $3.773_E$ (both s, 3H), $3.78_E$ and $3.79_Z$ (both s, 3H), $4.40_Z$ and $4.46_E$ (both q, J=6.9 Hz, 1H), $5.26_Z$ (d, J=7.0 Hz, 0.5H), $5.91_E$ (d, J=12.9 Hz, 0.5H), $6.08_Z$ (d, J=7.0 Hz, 0.5H), $6.76_E$ (d, J=12.9 Hz, 0.5H), $6.80_E$ and $6.84_Z$ (both d, J=8.9 Hz, 2H), $7.13_E$ and $7.574_Z$ (both d, J=8.9 Hz, 2H).

$^{13}$C NMR ($CDCl_3$, 125.8 MHz, Z-isomer): (δ 18.3 ($CH_3$), 52.2 ($CH_3$), 55.2 ($CH_3$), 76.7 (CH), 106.9 (CH), 113.6 (CH), 128.3 (C), 129.7 (CH), 142.9 (CH), 157.8 (C), 172.1 (C).

Compound 36. (±)-methyl 2-((3,4-dimethoxystyryl)oxy)propanoate

Following the procedure described for compound 32, the title compound was prepared using the methyl enol ether prepared from 3,4-dimethoxybenzaldehyde (7.5 g, 38.6 mmol), (±)-methyl lactate (16.1 g, 154 mmol) and $KHSO_4$ (0.16 g, 1.16 mmol). The crude reaction mixture was poured into sat. aqueous $NaHCO_3$ and extracted with ethyl acetate. The organic phase was dried over $MgSO_4$, filtered and concentrated. The crude product was filtered through a bed of silica gel (hexane/EtOAc 50:50) and then subjected to bulb-to-bulb distillation (200° C., 2.7 Pa) to afford the title compound (1.3 g, 13% yield) as a colorless liquid (E/Z=41:59).

$^{1}$H NMR ($CDCl_3$, 500 MHz): δ $1.55_E$ and $1.59_Z$ (both d, J=6.8 Hz, 3H), $3.77_Z$ and $3.79_E$ (both s, 3H), $3.85_E$ and $3.87_Z$ (both s, 3H), $3.87_E$ and $3.89_Z$ (both s, 3H), $4.42_Z$ and $4.48_E$ (both q, J=6.8 Hz, 1H), $5.28_Z$ (d, J=7.0 Hz, 0.6H), $5.91_E$ (d, J=12.9 Hz, 0.4H), $6.11_Z$ (d, J=7.0 Hz, 0.6H), 6.72-6.84 (m, 2.2H), $7.06_Z$ (dd, J=8.3, 2.0 Hz, 0.6H), $7.46_Z$ (d, J=2.0 Hz, 0.6H).

$^{13}$C NMR ($CDCl_3$, 125.8 MHz, Z-isomer): δ 18.4 ($CH_3$), 52.3 ($CH_3$), 55.6 ($CH_3$), 55.8 ($CH_3$), 76.6 (CH), 107.3 (CH), 110.9 (CH), 111.8 (CH), 121.1 (CH), 128.6 (C), 142.9 (CH), 147.4 (C), 148.5 (C), 172.0 (C).

Compound 37. (±)-methyl 2-methyl-2-((3-methyl-dodec-1-en-1-yl)oxy)propanoate

Following the procedure described for compound 32 (reaction mixture heated at 150° C.) and starting from the methyl enol ether prepared from 2-methylundecanal (8.0 g, 37.7 mmol), methyl 2-hydroxyisobutyrate (17.8 g. 151 mmol) and $KHSO_4$ (0.26 g, 1.88 mmol), the title compound (3.95 g, 35% yield) was isolated by short-path distillation (bp 118-122° C., 1 Pa) as a colorless liquid (E/Z=32:68).

$^{1}$H NMR ($CDCl_3$, 500 MHz): δ 0.88 (t, J=7.0 Hz, 3H), $0.94_Z$ and $0.96_E$ (both d, J=6.8 Hz, 3H), 1.15-1.34 (m, 16H), $1.47_Z$ and $1.48_E$ (both s, 6H), 1.95-$2.06_E$ (m, 0.3H), 2.60-$2.71_Z$ (m, 0.7H), $3.74_Z$ and $3.76_E$ (both s, 3H), $4.29_Z$ (dd, J=9.4, 6.3 Hz, 0.7H), $4.95_E$ (dd, J=12.1, 8.9 Hz, 0.3H), $5.93_Z$ (d, J=6.3 Hz, 0.7H), $6.01_E$ (d, J=12.1 Hz, 0.3H).

$^{13}$C NMR ($CDCl_3$, 125.8 MHz, Z-isomer): δ 14.1 ($CH_3$), 21.3 ($CH_3$), 22.7 ($CH_2$), 24.9 ($CH_3$), 25.2 ($CH_3$), 27.4 ($CH_2$), 28.7 (CH), 29.4 ($CH_2$), 29.7 ($CH_2$), 29.74 ($CH_2$), 29.8 ($CH_2$), 31.9 ($CH_2$), 37.6 ($CH_2$), 52.2 ($CH_3$), 78.5 (C), 116.8 (CH), 138.2 (CH), 174.4 (C).

Compound 38. (±)-methyl 2-methyl-2-(tridec-1-en-1-yloxy)propanoate

Following the procedure described for compound 8 (reaction mixture heated for 4.5 h) and starting from the dimethyl acetal of tridecanal (9.0 g, 36.8 mmol), methyl 2-hydroxy-isobutyrate (15.2 g, 129 mmol) and $KHSO_4$ (0.15 g, 1.1 mmol), the title compound (1.79 g, 16% yield) was isolated by short-path distillation (bp 122-126° C., 1.2 Pa) as a colorless liquid (E/Z=33:67).

$^{1}$H NMR ($CDCl_3$, 500 MHz): δ 0.88 (t, J=6.9 Hz, 3H), 1.20-1.39 (m, 18H), $1.477_E$ and $1.481_Z$ (both s, 6H), $1.89_E$ and $2.09_Z$ (both q, J=7.2 Hz, 2H), $3.75_Z$ and $3.76_E$ (both s, 3H), $4.50_Z$ (q, J=6.9 Hz, 0.7H), $5.08_E$ (dt, J=12.0, 7.5 Hz, 0.3H), $5.97_Z$ (d, J=6.3 Hz, 0.7H), $6.04_E$ (d, J=12.0 Hz, 0.3H).

$^{13}$C NMR ($CDCl_3$, 125 MHz, Z-isomer): (δ 14.1 ($CH_3$), 22.7 ($CH_2$), 23.8 ($CH_2$), 25.0 ($CH_3$), 29.3 ($CH_2$), 29.4 ($CH_2$), 29.5 ($CH_2$), 29.65 ($CH_2$), 29.68 ($CH_2$), 29.69 ($CH_2$), 29.7 ($CH_2$), 31.9 ($CH_2$), 52.2 ($CH_3$), 78.6 (C), 110.5 (CH), 139.2 (CH), 174.4 (C).

Compound 39. (±)-(Z)-hex-3-en-1-yl 2-(styryloxy)propanoate

General procedure: A mixture of a methyl lactate-derived enol ether (10-20 mmol), an alcohol (3-10 equiv) and DBU (1 equiv) was added to a round-bottomed flask equipped with a distillation head and nitrogen bubbler. Typically, the mixture was heated for 3 h at 150° C. (oil bath) and then for 1 h at 180° C. while allowing methanol to distill from the mixture. The transesterification products were isolated by silica gel flash chromatography (hexane/EtOAc) of the crude reaction mixtures.

Following this general procedure and using compound (±)-9 (4 g, 19.4 mmol) and cis-3-hexen-1-ol (19.4 g, 194 mmol), the title compound (3.0 g, 57% yield) was isolated by silica gel flash chromatography as a pale-yellow liquid (E/Z=53:47).

$^{1}$H NMR ($CDCl_3$, 500 MHz): δ 0.96 (t, J=7.5 Hz, 3H), $1.54_E$ and $1.59_Z$ (both d, J=6.9 Hz, 3H), 2.05 (pentet, J=7.5 Hz, 2H), 2.41 (pentet, J=7.0 Hz, 2H), 4.12-4.23 (m, 2H), 4.40 and 4.47 (both q, J=6.9 Hz, 1H), 5.26-5.34 (m, 1H), $5.30_Z$ (d, J=7.1 Hz, 0.5H), 5.46-5.53 (m, 1H), $5.93_E$ (d, J=12.9 Hz, 0.5H), $6.17_Z$ (d, J=7.1 Hz, 0.5H), $6.88_E$ (d, J=12.9 Hz, 0.5H), 7.11-7.31 (m, 4H), $7.63_Z$ (d, J=7.8 Hz, 1H).

$^{13}$C NMR ($CDCl_3$, 125.8 MHz, E-isomer): δ 14.2 ($CH_3$), 18.2 ($CH_3$), 20.6 ($CH_2$), 26.7 ($CH_2$), 64.8 ($CH_2$), 74.6 (CH), 108.5 (CH), 123.3 (CH), 125.3 (CH), 126.0 (CH), 128.6 (CH), 134.9 (CH), 135.8 (C), 146.0 (CH), 171.7 (C).

Compound 40. (±)-phenethyl 2-(styryloxy)propanoate

Following the general procedure described for compound 39 and using compound (±)-9 (4 g, 19.4 mmol) and 2-phenylethanol (7.11 g, 58.2 mmol), the title compound (0.75 g, 13% yield) was isolated by silica gel flash chromatography as a pale-yellow liquid (E/Z=53:47).

$^{1}$H NMR ($CDCl_3$, 500 MHz): δ 1.48 and 1.53 (both d, J=6.9 Hz, 3H), 2.95 and 2.97 (both d, J=7.0 Hz, 2H), 4.33-4.47 (m, 3H), $5.28_Z$ (d, J=7.1 Hz, 0.5H), $5.90_E$ (d, J=12.9 Hz, 0.5H), $6.11_Z$ (d, J=7.1 Hz, 0.5H), $6.83_E$ (d, J=12.9 Hz, 0.5H), 7.11-7.35 (m, 9H), $7.62_Z$ (d, J=8.2 Hz, 1H).

$^{13}$C NMR ($CDCl_3$, 125.8 MHz): δ 18.1 ($CH_3$), 18.2 ($CH_3$), 35.0 ($CH_2$), 65.5 ($CH_2$), 65.7 ($CH_2$), 74.5 (CH), 76.9 (CH), 107.2 (CH), 108.4 (CH), 125.3 (CH), 126.0 (CH), 126.03 (CH), 126.6 (CH), 126.7 (CH), 128.2 (CH), 128.5 (CH), 128.52 (CH), 128.54 (CH), 128.89 (CH), 128.93 (CH), 135.5 (C), 135.7 (C), 137.3 (C), 137.4 (C), 144.6 (CH), 146.0 (CH), 171.4 (C), 171.6 (C).

Compound 41. (±)-octan-3-yl 2-(styryloxy)propanoate

Following the general procedure described for compound 39 and using compound (±)-9 (2.2 g, 10.7 mmol) and 3-octanol (5.56 g, 42.7 mmol), the title compound (1.63 g, 50% yield) was isolated by silica gel flash chromatography as a pale-yellow liquid (mixture of diastereomers, E/Z=47:53).

$^{1}$H NMR ($CDCl_3$, 500 MHz): δ 0.79-0.93 (m, 6H), 1.16-1.35 (m, 6H), 1.48-1.65 (m, 4H), 1.55 and 1.59 (both d, J=6.9 Hz, 3H), 4.40 and 4.48 (both q, J=6.9 Hz, 1H), 4.87-4.96 (m, 1H), $5.30_Z$ (d, J=7.0 Hz, 0.5H), $5.904_E$ and $5.908_E$ (both d, J=12.9 Hz, 0.5H), $6.17_Z$ (d, J=7.0 Hz, 0.5H), $6.905_E$ and $6.909_E$ (d, J=12.9 Hz, 0.5H), 7.10-7.31 (m, 4H), 7.63 (d, J=8.0 Hz, 1H).

$^{13}$C NMR ($CDCl_3$, 125.8 MHz): δ 9.52 ($CH_3$), 9.54 ($CH_3$), 9.65 ($CH_3$), 13.95 ($CH_3$), 13.97 ($CH_3$), 13.99 ($CH_3$), 18.31 ($CH_3$), 18.35 ($CH_3$), 22.47 ($CH_2$), 22.49 ($CH_2$), 22.52 ($CH_2$), 22.53 ($CH_2$), 24.89 ($CH_2$), 24.92 ($CH_2$), 25.03 ($CH_2$), 26.87 ($CH_2$), 26.93 ($CH_2$), 26.94 ($CH_2$), 27.02 ($CH_2$), 31.62 ($CH_2$), 31.64 ($CH_2$), 31.66 ($CH_2$), 33.46 ($CH_2$), 33.50 ($CH_2$), 33.52 ($CH_2$), 33.60 ($CH_2$), 74.60 (CH), 76.82 (CH), 76.84 (CH), 76.86 (CH), 77.22 (CH), 77.24 (CH), 107.18 (CH), 107.22 (CH), 108.10 (CH), 108.13 (CH), 125.27 (CH), 125.29 (CH), 125.94 (CH), 125.97 (CH), 128.10 (CH), 128.52 (CH), 128.54 (CH), 135.53 (C), 135.54 (C), 135.80 (C), 135.82 (C), 144.52 (CH), 144.55 (CH), 146.15 (CH), 146.16 (CH), 171.39 (C), 171.42 (C), 171.66 (C), 171.69 (C).

Compound 42. (±)-(Z)-hex-3-en-1-yl 2-((4-methoxystyryl)oxy)propanoate

Following the general procedure described for compound 39 and using compound 35 (2.5 g, 10.6 mmol) and cis-3-hexen-1-ol (6.36 g, 63.5 mmol), the title compound (2.0 g, 62% yield) was isolated by silica gel flash chromatography as a pale-yellow liquid (E/Z=45:55).

$^{1}$H NMR ($CDCl_3$, 500 MHz): δ 0.96 (t, J=7.5 Hz, 3H), $1.53_E$ and $1.58_Z$ (both d, J=6.9 Hz, 3H), 2.05 (pentet, J=7.5 Hz, 2H), 2.41 (pentet, J=7.0 Hz, 2H), $3.78_E$ and $3.79_Z$ (both s, 3H), 4.12-4.23 (m, 2H), $4.38_Z$ and $4.44_E$ (both q, J=6.9 Hz, 1H), $5.26_Z$ (d, J=7.0 Hz, 0.6H), 5.27-5.33 (m, 1H), 5.46-5.53 (m, 1H), $5.91_E$ (d, J=12.8 Hz, 0.4H), $6.08_Z$ (d, J=7.0 Hz, 0.6H), $6.79_E$ (d, J=12.8 Hz, 0.4H), $6.80_E$ and $6.84_Z$ (both d, J=8.8 Hz, 2H), $7.13_E$ and $7.58_Z$ (both d, J=8.8 Hz, 2H).

$^{13}$C NMR ($CDCl_3$, 125.8 MHz, Z-isomer): δ 14.2 ($CH_3$), 18.3 ($CH_3$), 20.6 ($CH_2$), 26.7 ($CH_2$), 55.2 ($CH_3$), 64.7 ($CH_2$), 76.8 (CH), 106.9 (CH), 113.6 (CH), 123.4 (CH), 128.3 (C), 129.7 (CH), 134.8 (CH), 142.9 (CH), 157.8 (C), 171.7 (C).

Compound 43. (±)-phenethyl 2-((2-phenylprop-1-en-1-yl)oxy)propanoate

Following the general procedure described for compound 39 and using compound (±)-11 (5.0 g, 22.7 mmol) and 2-phenylethanol (8.32 g, 68.1 mmol), the title compound (1.8 g, 26% yield) was isolated by silica gel flash chromatography as a pale-yellow liquid (E/Z=85:15).

Following the general procedure described for compound 39 and starting with compound (±)-11 and 2-phenylethanol (X equiv), the title compound was isolated by silica gel flash chromatography in 31% yield as a colorless liquid (E/Z=85:15).

$^1$H NMR ($CDCl_3$, 500 MHz): δ $1.46_Z$ and $1.49_E$ (both d, J=6.9 Hz, 3H), $1.90_Z$ and $2.04_E$ (both s, 3H), $2.95_Z$ and $2.97_E$ (both t, J=6.9 Hz, 2H), $4.29_Z$ and $4.33_E$ (both q, J=6.9 Hz, 1H), 4.34-4.43 (m, 2H), $6.09_Z$ and $6.38_E$ (both s, 1H), 7.15-7.34 (m, 9.7H) and $7.68_Z$ (d, J=8.3 Hz, 0.3H).

$^{13}$C NMR ($CDCl_3$, 125.8 MHz, E-isomer): δ 12.9 ($CH_3$), 18.2 ($CH_3$), 35.0 ($CH_2$), 65.5 ($CH_2$), 76.1 (CH), 116.7 (C), 125.2 (CH), 126.2 (CH), 126.6 (CH), 128.3 (CH), 128.5 (CH), 128.9 (CH), 137.4 (C), 140.3 (C), 142.0 (CH), 171.9 (C).

Compound 44. (±)-octan-3-yl 2-((2-phenylprop-1-en-1-yl)oxy)propanoate

Following the general procedure described for compound 39 and using compound (±)-11 (5.0 g, 22.7 mmol) and 3-octanol (8.67 g, 68.1 mmol), the title compound (1.82 g, 25% yield) was isolated by silica gel flash chromatography as a pale-yellow liquid (mixture of diastereomers, E/Z=93:7).

$^1$H NMR ($CDCl_3$, 500 MHz, E-isomers): δ 0.81-0.92 (overlapping t, 6H), 1.18-1.35 (m, 6H), 1.49-1.64 (m, 4H), 1.55 (d, J=6.9 Hz, 3H), 2.05 (s, 3H), 4.36 (q, J=6.9 Hz, 1H), 4.87-4.94 (m, 1H), 6.43 (s, 1H), 7.15-7.20 (m, 1H), 7.24-7.34 (m, 4H).

$^{13}$C NMR ($CDCl_3$, 125.8 MHz, E-isomers): δ 9.51 ($CH_3$), 9.57 ($CH_3$), 12.91 ($CH_3$), 12.92 ($CH_3$), 13.97 ($CH_3$), 13.98 ($CH_3$), 18.34 ($CH_3$), 18.35 ($CH_3$), 22.49 ($CH_2$), 22.53 ($CH_2$), 24.94 ($CH_2$), 24.97 ($CH_2$), 26.94 ($CH_2$), 27.01 ($CH_2$), 31.65 ($CH_2$), 31.67 ($CH_2$), 33.54 ($CH_2$), 33.57 ($CH_2$), 76.38 (CH), 76.41 (CH), 76.6 (CH), 116.64 (C), 116.68 (C), 125.21 (CH), 125.22 (CH), 126.1 (CH), 128.3 (CH), 140.39 (C), 140.42 (C), 142.04 (CH), 142.06 (CH), 171.85 (C), 171.88 (C).

Compound 45. (±)-phenethyl 2-((2-(p-tolyl)prop-1-en-1-yl)oxy)propanoate

Following the general procedure described for compound 39 and using compound 22 (3.0 g, 12.8 mmol) and 2-phenylethanol (9.39 g, 76.8 mmol), the title compound (1.3 g, 31% yield) was isolated by silica gel flash chromatography as a pale-yellow liquid (E/Z=78:22).

$^1$H NMR ($CDCl_3$, 500 MHz): δ $1.45_Z$ and $1.48_E$ (both d, J=6.9 Hz, 3H), $1.88_Z$ and $2.02_E$ (both s, 3H), $2.32_E$ and $2.33_Z$ (both s, 3H), $2.95_Z$ and $2.96_E$ (both t, J=7.0 Hz, 2H), $4.27_Z$ and $4.32_E$ (both q, J=6.9 Hz, 1H), 4.33-4.43 (m, 2H), $6.05_Z$ and $6.35_E$ (both s, 1H), 7.07-7.30 (m, 8.6H) and $7.57_Z$ (d, J=8.2 Hz, 0.4H).

$^{13}$C NMR ($CDCl_3$, 125.8 MHz, E-isomer): δ 12.9 ($CH_3$), 18.2 ($CH_3$), 21.0 ($CH_3$), 35.0 ($CH_2$), 65.5 ($CH_2$), 76.0 (CH), 116.7 (C), 125.1 (CH), 126.6 (CH), 128.5 (CH), 128.9 (CH), 129.0 (CH), 135.8 (C), 137.37 (C), 137.43 (C), 141.4 (CH), 171.9 (C).

Compound 46. (±)-sec-butyl 2-((2-(p-tolyl)prop-1-en-1-yl)oxy)propanoate

Following the general procedure described for compound 39 and using compound 22 (2.0 g, 8.54 mmol) and 2-butanol (3.8 g, 51.2 mmol), the title compound (1.0 g, 42% yield) was isolated by silica gel flash chromatography as a colorless liquid (mixture of diastereomers, E/Z=81:19).

$^1$H NMR ($CDCl_3$, 500 MHz, E-isomers): δ 0.89 and 0.90 (both t, J=7.4 Hz, 3H), 1.22 and 1.24 (both d, J=6.3 Hz, 3H), 1.525 and 1.531 (both d, J=6.9 Hz, 3H), 1.55-1.68 (m, 2H), 2.03 (s, 3H), 2.31 (s, 3H), 4.32 (q, J=6.9 Hz, 1H), 4.92 (sextet, J=6.3 Hz, 1H), 6.39 (s, 1H), 7.09 (d, 8.2 Hz, 2H), 7.19 (d, J=8.2 Hz, 2H).

$^{13}$C NMR ($CDCl_3$, 125.8 MHz, E-isomers): δ 9.6 ($CH_3$), 13.0 ($CH_3$), 18.2 ($CH_3$), 18.3 ($CH_3$), 19.4 ($CH_3$), 19.8 ($CH_3$), 20.9 ($CH_3$), 28.7 ($CH_2$), 73.2 (CH), 73.3 (CH), 76.23 (CH), 76.25 (CH), 116.7 (C), 116.8 (C), 125.2 (CH), 129.0 (CH), 135.7 (C), 137.5 (C), 141.43 (CH), 141.46 (CH), 171.71 (C), 171.75 (C).

Compound 47. (±)-(Z)-hex-3-en-1-yl 2-((2-(4-methoxyphenyl)prop-1-en-1-yl)oxy)propanoate Following the general procedure described for compound 39 and using compound 20 (3.0 g, 12.1 mmol) and cis-3-hexen-1-ol (7.3 g, 72.9 mmol), the title compound (1.9 g, 49% yield) was isolated by silica gel flash chromatography as a pale-yellow liquid (E/Z=73:27).

$^1$H NMR ($CDCl_3$, 500 MHz): δ $0.956_E$ and $0.963_Z$ (both t, J=7.6 Hz, 3H), $1.51_Z$ and $1.53_E$ (both d, J=6.9 Hz, 3H), $1.89_Z$ and $2.02_E$ (both s, 3H), 2.05 (pentet, J=7.4 Hz, 2H), 2.40 (q, J=7.0 Hz, 2H), $3.79_E$ and $3.80_Z$ (both s, 3H), 4.11-4.21 (m, 2H), $4.31_Z$ and $4.34_E$ (both q, J=6.9 Hz, 1H), 5.27-5.34 (m, 1H), 5.46-5.54 (m, 1H), $6.08_Z$ and $6.33_E$ (both s, 1H), $6.83_E$ and $6.87_Z$ (both d, J=8.9 Hz, 2H), $7.22_E$ and $7.65_Z$ (both d, J=8.9 Hz, 2H).

$^{13}$C NMR ($CDCl_3$, 125.8 MHz, E-isomer): δ 13.1 ($CH_3$), 14.2 ($CH_3$), 18.3 ($CH_3$), 20.6 ($CH_2$), 26.7 ($CH_2$), 55.3 ($CH_3$), 64.6 ($CH_2$), 76.0 (CH), 113.7 (CH), 116.6 (C), 123.4 (CH), 126.3 (CH), 132.9 (C), 134.8 (CH), 140.9 (CH), 158.2 (C), 172.1 (C).

Compound 48. (±)-phenethyl 2-((2-(4-methoxyphenyl)prop-1-en-1-yl)oxy)propanoate

Following the general procedure described for compound 39 and using compound 20 (2.6 g, 10.4 mmol) and 2-phenylethanol (7.6 g, 62.3 mmol), the title compound (0.52 g, 15% yield) was isolated by silica gel flash chromatography as a pale-yellow liquid (E/Z=79:21).

$^1$H NMR ($CDCl_3$, 500 MHz): δ $1.46_Z$ and $1.48_E$ (both d, J=6.9 Hz, 3H), $1.88_Z$ and $2.0_E$ (both s, 3H), $2.95_Z$ and $2.96_E$ (both t, J=6.9 Hz, 2H), $3.78_E$ and $3.80_Z$ (both s, 3H), $4.27_Z$ and $4.31_E$ (both q, J=6.9 Hz, 1H), 4.33-4.44 (m, 2H), $6.03_Z$ and $6.30_E$ (both s, 1H), $6.83_E$ and $6.87_Z$ (both d, J=8.8 Hz, 2H), 7.17-7.31 (m, 6.6H) and $7.64_Z$ (d, J=8.8 Hz, 0.4H).

$^{13}$C NMR ($CDCl_3$, 125.8 MHz, E-isomer): δ 13.1 ($CH_3$), 18.2 ($CH_3$), 35.0 ($CH_2$), 55.3 ($CH_3$), 65.5 ($CH_2$), 76.0 (CH), 113.7 (CH), 116.5 (C), 126.3 (CH), 126.6 (CH), 128.5 (CH), 128.9 (CH), 132.8 (C), 137.4 (C), 140.9 (CH), 158.2 (C), 172.0 (C).

Compound 49. (±)-sec-butyl 2-((2-(4-methoxyphenyl)prop-1-en-1-yl)oxy)propanoate

Following the general procedure described for compound 39 and using compound 20 (2.0 g, 8.0 mmol) and 2-butanol (3.55 g, 47.9 mmol), the title compound (0.7 g, 30% yield) was isolated by silica gel flash chromatography as a colorless liquid (mixture of diastereomers, E/Z=87:13).

$^1$H NMR ($CDCl_3$, 500 MHz, E-isomers): δ 0.89 and 0.91 (both t, J=7.5 Hz, 3H), 1.22 and 1.24 (both d, J=6.3 Hz, 3H), 1.52 and 1.53 (both d, J=6.9 Hz, 3H), 1.54-1.67 (m, 2H), 2.02 (s, 3H), 3.79 (s, 3H), 4.32 (q, J=6.9 Hz, 1H), 4.92 (sextet, J=6.3 Hz, 1H), 6.34 (s, 1H), 6.83 (d, 8.8 Hz, 2H), 7.21 (d, J=8.8 Hz, 2H).

$^{13}$C NMR ($CDCl_3$, 125.8 MHz, E-isomers): (δ 9.61 ($CH_3$), 9.62 ($CH_3$). 13.2 ($CH_3$), 18.2 ($CH_3$), 18.3 ($CH_3$), 19.4 ($CH_3$), 19.5 ($CH_3$), 28.74 ($CH_2$), 28.75 ($CH_2$), 55.3 ($CH_3$), 73.2 (CH), 73.3 (CH), 76.19 (CH), 76.21 (CH), 113.8 (CH), 116.5 (C), 116.6 (C), 126.3 (CH), 133.0 (C), 140.88 (CH), 140.92 (CH), 158.2 (C), 171.7 (C), 171.8 (C).

Compound 50. (±)-phenethyl 2-((2-(naphthalen-2-yl)vinyl)oxy)propanoate

Following the general procedure described for compound 39, a mixture of compound 21 (5.5 g, 20.3 mmol), 2-phenylethanol (24.9, 203 mmol) and DBU (0.92 g, 6.0 mmol) were heated at 150° C. for 2 h. The reaction mixture was diluted with dichloromethane and washed with water. The organic phase was dried over $MgSO_4$, filtered and concentrated. The title compound (3.48 g, 47% yield) was isolated by silica gel flash chromatography as a viscous, pale-yellow oil (E/Z=81:19).

$^1$H NMR ($CDCl_3$, 500 MHz): δ $1.48_Z$ and $1.51_E$ (both d, J=6.9 Hz, 3H), $2.01_Z$ and $2.14_E$ (both s, 3H), $2.95_Z$ and $2.96_E$ (both t, J=7.0 Hz, 2H), $4.32_Z$ and $4.38_E$ (both q, J=6.9 Hz, 1H), 4.34-4.45 (m, 2H), $6.17_Z$ and $6.55_E$ (both s, 1H), 7.16-7.29 (m, 5H), 7.36-7.47 (m, 2.8H), 7.66-7.80 (m, 3.8H), 7.96-8.00 (m, 0.4H).

$^{13}$C NMR ($CDCl_3$, 125.8 MHz, E-isomer): δ 12.8 ($CH_3$), 18.3 ($CH_3$), 35.0 ($CH_2$), 65.6 ($CH_2$), 76.2 (CH), 116.5 (C), 123.3 (CH), 123.8 (CH), 125.2 (CH), 126.0 (CH), 126.6 (CH), 127.5 (CH), 127.7 (CH), 127.74 (CH), 128.5 (CH), 128.9 (CH), 132.1 (C), 133.7 (C), 137.4 (C), 137.5 (C), 142.6 (CH), 171.8 (C).

Compound 51. 1-(2-(((Z)-hex-3-en-1-yl)oxy)vinyl)-4-methoxybenzene (Example for Comparative Hydrolysis)

Following the procedure described for compound 32 and using the methyl enol ether prepared from para-anisaldehyde (8.0 g, 48.7 mmol), cis-3-hexen-1-ol (14.6 g, 146 mmol) and $KHSO_4$ (0.2 g, 1.46 mmol), the title compound (1.87 g, 17% yield) was isolated after two consecutive short-path distillations (bp 118-121° C., 1.1 Pa) as a colorless oil (E/Z=47:53).

$^1$H NMR ($CDCl_3$, 500 MHz): (δ 0.97 and 0.98 (both t, J=7.5 Hz, 3H), 2.05 (pentet, J=7.4 Hz, 2H), 2.44 and 2.47 (both q, J=6.9 Hz, 2H), 3.78 and 3.79 (both s, 3H), 3.80 and 3.88 (both t, J=6.9 Hz, 2H), $5.17_Z$ (d, J=7.0 Hz, 0.5H), 5.34-5.43 (m, 1H), 5.49-5.56 (m, 1H), $5.81_E$ (d, J=12.9 Hz, 0.5H), $6.12_Z$ (d, J=7.0 Hz, 0.5H), 6.79-6.84 (m, 2H), $6.87_E$ (d, J=12.9 Hz, 0.5H), 7.14 (d, J=8.8 Hz, 1H), 7.53 (d, J=8.8 Hz, 1H).

$^{13}$C NMR ($CDCl_3$, 125.8 MHz, Z-isomer): δ 14.3 ($CH_3$), 20.7 ($CH_2$), 28.1 ($CH_2$), 55.2 ($CH_3$), 72.9 ($CH_2$), 105.1 (CH), 113.6 (CH), 123.9 (CH), 128.9 (C), 129.4 (CH), 134.4 (CH), 145.0 (CH), 157.5 (C).

Example 2

Hydrolysis of Compounds According to Formula (I) and Comparative Compounds

The acid-catalyzed hydrolysis of Compounds 10, 25, 27, 28, 39, 40, 41, 42, 44, 46, 47 and 49 were measured and compared to the hydrolysis of enol ethers derived from the same aldehydes but using alkyl alcohols (Table below). Susceptibility to acid-catalyzed hydrolysis would result in loss of the enol ether and hence is an indicator of long-term storage stability in acidic consumer products. Each enol ether was dissolved in a 4:1 THF/1 M HCl mixture and the percent remaining over time measured relative to an internal standard.

Into a 15 mL vial were added 125 mg of enol ether, 60 mg of hexadecane and 10 mL of THF (purged with $N_2$ and containing 2500 ppm of BHT). After mixing, 2 mL of this solution were removed with a volumetric pipet and used to obtain the time zero measurement. 2 mL of 1 M HCl were mixed with the remaining 8 mL of the THF solution. This mixture was divided into 5 mL vials (1 mL per vial). The vials were gently topped with nitrogen and fitted with screw caps around which parafilm was wrapped. The vials were stored at room temperature until analyzed. For analyses, 2 mL of ethyl acetate was added to a vial and mixed. After phase separation, the top phase was collected and washed with saturated sodium carbonate (1 mL). Samples of the organic phase were analyzed by GC-FID. For the time zero sample, 0.5 mL of deionized water was added to the 2 mL taken from the original THF solution. 1 mL of this solution was added to a 5 mL vial and diluted with 2 mL of ethyl acetate and mixed. The top phase was collected and washed with saturated sodium carbonate (1 mL). The top phase then was analyzed by GC-FID. The percent of enol ether remaining was determined by dividing the peak area ratio of the enol ether to internal standard by the ratio measured at time zero.

TABLE 1

Hydrolysis of enol ethers in THF/1M HCl (80:20 v/v)

| | | percent remaining | | | | | | | |
|---|---|---|---|---|---|---|---|---|---|
| entry | compd | initial | 24 h | 48 h | 72 h | 168 h | 336 h | 504 h | 672 h |
| 1 | Compound 10 | 100 | 97.2 | 95.3 | 93.7 | 86.0 | 77 | 70.8 | 64.1 |
| 2 | Compound 39 | 100 | 96.3 | 95.3 | 90.7 | 79.6 | 67.3 | 53.0 | 41.2 |
| 3 | Compound 40 | 100 | 97.3 | 95.0 | 91.8 | 78.5 | 59.0 | 53.0 | 41.4 |
| 4 | Compound 41 | 100 | 99.7 | 99.2 | 98.1 | 94.1 | 91.7 | 88.4 | 84.4 |
| 5 | (2-(octan-3-yloxy)vinyl)benzene (Ex. 22, WO 2019/243501) | 100 | 84.9 | 72.0 | 61.7 | 33.6 | 10 | 4.5 | 0 |

TABLE 1-continued

| Hydrolysis of enol ethers in THF/1M HCl (80:20 v/v) | | | | | | | | | |
|---|---|---|---|---|---|---|---|---|---|
| | | percent remaining | | | | | | | |
| entry | compd | initial | 24 h | 48 h | 72 h | 168 h | 336 h | 504 h | 672 h |
| 6 | (2-phenethoxyvinyl)benzene (Ex. 20, WO 2019/243501) | 100 | 94.6 | 90.0 | 83.7 | 66.4 | 45.2 | 35.9 | 25.0 |
| 7 | Compound 42 | 100 | 95.1 | 93.9 | 89.8 | 78.1 | 60.1 | 46.8 | 35.2 |
| 8 | Compound 51. 1-(2-(((Z)-hex-3-en-1-yl)oxy)vinyl)-4-methoxybenzene (covered by WO 2019/243501) | 100 | 89.1 | 80.2 | 72.4 | 52.5 | 29.1 | 14.6 | 10.1 |
| 9 | Compound 25 | 100 | n.d.[a] | n.d. | 100 | 98.1 | 93.6 | 90.0 | 89.6 |
| 10 | Compound 44 | 100 | 99.3 | 99.5 | 98.9 | 96.5 | 93.3 | 90.4 | 88.6 |
| 11 | (1-phenethoxyprop-1-en-2-yl)benzene (Ex. 4, WO 2019/243501 A1) | 100 | 98.4 | 96.5 | 93.8 | 86.1 | 72.7 | 59.0 | 43.7 |
| 12 | (1-(octan-3-yloxy)prop-1-en-2-yl)benzene (Ex. 10, WO 2019/243501) | 100 | 96.2 | 92.4 | 89.3 | 76.6 | 57.3 | 44.5 | 33.6 |
| 13 | (1-(2,6-dimethylheptan-2-yloxy)prop-1-en-2-yl)benzene (Ex. 18, WO 2019/243501 A1) | 100 | 92.9 | 85.7 | 80.5 | 60.3 | 41.7 | 28.1 | 17.9 |
| 14 | Compound 28 | 100 | 99.3 | 98.5 | 98.5 | 96.2 | 92.1 | 89.7 | 85.8 |
| 15 | Compound 46 | 100 | 98.0 | 97.0 | 95.8 | 90.9 | 82.4 | 74.5 | 66.6 |
| 16 | 1-methyl-4-(1-phenethoxyprop-1-en-2-yl)benzene (Ex. 26, WO 2019/243501 A1) | 100 | 97.8 | 95.5 | 93.9 | 85.0 | 70.4 | 57.3 | 42.5 |
| 17 | Compound 47 | 100 | 96.6 | 94.4 | 91.2 | 81.6 | 65.0 | 51.1 | 40.0 |
| 18 | Compound 49 | 100 | 96.8 | 94.8 | 93.8 | 87.6 | 76.9 | 67.6 | 56.2 |
| 19 | Compound 27 | 100 | 102 | 101 | 99.7 | 97.8 | 87.7 | 89.1 | 84.7 |
| 20 | 1-methoxy-4-(1-phenethoxyprop-1-en-2-yl)benzene (Ex. 27, WO 2019/243501 A1) | 100 | 98.0 | 95.4 | 92.2 | 78.9 | 56.0 | 36.8 | 23.6 |

[a]n.d. stands for not determined

The Table above compares the rate of hydrolysis for enol ethers prepared from phenylacetaldehyde, 2-(4-methoxyphenyl)acetaldehyde, 2-phenylpropanal, 2-(para-tolyl)propanal and 2-(4-methoxyphenyl)propanal derived from either alkyl alcohols or alpha-hydroxyesters. For the phenylacetaldehyde enol ether prepared from 2-phenylethanol (entry 5) and 3-octanol (entry 6) only 39.5% and 4.5% remained after 504 h (21 days) compared to 70.8%, 53.0%, 53.0% and 88.4% (entries 1-4) for enol ethers prepared from an alpha-hydroxyester. At the same time point, 46.8% of the alpha-hydroxyester-derived enol ethers of para-methoxyphenylacetaldehyde (entries 7) remained while only 14.6% remained of the cis-3-hexen-1-ol derived enol ether (entry 8). For the enol ethers prepared from 2-phenylpropanal, improved hydrolytic stability was observed for compounds 25 and 44 (entries 9 and 10) compared to enol ethers prepared from a primary (entry 11), secondary (entry 12) or tertiary alkyl alcohol (entry 13). Slower rates of hydrolysis also were measured for the alpha-hydroxyester derived enol ethers of 2-(para-tolyl)propanal (entries 14 and 15) and 2-(4-methoxyphenyl)propanal (entries 17-19) compared to the corresponding enol ethers derived from 2-phenylethanol (entries 16 and 20). The table shows that the enol ethers prepared from an alpha-hydroxyester hydrolyze slower than the corresponding enol ethers prepared from an alkyl alcohol. Hence, the enol ethers of the invention are predicted to be more stable in acidic consumer products such as a liquid fabric softener.

Example 3

Headspace Analysis from Fabric Softener Application Comprising Invention's Compounds of Formula (I)

A model liquid fabric softener was prepared by mixing a TEA-esterquat (Stepantex® VL 90A), 12.3 wt %, 10% aqueous calcium chloride, 0.4 wt %, Proxcel GXL, 0.04 wt % and deionized water, 87.2 wt %. The enol ethers (0.075 mmol) were weighed into a vial and dissolved in 0.25 mL of acetone. Liquid fabric softener (4.5 g) was added to the vial and the mixture shaken by hand to mix. Reference samples were prepared in the same manner using 0.075 mmol of each released volatile. The fabric softener samples were rinsed with deionized water into a 3 L beaker and the beaker was filled to a total volume of 1.5 L. Three, 5-g cotton swatches (ca. 12.5×12.5 cm, weight 270 g/m2, item 403 from Testfabrics, West Pittston, Pa.) were added to the beaker and agitated by hand for 3 min After an additional 2 min of standing, the swatches were retrieved, and excess water squeezed out by hand. The cloths were hung to dry overnight (15-16 h) at rt. The swatches then were subjected to dynamic headspace analysis.

Each swatch was placed inside a thermostatted (25° C.), headspace sampling cell (about 160 mL volume). Using an air-sampling pump, a constant flow of air (200 mL/min) was drawn through the sampling cell and then through a cartridge containing 100 mg of Tenax®. Prior to entering the sample cell, the air was drawn through a plug of active charcoal and then through a saturated aqueous NaCl solution to maintain a constant relative humidity of 75%. Headspace samples were collected continuously over a 2.5-hour period in 30 min. increments. The cartridges were thermally desorbed with a Gerstel TDU 3.5 with cryofocusing at −30° C. and desorbed into an Agilent 8890 gas chromatograph equipped with an HP1 capillary column (30 m, i.d. 0.25 mm, film 0.25 μm) and coupled with Agilent 5977B mass spectrometer. TDU temperature settings for desorption: 40° C. to 70° C. (30° C./min) hold for 4 min then heat to 260° C. (400° C./min) and hold 5 min. CIS settings (Tenax® packed liner): cryofocus at −30° C. then heat at 12° C./sec to 300° C. and hold for 4 min (heater mode: standard). PTV inlet settings: pressure 7.7 psi, total flow 99 ml/min, septum purge flow 3 ml/min on standard flow mode. The inlet mode was set to solvent vent with a purge flow to split vent set at 95 ml/min and the vent flow at 50 ml/min. The GC oven temperature profile was 52° C. to 110° C. at 20° C./min (hold 2 min) then ramped to 210° C. (20 C/min). The amount of each fragrance volatile collected (reported as ng/L of air) was determined using external standard calibrations of the respective chemicals. At least five acetone solutions were prepared with concentrations of the analytes ranging from 0.05 g/L to 5 g/L. The solutions were injected (0.2 μL) onto Tenax® cartridges and desorbed as described above. Each solution was analyzed in triplicate. Calibration curves were forced through the origin.

TABLE 2

Dynamic headspace concentrations (ng/L ± std. dev.) of perfumery raw materials obtained from line-dried cotton treated with fabric softener containing enol ether profragrances compared to their respective references (averaged data for two swatches).

| | | 60-90 min sample | | 120-150 min sample | |
|---|---|---|---|---|---|
| | perfumery raw material | profragrance | reference | profragrance | reference |
| Cmpd 2 | 2-undecananone | 88.0 ± 5.3 | 3.2 ± 1.9 | 82.7 ± 12.1 | 4.6 ± 3.5 |
| Cmpd 4 | 4-phenyl-2-butanone | 258 ± 96 | 2.5 ± 0.3 | 342 ± 75 | 4.2 ± 0.6 |
| Cmpd 6 | 2-undecanone | 318 ± 31 | 2.3 ± 0.3 | 293 ± 13 | 2.6 ± 0.2 |
| | (Z)-hex-3-en-1-yl 2-(formyloxy)propanoate | 585±113 | 9.8 ± 1.9 | 451 ± 77.4 | 11.9 ± 0 |
| | (Z)-hex-3-en-1-yl 2-hydroxypropanoate | 427 ± 23.2 | 2.5 ± 0.1 | 434 ± 23.7 | 2.6 ± 0.1 |
| Cmpd 18 | 2-pentylcyclopentanone | 193 ± 61 | 0.7 ± 0.2 | 141 ± 5.1 | 1.0 ± 0.3 |
| Cmpd 20 | acetanisole | 79.9 ± 5.7 | 2.8 ± 3.9 | 137.5 ± 9.4 | 8.5 ± 4.8 |
| Cmpd 26 | 4-phenyl-2-butanone | 208 ± 38.4 | 2.5 ± 0.3 | 241 ± 81 | 4.2 ± 0.6 |
| Cmpd 29 | 2-pentylcyclopentanone | 126 ± 26 | 0.7 ± 0.2 | 142 ± 11 | 1.0 ± 0.3 |
| Cmpd 31 | dodecanal | 278 ± 41.6 | 128 ± 26.6 | 296 ± 44.8 | 198 ± 92.1 |
| Cmpd 32 | 10-undecenal | 349 ± 58 | 23.4 ± 9.0 | 488 ± 3.9 | 24.5 ± nd |
| Cmpd 33 | 2-methylundecanal | 277 ± 72 | 21.7 ± 4.6 | 267 ± 40 | 20.5 ± 24.6 |
| Cmpd 34 | 3-phenylbutanal | 238 ± 12 | 27.5 ± 6.7 | 329 ± 2.2 | 31.2 ± 8.7 |
| Cmpd 38 | dodecanal | 277 ± 22.5 | 128 ± 26.6 | 253 ± 13.7 | 198 ± 92.1 |

Example 4

Headspace Analysis from Leave-on Hair Conditioner Application Comprising Invention's Compounds of Formula (I)

A model rinse-off hair conditioner was prepared in a generally known manner with the following composition (weight %):

| | |
|---|---|
| Deionized water | 95.50% |
| Salcare SC 91 (origin: BASF) | 1.00% |
| Aculyn ™ 46 (origin: Dow) | 1.00% |
| Wacker-Belsil ® DMS 6038 (origin: Wacker) | 0.50% |
| Phenonip ™ (origin: Clariant) | 0.50% |
| Mirasil ® ADM-E (origin: Elkem) | 1.50% |

A 25 wt % enol ether solution in acetone was dispersed in a leave-on hair conditioner to provide samples containing 0.16 mmol of the precursor. The sample was mixed well and allowed to macerate for 2 h. Reference samples containing an equimolar level of the expected ketone were prepared in the same way. The hair swatches (10 g) were rinsed under warm tap water (37° C.) for 30 s then gently combed to straighten the hair. The hair conditioner samples (1 g) were each applied to a swatch and massaged into the hair to disperse thoroughly. The swatches were hung and allowed to dry overnight (15-16 h) at rt. The hair swatches then were subjected to dynamic headspace analysis as described in Example 3 except that the headspace sampling cells were thermostatted at 35° C.

TABLE 3

Dynamic headspace concentrations (ng/L ± std. dev.) of perfumery raw materials obtained from air-dried hair swatches treated with leave-on hair conditioner containing enol ether profragrances compared to their respective references (averaged data for two swatches).

| | | 60-90 min sample | | 120-150 min sample | |
|---|---|---|---|---|---|
| | perfumery raw material | profragrance | reference | profragrance | reference |
| Cmpd 18 | 2-pentylcyclopentanone | 121 ± 12 | 34 ± 18 | 108 ± 11 | 48.4 ± 23 |

Example 5

Headspace Analysis from Rinse-Off Hair Conditioner Application Comprising Invention's Compounds of Formula (I)

A model rinse-off hair conditioner was prepared in a generally known manner with following composition (weight %)

| | |
|---|---|
| Deionized water | 92.54% |
| Chlorhexidine dihydrochloride | 0.05% |
| Natrosol ® 250 H (origin: Hercules) | 1.00% |
| Dehyquart ® C 4046 (origin: Cognis) | 0.20% |
| Mirasil ® ADM-E (origin: Rhodia) | 1.20% |
| Genamin ® KDM (origin: Clariant) | 1.00% |
| Crodamol ® SS (origin: Croda) | 0.50% |
| Crodacol ® C90 (origin: Croda) | 3.01% |
| Myristyl alcohol (origin: Aldrich) | 0.20% |
| Nipagin ® M (origin: Nipa) | 0.30% |

A 25 wt % enol ether solution in acetone was dispersed in a rinse-off hair conditioner to provide samples containing 0.16 mmol of the precursor. Reference samples containing an equimolar level of the expected aldehyde were prepared in the same way. The samples were left macerating at room temperature for 2 h. Hair swatches (10 g) were wetted with warm tap water (about 37° C.) and the excess water gently squeezed out. The rinse-off conditioner (1.0 g) was applied along the hair swatch and gently massaged into the hair for 1 min. The swatch was then dipped in a 3-L beaker of warm tap water (about 37° C.) and moved up and down three times and then side-to-side three times. After squeezing out the excess water, the process was repeated with application of another 1 g sample of the hair conditioner. After gently squeezing out excess water, the swatches were hung and allowed to dry at room temperature overnight (15-16 h). The hair swatches then were subjected to dynamic headspace analysis as described in Example 3 except that the headspace sampling cells were thermostatted at 35° C.

TABLE 4

Dynamic headspace concentrations (ng/L ± std. dev.) of perfumery raw materials obtained from air-dried hair swatches treated with rinse-off hair conditioner containing enol ether profragrances compared to their respective references (averaged data for two swatches).

| | | 60-90 min sample | | 120-150 min sample | |
|---|---|---|---|---|---|
| | perfumery raw material | profragrance | reference | profragrance | reference |
| Cmpd 32 | 10-undecenal | 118 ± 59 | 41.9 ± 10.6 | 102 ± 52 | 60.0 ± 23.3 |

Example 6

Preparation of a Perfume Oil

A non-limiting example of a typical perfume oil is prepared by admixing the following perfuming co-ingredients:

| Ingredients | Weight % |
|---|---|
| Ethyl 2-methylbutanoate | 0.16 |
| Hexyl acetate | 0.37 |
| Limonene | 1.67 |
| 2,6-Dimethyl-7-octen-2-ol | 0.94 |
| 2-Phenylethanol | 2.15 |
| Linalool | 0.73 |
| (2RS,4SR/4RS)-4-Methyl-2-(2-methyl-1-propen-1-yl)tetrahydro-2H-pyran | 0.30 |
| Ethyl 2-methyl-1,3-dioxolane-2-acetate | 0.32 |
| Benzyl acetate | 2.46 |
| Allyl heptanoate | 0.38 |
| alpha-Terpineol | 0.88 |
| 3,7-Dimethyl-6-octen-1-ol | 0.55 |
| 4-Methoxybenzaldehyde | 1.00 |
| (E)-4-Methyl-3-decen-5-ol | 0.37 |
| [cis/trans-4-(2-Propanyl)cyclohexyl]methanol | 0.47 |
| 1-Methoxy-4-[(1E)-1-propen-1-yl]benzene | 0.15 |
| (1RS,2RS/2SR)-2-(2-Methyl-2-propanyl)cyclohexyl acetate | 1.95 |
| 1,1-Dimethyl-2-phenylethyl acetate | 0.95 |
| Tricyclo[5.2.1.0$^{2,6}$]dec-3/4-en-8-yl acetate | 3.34 |
| Allyl 3-cyclohexylpropanoate | 0.26 |
| 3-(4-Isopropylphenyl)-2-methylpropanal | 8.18 |
| (3E)-3-Methyl-4-(2,6,6-trimethyl-2-cyclohexen-1-yl)-3-buten-2-one and (1E)-1-(2,6,6-trimethyl-2-cyclohexen-1-yl)-1-penten-3-one | 1.13 |
| 2-Phenoxyethyl 2-methylpropanoate | 5.38 |
| Tricyclo[5.2.1.0(2,6)]dec-3/4-en-8-yl propanoate | 2.32 |
| 5-Heptyldihydro-2(3H)-furanone | 2.30 |
| 2/3-Methylbutyl salicylate | 1.42 |
| (3Z)-3-Hexen-1-yl salicylate | 0.31 |
| 1-(2,3,8,8-Tetramethyl-1,3,4,5,6,7-hexahydronaphthalen-2-yl)ethanone | 16.03 |
| Hexyl 2-hydroxybenzoate | 5.04 |
| (2E)-2-Benzylideneoctanal | 21.22 |
| (—)-(3aR,5aS,9aS,9bR)-3a,6,6,9a-Tetramethyldodecahydronaphtho[2,1-b]furan | 0.27 |

-continued

| Ingredients | Weight % |
|---|---|
| 1-Oxa-12/13-cyclohexadecen-2-one | 4.78 |
| Oxacyclohexadecan-2-one | 3.82 |
| Benzyl 2-hydroxybenzoate | 3.01 |
| Dipropylene glycol | 5.39 |
| | Total: 100 |

Example 7

Preparation of Transparent Isotropic Shampoo Formulations Comprising an Invention's Compound of Formula (I)

A typical unperfumed transparent isotropic shampoo formulation is listed in Table 5. The unperfumed shampoo formulation is prepared by dispersing Polyquaternium-10 in water. The remaining ingredients of Phase A are mixed separately by addition of one after the other while mixing well after each adjunction. This pre-mix is added to the Polyquaternium-10 dispersion and mixed for another 5 min. Then, the premixed Phase B and the premixed Phase C are added (Monomuls® 90L-12 is heated to melt in Texapon® NSO IS) while agitating. Phase D and Phase E are added while agitating. The pH is adjusted with a citric acid solution to 5.5-6.0.

TABLE 5

Composition of a typical unperfumed transparent isotropic shampoo formulation.

| Phase | Ingredients | Amount [wt %] |
|---|---|---|
| A | Deionized water | 44.4 |
| | Polyquaternium-10 (1) | 0.3 |
| | Glycerin 85% (2) | 1.0 |
| | DMDM Hydantoin (3) | 0.2 |
| B | Sodium laureth sulfate (4) | 28.0 |
| | Cocamidopropyl betaine (5) | 3.2 |
| | Disodium cocoamphodiacetate (6) | 4.0 |
| | Ethoxy (20) stearyl alcohol (7) | 1.0 |
| C | Sodium laureth sulfate (4) | 3.0 |
| | Glyceryl laureate (8) | 0.2 |
| D | Deionized water | 1.0 |
| | Sodium methylparaben (9) | 0.1 |
| E | Sodium chloride (10% aqueous solution) | 15.0 |
| | Citric acid (10% aqueous solution to pH 5.5-6.0) | q.s. |

(1) Ucare ® Polymer JR-400; origin: Noveon
(2) Origin: Brenntag Schweizerhall AG
(3) Glydant ®; origin: Lonza
(4) Texapon ® NSO IS; origin: Cognis
(5) Tego ® Betain F 50; origin: Evonik
(6) Amphotensid GB 2009; origin: Zschimmer & Schwarz
(7) Brij ® S20; origin: Croda
(8) Monomuls ® 90 L-12; origin: Gruenau GmbH
(9) Nipagin Monosodium; origin: NIPA The perfumed shampoo formulation is then obtained by adding, under gentle shaking, a perfume oil (as e.g. described in Example 6, 0.1 to 0.8% by weight relative to the total weight of the unperfumed shampoo formulation) and at least one of the compounds of formula (I) such as, for example, compound 37, 33 or 18 (0.05 to 0.50% by weight relative to the total weight of the unperfumed shampoo formulation) into the unperfumed shampoo formulation listed in Table 5.

Example 8

Preparation of Pearly Shampoo Formulations Comprising an Invention's Compound of Formula (I)

A typical unperfumed pearly shampoo formulation is listed in Table 6. The unperfumed shampoo formulation is prepared by dispersing Tetrasodium EDTA, Guar hydroxypropyltrimonium chloride and Polyquaternium-10 in water. NaOH (10% aqueous solution, Phase B) is added once Phase A is homogeneous. Then, the premixed Phase C is added, and the mixture heated to 75° C. Phase D ingredients are added and mixed until the mixture is homogeneous. The mixture is cooled. At 45° C., Phase E ingredients are added while mixing. The final viscosity is adjusted with NaCl (25% aqueous solution) and a pH of 5.5-6.0 is adjusted with NaOH (10% aqueous solution).

TABLE 6

Composition of a typical pearly shampoo formulation.

| Phase | Ingredients | Amount [wt %] |
|---|---|---|
| A | Deionized water | 45.97 |
| | Tetrasodium EDTA (1) | 0.05 |
| | Guar hydroxypropyl-trimonium chloride (2) | 0.05 |
| | Polyquaternium-10 (3) | 0.075 |
| B | NaOH (10% aqueous solution) | 0.30 |
| C | Ammonium lauryl sulfate (4) | 34.00 |
| | Ammonium laureth sulfate (5) | 9.25 |
| | Cocamidopropyl betaine (6) | 2.00 |
| | Dimethicone (&) $C_{12-13}$ pareth-4 (&) $C_{12-13}$ pareth-23 (&) salicylic acid (7) | 2.50 |
| D | Cetyl alcohol (8) | 1.20 |
| | Cocamide MEA (9) | 1.50 |
| | Glycol distearate (10) | 2.00 |
| E | Methylchloroisothiazolinone & methylisothiazolinone (11) | 0.10 |
| | D-Panthenol 75% (12) | 0.10 |
| | Deionized water | 0.30 |
| F | Sodium chloride (25% aqueous solution) | 0.60 |

(1) EDETA ® B Powder; origin: BASF
(2) Jaguar ® C14 S; origin: Rhodia
(3) Ucare ® Polymer JR-400; origin: Noveon
(4) Sulfetal ® LA B-E; origin: Zschimmer & Schwarz
(5) Zetesol ® LA; origin: Zschimmer & Schwarz
(6) Tego ® Betain F 50; origin: Evonik
(7) Xiameter ® MEM-1691; origin: Dow Corning
(8) Lanette ® 16; origin: BASF
(9) Comperlan ® 100; origin: Cognis
(10) Cutina ® AGS; origin: Cognis
(11) Kathon ® CG; origin: Rohm & Haas
(12) D-Panthenol; origin: Roche A perfumed pearly shampoo formulation is then obtained by adding, under gentle shaking, a perfume oil (as e.g. described in Example 6, 0.1 to 0.8% by weight relative to the total weight of the unperfumed shampoo formulation) and at least one of the compounds of formula (I) such as, for example, compound 37, 33 or 18 (0.05 to 0.50% by weight relative to the total weight of the unperfumed shampoo formulation) into the unperfumed pearly shampoo formulation listed in Table 6.

Example 9

Preparation of Rinse-Off Hair Conditioner Formulations Comprising an Invention's Compound of Formula (I)

A typical unperfumed rinse-off hair conditioner formulation is listed in Table 7. The unperfumed rinse-off hair conditioner formulation is prepared by mixing the ingredients of Phase A until an uniform mixture was obtained. Tylose® is allowed to completely dissolve. Then the mixture is heated to 70-75° C. The ingredients of Phase B are combined and melted at 70-75° C. Then the ingredients of Phase B are added to Phase A with good agitation, and the mixing is continued until that the mixture has a temperature of 60° C. Then, the ingredients of Phase C are added while agitating and keeping mixing until the mixture cooled to 40° C. The pH is adjusted with a citric acid solution to 3.5-4.0.

TABLE 7

Composition of a typical rinse-off hair conditioner formulation.

| Phase | Ingredients | Amount [wt %] |
|---|---|---|
| A | Deionized water | 81.8 |
| | Behentrimonium chloride (1) | 2.5 |
| | Hydroxyethylcellulose (2) | 1.5 |
| B | Cetearyl alcohol (3) | 4.0 |
| | Glyceryl stearate (and) PEG-100 stearate (4) | 2.0 |
| | Behentrimonium metho-sulfate (and) cetyl alcohol (and) butylene glycol (5) | 4.0 |
| | Ethoxy (20) stearyl alcohol (6) | 1.0 |
| C | Amodimethicone (and) Trideceth-12 (and) Cetrimonium chloride (7) | 3.0 |
| | Chlorhexidine digluconate (20% aqueous solution) (8) | 0.2 |
| D | Citric acid (10% aqueous solution tol pH 3.5-4.0) | q.s. |

(1) Genamin ® KDMP; origin: Clariant
(2) Tylose ® H10 Y G4; origin: Shin Etsu
(3) Lanette ® O; origin: BASF
(4) Arlacel ® 165; origin: Croda
(5) Incroquat ® Behenyl TMS-50-PA- (MH); origin: Croda
(6) Brij ® S20; origin: Croda
(7) Xiameter ® MEM-949; origin: Dow Corning
(8) Origin: Alfa Aesar A perfumed rinse-off hair conditioner formulation is then obtained by adding, under gentle shaking, a perfume oil (as e.g. described in Example 6, 0.2 to 1.0% by weight relative to the total weight of the unperfumed conditioner formulation) and at least one of the compounds of formula (I) such as, for example, compound 37, 33 or 18 (0.05 to 0.5% by weight relative to the total weight of the unperfumed conditioner formulation) into the unperfumed rinse-off hair conditioner formulation listed in Table 7.

Example 10

Preparation of Structured Shower Gel Formulations Comprising an Invention's Compound of Formula (I)

A typical unperfumed structured shower gel formulation is listed in Table 8. A perfumed structured shower gel is prepared by adding, under gentle shaking, a perfume oil (as e.g. described in Example 6, 0.1 to 1.5% by weight relative to the total weight of the structured shower gel) and at least one of the invention's compounds of formula (I) such as, for example, compound 37, 33 or 18 (0.05 to 0.50% by weight relative to the total weight of the structured shower gel) into the unperfumed structured shower gel formulation of Table 8.

TABLE 8

Composition of a typical unperfumed structured shower gel formulation.

| Ingredients | Amount [wt %] |
|---|---|
| Deionized water | 49.35 |
| Tetrasodium EDTA (1) | 0.05 |
| Acrylates co-polymer (2) | 6.00 |
| Sodium $C_{12-15}$ pareth sulfate (3) | 35.00 |
| Sodium hydroxide (20% aqueous solution) | 1.00 |
| Cocamidopropyl betaine (4) | 8.00 |
| Methylchloroisothiazolinone and methylisothiazolinone (5) | 0.10 |
| Citric acid (40% aqueous solution) | 0.50 |

(1) EDETA B powder; origin: BASF
(2) Carbopol Aqua SF-1 polymer; origin: Noveon
(3) Zetesol AO 328 U; origin: Zschimmer & Schwarz
(4) Tego Betain F 50; origin: Goldschmidt
(5) Kathon ® CG; origin: Rohm & Haas

Example 11

Preparation of Transparent Shower Gel Formulations Comprising an Invention's Compound of Formula (I)

A typical unperfumed transparent shower gel formulation is listed in Table 9. A perfumed transparent shower gel is prepared by adding, under gentle shaking, a perfume oil (as e.g. described in Example 6, 0.5 to 1.5% by weight relative to the total weight of the transparent shower gel) and at least one of the invention's compounds of formula (I) such as, for example, compound 37, 33 or 18 (0.05 to 0.50% by weight relative to the total weight of the transparent shower gel) into the unperfumed transparent shower gel formulation of Table 9.

TABLE 9

Composition of a typical unperfumed transparent shower gel formulation

| Ingredients | Amount [wt %] |
|---|---|
| Deionized water | 52.40 |
| Tetrasodium EDTA (1) | 0.10 |
| Sodium benzoate | 0.50 |
| Propylene glycol | 2.00 |
| Sodium $C_{12-15}$ pareth sulfate (2) | 35.00 |
| Cocamidopropyl betaine (3) | 8.00 |
| Polyquaternium-7 (4) | 0.20 |
| Citric acid (40% aqueous solution) | 1.00 |
| Sodium chloride | 0.80 |

(1) EDETA B powder; origin: BASF
(2) Zetesol AO 328 U; origin: Zschiminer & Schwarz
(3) Tego Betain F 50; origin: Goldschmidt
(4) Merquat ® 550; origin: Lubrizol

Example 12

Preparation of Milky Shower Gel Formulations Comprising an Invention's Compound of Formula (I)

A typical unperfumed milky shower gel formulation is listed in Table 10. A perfumed milky shower gel is prepared by adding, under gentle shaking, a perfume oil (as e.g. described in Example 6, 0.1 to 1.5% by weight relative to the total weight of the milky shower gel) and at least one of the invention's compounds of formula (I) such as, for example, compound 37, 33 or 18 (0.05 to 0.50% by weight relative to the total weight of the milky shower gel) into the unperfumed milky shower gel formulation of Table 10.

TABLE 10

Composition of a typical unperfumed milky shower gel formulation.

| Ingredients | Amount [wt %] |
|---|---|
| Deionized water | 50.95 |
| Tetrasodium EDTA (1) | 0.05 |
| Sodium benzoate | 0.50 |
| Glycerin (86% aqueous solution) | 3.50 |
| Sodium laureth sulfate (2) | 27.00 |
| Polyquatemium-7 (3) | 1.00 |
| Coco-betaine(4) | 6.00 |
| PEG-120 Methyl glucose trioleate (5) | 1.00 |
| Citric acid (40% aqueous solution) | 1.00 |
| Glycol distearate & laureth-4 & cocamidopropyl betaine (6) | 3.00 |
| Sodium chloride (20% aqueous solution) | 5.00 |
| PEG-40 hydrogenated castor oil (7) | 1.00 |

(1) EDETA ® B powder; origin: BASF
(2) Texapon ® NSO IS; origin: Cognis
(3) Merquat ® 550; origin: Lubrizol
(4) Dehyton ® AB-30; origin: Cognis
(5) Glucamate ® LT; origin: Lubrizol
(6) Euperlan ® PK 3000 AM; origin: Cognis
(7) Cremophor ® RH 40; origin: BASF

Example 13

Preparation of Anhydrous Antiperspirant Spray Formulations Comprising an Invention's Compound of Formula (I)

A typical unperfumed anhydrous antiperspirant spray formulation is listed in Table 11. The anhydrous antiperspirant spray formulation is prepared by using a high speed stirrer. Silica and Quaternium-18-hectorite are added to the mixture of isopropyl myristate and cyclomethicone. Once completely swollen, aluminium chlorohydrate is added portion-wise under stirring until the mixture becomes homogeneous and without lumps.

TABLE 11

Composition of a typical unperfumed anhydrous antiperspirant spray.

| Ingredients | Amount [wt %] |
|---|---|
| Cyclomethicone (1) | 53.51 |
| Isopropyl myristate | 9.04 |
| Silica (2) | 1.03 |
| Quaternium-18-hectorite (3) | 3.36 |
| Aluminium chlorohydrate (4) | 33.06 |

(1) Dow Corning ® 345 Fluid; origin: Dow Corning
(2) Aerosil ® 200; origin: Evonik
(3) Bentone ® 38; origin: Elementis Specialities
(4) Micro Dry Ultrafine; origin: Reheis The perfumed formulation is then obtained by adding a perfume oil (as e.g. described in Example 6, 0.85% by weight relative to the total weight of the antiperspirant spray formulation) and at least one of the invention's compounds of formula (I) such as, for example, compound 37, 33 or 18 (0.15% by weight relative to the total weight of the antiperspirant spray formulation) into the unperfumed antiperspirant spray formulation of Table 11.

Example 14

Preparation of Deodorant Spray Emulsion Formulations Comprising an Invention's Compound of Formula (I)

A typical deodorant spray emulsion formulation is prepared by mixing and dissolving all the ingredients according to the sequence of Table 12. Then a perfume oil (as e.g. described in Example 6, 1.35% by weight relative to the total weight of the deodorant spray formulation) and at least one of the invention's compounds of formula (I) such as, for example, compound 37, 33 or 18 (0.10 to 0.20% by weight relative to the total weight of the deodorant spray formulation) are added under gentle shaking. Then aerosol cans are filled, and the propellant is crimped and added. Aerosol filling: 40% active solution 60% propane/butane (2.5 bar).

TABLE 12

Composition of a typical unperfumed deodorant spray formulation.

| Ingredients | Amount [wt %] |
|---|---|
| Ethanol (95%) | 90.65 |
| Triclosan (1) | 0.26 |
| Isopropyl myristate | 9.09 |

(1) Irgasan ® DP 300; origin: BASF

Example 15

Preparation of Deodorant Stick Formulations Comprising an Invention's Compound of Formula (I)

A typical unperfumed deodorant stick formulation is listed in Table 13. The deodorant stick formulation is obtained by weighing all the components of Part A and heating to 70-75° C. Ceteareth-25 is added once the other Part A ingredients are mixed and heated. Once the Ceteareth-25 is dissolved, stearic acid is added. Part B is prepared by dissolving Triclosan in 1,2-propylene glycol. Evaporated water is compensated. Then, slowly, under mixing, Part B is poured into Part A.

TABLE 13

Composition of a typical unperfumed deodorant stick formulation.

| Phase | Ingredients | Amount [wt %] |
|---|---|---|
| A | Stearic acid | 5.05 |
| | 1,2-Propylene glycol | 41.87 |
| | Sodium hydroxide (20% aqueous solution) | 4.24 |
| | Water | 30.30 |
| | Tetrasodium EDTA (1) | 0.10 |
| | Ceteareth-25 (2) | 1.52 |
| | PPG-3 Myristyl ether (3) | 1.52 |
| B | 1,2-Propylene glycol | 15.14 |
| | Triclosan (4) | 0.25 |

(1) Edeta ® B Power; origin: BASF
(2) Cremophor ® A25; origin: BASF
(3) Tegosoft ® APM; origin: Evonik
(4) Irgasan ® DP 300; origin: BASF The perfumed deodorant stick formulation is then obtained by adding perfume oil (as e.g. described in Example 6, 0.85% by weight relative to the total weight of the deodorant stick formulation) and at least one of the invention's compounds of formula (I) such as, for example, compound 37, 33 or 18 i(0.10 to 0.20% by weight relative to the total weight of the deodorant stick formulation) under gentle shaking. To stock, a plastic bag is put into the bucket to be sealed after cooling. Moulds were filled at about 70° C.

Example 16

Preparation of Deodorant Roll-on Formulations Comprising an Invention's Compound of Formula (I)

A typical unperfumed deodorant roll-on formulation is listed in Table 14. Part A is prepared by sprinkling little-by-little the hydroxyethylcellulose into the water, whilst rapidly stirring with a turbine until the hydroxyethylcellulose is entirely swollen giving a limpid gel. Part B is slowly poured into Part A, whilst continuing stirring until the entire mixture is homogeneous. Then Part C is added.

TABLE 14

Composition of a typical unperfumed deodorant roll-on formulation.

| Phase | Ingredients | Amount [wt %] |
|---|---|---|
| A | Water | 50.51 |
| | Hydroxyethylcellulose (1) | 0.71 |
| B | Ethanol (95%) | 40.40 |
| | 1,2-Propylene glycol | 5.05 |
| | Triclosan (2) | 0.30 |
| C | PEG-40 hydrogenated castor oil (3) | 3.03 |

(1) Natrosol ® 250 H; origin: Ashland
(2) Irgasan ® DP 300; origin: BASF
(3) Cremophor ® RH 40; origin: BASF The perfumed deodorant roll-on formulation is then obtained by adding perfume oil (as e.g. described in Example 6, 0.85% by weight relative to the total weight of the deodorant stick formulation) and at least one of the invention's compounds of formula (I) such as, for example, compound 37, 33 or 18 (0.10-0.20% by weight relative to the total weight of the deodorant stick formulation) under gentle shaking.

Example 17

Preparation of Day Cream Base O/W Emulsions Comprising an Invention's Compound of Formula (I)

A typical day cream base O/W emulsion formulation comprising an invention's compound of formula (I) is listed in Table 15. Phases A and B are heated separately to 70-75° C., then Phase A is added to Phase B and vacuum is applied. The mixture is stirred and cooled to 55° C. for 15 min. After cooling to room temperature, phenoxyethanol (and) piroctone olamine (Part C) are added when a temperature of 45° C. is reached. The mixture is stirred for 5 min before sodium carbomer (Part D), a perfume oil (as e.g. described in Example 6) and at least one of the invention's compounds of formula (I) (Part E) are added. The mixture is stirred for 3 min, then the stirring was stopped for 15 min. When the temperature of the mixture reaches 30° C., the stirring is resumed for another 15 min until the cream becomes homogeneous, glossy and without lumps. If necessary the pH is adjusted to 6.70-7.20 with Glydant®, Phenoni®p or Nipaguard® PO5 or to 6.30-7.00 with Nikkoguard®.

TABLE 15

Composition of a typical day cream base O/W emulsion.

| Phase | Ingredients | Amount [wt %] |
|---|---|---|
| A | Steareth-2 (and) PEG-8 Distearate(1) | 5.0 |
| | Cetyl alcohol | 0.5 |
| | Ceteth-20 (and) glyceryl stearate (and) PEG-6 stearate (and) Steareth-20 (2) | 4.0 |
| | Squalan (3) | 1.0 |
| | Paraffin oil (4) | 2.0 |
| | Petrolatum (5) | 5.5 |
| B | Deionized water | 75.9 |
| | Propylene glycol | 5.0 |
| C | Phenoxyethanol (and) Piroctone olamine (6) | 0.6 |
| D | Sodium carbomer (7) | 0.2 |
| E | Perfume oil (as in Example 6) | 0.15 |
| | Compound of formula (I) | 0.15 |

(1) Arlacel ® 985; origin: Croda
(2) Tefose ® 2561; origin: Gattefossé
(3) Biolip P 90; origin: Gattefossé
(4) Mineral oil 30-40 CPS
(5) Petroleum jelly
(6) Nipaguard ® PO 5; origin: Clariant
(7) PNC400

Example 18

Preparation of Liquid Detergent Formulations Comprising an Invention's Compound of Formula (I)

A typical liquid detergent formulation is prepared by mixing the ingredients listed in Table 16. Then a perfume oil (as e.g. described in Example 6, 0.3 to 0.8% by weight relative to the total weight of the liquid detergent) and at least one of the invention's compounds of formula (I) such as, for example, compound 37, 33 or 18 (0.05 to 1.0% by weight relative to the total weight of the liquid detergent) are added under gentle shaking into the unperfumed liquid detergent formulation of Table 16.

TABLE 16

Composition of a typical unperfumed liquid detergent formulation.

| Ingredients | Amount [wt %] |
|---|---|
| Sodium $C_{14-17}$ alkyl sec. sulfonate (1) | 7.0 |
| Fatty acids, $C_{12-18}$ and $C_{18}$-unsaturated (2) | 7.5 |
| $C_{12/14}$ fatty alcohol polyglycol ether with 7 mol EO (3) | 17.0 |
| Triethanolamine | 7.5 |
| Propylene glycol | 11.0 |
| Citric acid | 6.5 |
| Potassium hydroxyde | 9.5 |
| Properase ® L (4) | 0.2 |
| Puradax ® EG L (4) | 0.2 |
| Purastar ® ST L (4) | 0.2 |
| Acrylates/Steareth-20 methacrylate structuring crosspolymer (5) | 6.0 |
| Deionized water | 27.4 |

(1) Hostapur ® SAS 60; origin: Clariant
(2) Edenor ® K 12-18; origin: Cognis
(3) Genapol ® LA 070; origin: Clariant
(4) Origin: Genencor International
(5) Aculyn ® 88; origin: Dow Chemicals

Example 19

Preparation of Hand Dishwash Formulations Comprising an Invention's Compound of Formula (I)

A typical unperfumed hand dishwash formulation is listed in Table 17. The unperfumed hand dishwash is prepared by mixing water with sodium hydroxide and diethanolamide. Then the linear alkylbenzene sulfonic acid is added. After neutralizing, the remaining ingredients are added and the pH is adjusted to 7-8 if necessary.

TABLE 17

Composition of a typical unperfumed hand dishwash formulation.

| Ingredients | Amount [wt %] |
|---|---|
| Linear alkylbenzene sulfonic acid (1) | 20.0 |
| Diethanolamide (2) | 3.5 |
| Sodium hydroxide (50%) (3) | 3.4 |
| Secondary alcohol ethoxolate (4) | 2.5 |
| Sodium xylene sulfonate | 6.3 |
| Deionized water | 64.3 |

(1) Biosoft ® S-118; origin: Stepan
(2) Ninol ® 40-CO; origin: Stepan
(3) Stepanate ® SXS; origin: Stepan
(4) Tergitol ® 15-S-9; origin: Dow Chemicals The perfumed hand dishwash formulation is then obtained by adding perfume oil (as e.g. described in Example 6, 0.85% by weight relative to the total weight of the hand dishwash formulation) and at least one of the invention's compounds of formula (I) such as, for example, compound 37, 33 or 18 (0.10 to 0.20% by weight relative to the total weight of the dishwash formulation) under gentle shaking into the unperfumed hand dishwash formulation of Table 17.

The invention claimed is:

1. A method to release from a precursor compound, compounds selected from the group consisting of a) a carbonyl compound of formula (II)

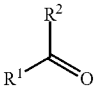

wherein $R^1$ is a $C_{1-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a hydroxy, $C_{1-15}$ alkyl, $C_{2-15}$ alkenyl, $C_{1-15}$ alkoxy, $C_{2-15}$ alkenyloxy, $C_{3-15}$ cycloalkyl, $C_{5-15}$ cycloalkenyl, $C_{3-15}$ heterocycloalkyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^2$ represents a hydrogen atom, a $C_{1-6}$ alkyl or phenyl group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

b) a formate ester of formula (III)

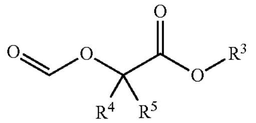

$R^3$ represents a hydrogen atom, a $C_{1-10}$ alkyl group, a $C_{3-10}$ alkenyl group, a benzyl group, a 2-phenylethyl group or a $C_{5-8}$ cycloalkyl group optionally substituted by one, two or three $C_{1-4}$ alkyl groups;

$R^4$ represents a hydrogen atom, a $C_{1-6}$ alkyl, a phenyl or a $CH_2C(O)OR^3$ group;

wherein $R^3$ has the same meaning as defined above;

$R^5$ represents a hydrogen atom or a methyl group;

c) an alcohol of formula (IV)

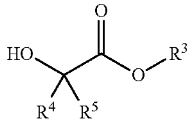

wherein $R^3$, $R^4$ and $R^5$ have the same meaning as defined above;

wherein the precursor compound comprises a compound of formula (I)

(I)

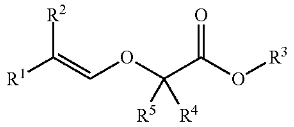

in the form of any one of its stereoisomers or a mixture thereof, and wherein $R^1$, $R^2$, $R^3$, $R^4$ and $R^5$ have the same meaning as defined above;

by exposing the precursor compound of formula (I) to an environment wherein the compound is oxidized.

2. The method according to claim 1, wherein $R^2$ is a hydrogen atom or a $C_{1-3}$ alkyl group.

3. The method according to claim 1, wherein $R^4$ is a hydrogen atom or a $C_{1-3}$ alkyl group.

4. The method according to claim 1, wherein $R^5$ is a hydrogen atom or when $R^4$ is a methyl group, $R^5$ is a hydrogen atom or methyl group.

5. The method according to claim 1, wherein $R^1$ is a $C_{1-10}$ alkyl, $C_{3-10}$ alkenyl, $C_{3-11}$ cycloalkyl or $C_{5-11}$ cycloalkenyl group, each optionally substituted with one or more of a $C_{1-4}$ alkyl, $C_{1-4}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-4}$ alkyl, hydroxy and/or $C_{1-4}$ alkoxy group.

6. The method according to claim 1, wherein $R^1$ is a naphthyl group or a phenyl group optionally substituted by one or two $R^{1'}$ group wherein $R^{1'}$, simultaneously or independently, represents a hydroxy group, a $C_{1-3}$ alkyl group, a $C_{1-3}$ alkoxy group, a $R^aCOO$ group, a $R^aOCO$ group wherein $R^a$ is a hydrogen atom, a $C_{1-3}$ alkyl group, a $C_{2-3}$ alkenyl group, or two adjacent $R^{1'}$, when taken together, represent a —O—$(CH_2)_m$—O— wherein m is 1 or 2 or form a $C_{5-6}$ saturated or unsaturated ring.

7. The method according to claim 1, wherein the compound of formula (II) and/or (IV) are a perfuming ingredient.

8. The method according to claim 1, wherein the environment wherein the compound is oxidized is air.

9. A method to confer, enhance, improve or modify the odor properties of a perfuming composition, the air surrounding the perfuming composition, a surface or a perfumed article, comprising adding to the composition, the air, or article, or contacting or treating the surface with an effective amount of at least one compound of formula (I) as defined in claim 1.

10. A method for intensifying or prolonging the diffusion effect of the characteristic fragrance of at least one carbonyl compound of formula (II):

(II)

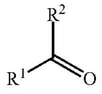

wherein $R^1$ is a $C_{1-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a hydroxy, $C_{1-15}$ alkyl, $C_{2-15}$ alkenyl, $C_{1-15}$ alkoxy, $C_{2-15}$ alkenyloxy, $C_{3-15}$ cycloalkyl, $C_{5-15}$ cycloalkenyl, $C_{3-15}$ heterocycloalkyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^2$ represents a hydrogen atom, a $C_{1-6}$ alkyl or phenyl group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom, and/or of at least one active formate ester of formula (III):

(III)

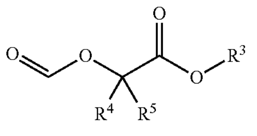

wherein $R^3$ represents a hydrogen atom, a $C_{1-10}$ alkyl group, a $C_{3-10}$ alkenyl group, a benzyl group, a 2-phenylethyl group or a $C_{5-8}$ cycloalkyl group optionally substituted by one, two or three $C_{1-4}$ alkyl groups;

$R^4$ represents a hydrogen atom, a $C_{1-6}$ alkyl, a phenyl or a $CH_2C(O)OR^3$ group;

wherein $R^3$ has the same meaning as defined above;

$R^5$ represents a hydrogen atom or a methyl group, and/or of at least one active alcohol of formula (IV):

(IV)

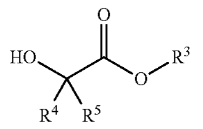

wherein $R^3$, $R^4$ and $R^5$ have the same meaning as defined above, on a surface or the air surrounding the perfuming composition, wherein the surface, or the air is treated with at least one compound (I) as defined in claim 1, or with a composition or article containing at least one compound (I), under conditions susceptible of allowing the release of at least one ketone or aldehyde formula (II), of at least one formate ester of formula (III) and/or of at least one alcohol of formula (IV) over time.

11. A perfuming composition comprising i) at least one compound of formula (I), as defined claim 1;

ii) at least one ingredient selected from the group consisting of a perfumery carrier and a perfumery base; and iii) optionally at least one perfumery adjuvant.

12. A perfumed consumer product comprising at least one compound of formula (I), as defined in claim 1.

13. The perfumed consumer product according to claim 12, characterized in that the perfumery consumer product is a perfume, a fabric care product, a body-care product, a cosmetic preparation, a skin-care product, an air care product or a home care product.

14. The perfumed consumer product according to claim 13, characterized in that the perfumery consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a hair conditioning product, a vanishing cream, a deodorant or antiperspirant, a hair remover, a tanning or sun product, a nail product, a skin cleansing, a makeup, a perfumed soap, a shower or bath mousse, an oil or gel, or a foot/hand care product, a hygiene product, an air freshener, a "ready to use" powdered air freshener, a mold remover, a furniture care product, a wipe, a dish detergent or hard-surface detergent, a leather care product, a car care product.

15. A compound of formula (I)

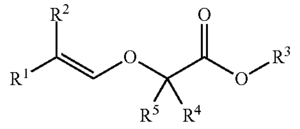

in the form of any one of its stereoisomers or a mixture thereof and wherein $R^1$ is a $C_{2-15}$ alkyl, $C_{3-15}$ alkenyl, $C_{6-10}$ aryl, $C_{3-15}$ cycloalkyl, $C_{5-15}$ cycloalkenyl or $C_{3-14}$ heterocycloalkyl group, each optionally substituted with one or more of a hydroxy, $C_{1-15}$ alkyl, $C_{2-15}$ alkenyl, $C_{1-15}$ alkoxy, $C_{2-15}$ alkenyloxy, $C_{3-15}$ cycloalkyl, $C_{5-15}$ cycloalkenyl, $C_{3-15}$ heterocycloalkyl, carboxylic acid, $C_{1-4}$ carboxylic ester, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^2$ represents a hydrogen atom, a $C_{1-3}$ alkyl or a phenyl group; or $R^1$ and $R^2$, when taken together, form a $C_{5-16}$ cycloalkyl, $C_{5-16}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen atom;

$R^3$ represents a $C_{1-10}$ alkyl group, a $C_{3-10}$ alkenyl group, a benzyl group, a 2-phenylethyl group or a $C_{5-8}$ cycloalkyl group optionally substituted by one, two or three $C_{1-4}$ alkyl groups;

$R^4$ represents a hydrogen atom or a methyl, phenyl or $CH_2C(O)OR^3$ group; wherein $R^3$ has the same meaning as defined above;

$R^5$ represents a hydrogen atom or a methyl group; and provided that when $R^2$, $R^4$ and $R^5$ are a hydrogen atom, $R^1$ is not an unsubstituted phenyl group; and provided that methyl 2-((2,2-diphenylvinyl) oxy) acetate and ethyl 2-((3-phenylprop-1-en-1-yl) oxy) acetate are excluded.

16. The method according to claim 1, wherein:

$R^2$ is a hydrogen atom or a methyl group; and/or $R^4$ is a hydrogen atom and or a methyl group; and/or $R^5$ is a hydrogen atom or when $R^4$ is a methyl group, $R^5$ is a hydrogen atom or methyl group.

17. The method according to claim 16, wherein $R^1$ is a $C_{1-10}$ alkyl, $C_{3-10}$ alkenyl, $C_{3-11}$ cycloalkyl or $C_{5-11}$ cycloalkenyl group, each optionally substituted with one or more of a $C_{1-4}$ alkyl, $C_{1-4}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-4}$ alkyl, hydroxy and/or $C_{1-4}$ alkoxy group.

18. The method according to claim 16, wherein $R_1$ is a naphthyl group or a phenyl group optionally substituted by one or two $R_{1'}$ group wherein $R^{1'}$, simultaneously or independently, represents a hydroxy group, a $C_{1-3}$ alkyl group, a $C_{1-3}$ alkoxy group, a $R^aCOO$ group, a $R^aOCO$ group wherein $R^a$ is a hydrogen atom, a $C_{1-3}$ alkyl group, a $C_{2-3}$ alkenyl group, or two adjacent $R^{1'}$, when taken together, represent a $—O—(CH_2)_m—O—$ wherein m is 1 or 2 or form a $C_{5-6}$ saturated or unsaturated ring.

19. A method to confer, enhance, improve or modify the odor properties of a perfuming composition, the air surrounding the perfuming composition, a surface or a perfumed article, comprising adding to the composition, the air, or article, or contacting or treating the surface with an effective amount of at least one compound of formula (I) as defined in claim 16.

20. A perfumed consumer product comprising at least one compound of formula (I), as defined in claim 16.

* * * * *